US010829448B2

(12) United States Patent
Claremon et al.

(10) Patent No.: US 10,829,448 B2
(45) Date of Patent: Nov. 10, 2020

(54) SUBSTITUTED BENZOIMIDAZOLES AS MODULATORS OF ROR-γ

(71) Applicant: Vitae Pharmaceuticals, LLC, Madison, NJ (US)

(72) Inventors: David A. Claremon, Maple Glen, PA (US); Lawrence Wayne Dillard, Yardley, PA (US); Yi Fan, Doylestown, PA (US); Stephen D. Lotesta, Burlington, NJ (US); Suresh B. Singh, Kendall Park, NJ (US); Colin M. Tice, Maple Glen, PA (US); Wei Zhao, North Potomac, MD (US); Linghang Zhuang, Chalfont, PA (US)

(73) Assignee: Vitae Pharmaceuticals, LLC, Madison, NJ (US)

( * ) Notice: Subject to any disclaimer, the term of this patent is extended or adjusted under 35 U.S.C. 154(b) by 0 days.

(21) Appl. No.: 16/373,912

(22) Filed: Apr. 3, 2019

(65) Prior Publication Data
US 2020/0062707 A1    Feb. 27, 2020

Related U.S. Application Data

(63) Continuation of application No. 15/749,322, filed as application No. PCT/US2016/045318 on Aug. 3, 2016, now Pat. No. 10,301,261.

(60) Provisional application No. 62/341,999, filed on May 26, 2016, provisional application No. 62/320,890, filed on Apr. 11, 2016, provisional application No. 62/201,348, filed on Aug. 5, 2015.

(51) Int. Cl.
*A61K 31/4184* (2006.01)
*C07D 235/04* (2006.01)
*C07D 209/10* (2006.01)
*C07D 405/14* (2006.01)
*C07D 401/06* (2006.01)
*C07D 235/10* (2006.01)
*C07D 235/12* (2006.01)
*C07D 401/12* (2006.01)
*C07D 405/06* (2006.01)
*C07D 471/04* (2006.01)
*C07D 235/26* (2006.01)
*C07D 401/14* (2006.01)

(52) U.S. Cl.
CPC ......... *C07D 209/10* (2013.01); *C07D 235/10* (2013.01); *C07D 235/12* (2013.01); *C07D 235/26* (2013.01); *C07D 401/06* (2013.01); *C07D 401/12* (2013.01); *C07D 401/14* (2013.01); *C07D 405/06* (2013.01); *C07D 405/14* (2013.01); *C07D 471/04* (2013.01); *C07B 2200/07* (2013.01); *C07B 2200/09* (2013.01)

(58) Field of Classification Search
CPC .................... A61K 31/4184; C07D 235/04
USPC ....................... 514/394; 548/361.1
See application file for complete search history.

(56) References Cited

U.S. PATENT DOCUMENTS

| 5,238,950 A | 8/1993 | Clader et al. |
| 5,272,158 A | 12/1993 | Hartman et al. |
| 5,326,760 A | 7/1994 | McElroy et al. |
| 5,364,869 A | 11/1994 | De |
| 5,389,631 A | 2/1995 | Claremon et al. |
| 5,571,774 A | 11/1996 | Hamprecht et al. |
| 5,719,144 A | 2/1998 | Hartman et al. |
| 5,770,590 A | 6/1998 | Natsugari et al. |
| 5,786,352 A | 7/1998 | Natsugari et al. |
| 5,959,116 A | 9/1999 | Hamprecht et al. |
| 6,103,659 A | 8/2000 | Pasenok et al. |
| 6,177,443 B1 | 1/2001 | Madsen et al. |
| 6,348,032 B1 | 2/2002 | Sperl et al. |
| 6,417,207 B1 | 7/2002 | Garvey et al. |
| 6,444,617 B1 | 9/2002 | Takaishi et al. |
| 6,489,315 B1 | 12/2002 | Natsugari et al. |
| 6,512,117 B1 | 1/2003 | Harclerode et al. |

(Continued)

FOREIGN PATENT DOCUMENTS

| CA | 2031684 A1 | 6/1991 |
| CA | 2134192 A1 | 5/1995 |

(Continued)

OTHER PUBLICATIONS

U.S. Appl. No. 14/888,129, filed Oct. 30, 2015, U.S. Pat. No. 9,868,748, Issued.

(Continued)

*Primary Examiner* — Douglas M Willis
(74) *Attorney, Agent, or Firm* — McCarter & English, LLP; Michael J. DeGrazia

(57) ABSTRACT

Provided are indole, benzoimidazole, pyrrolopyridine, and imidazopyridine derivatives and pharmaceutical compositions thereof, which are useful in the treatment of diseases and disorders mediated by RORγ. Such derivatives include e.g., those having the Formula II:

(II)

as well as pharmaceutically acceptable salts thereof. The disclosed derivatives may be used for treating one or more inflammatory, metabolic, autoimmune and other diseases or disorders.

6 Claims, No Drawings

(56) References Cited

U.S. PATENT DOCUMENTS

| | | |
|---|---|---|
| 6,770,666 B2 | 8/2004 | Hashimoto et al. |
| 7,112,600 B1 | 9/2006 | Hashimoto et al. |
| 7,115,752 B2 | 10/2006 | Lesieur et al. |
| 7,183,318 B2 | 2/2007 | Lesieur et al. |
| 7,244,730 B2 | 7/2007 | Suzuki et al. |
| 7,732,616 B2 | 6/2010 | Marlow et al. |
| 7,750,021 B2 | 7/2010 | Mi et al. |
| 8,389,739 B1 | 3/2013 | Thacher et al. |
| 8,399,477 B2 | 3/2013 | Alisi et al. |
| 8,415,351 B2 | 4/2013 | Wagner et al. |
| 9,266,886 B2 | 2/2016 | Lotesta et al. |
| 9,481,674 B1 | 11/2016 | Claremon et al. |
| 9,624,217 B2 | 4/2017 | Claremon et al. |
| 9,663,515 B2 | 5/2017 | Claremon et al. |
| 9,796,710 B2 | 10/2017 | Claremon et al. |
| 9,868,748 B2 | 1/2018 | Claremon et al. |
| 10,047,085 B2 | 8/2018 | Claremon et al. |
| 10,087,184 B2 | 10/2018 | Claremon et al. |
| 10,301,261 B2 | 5/2019 | Claremon et al. |
| 10,399,976 B2 | 9/2019 | Claremon et al. |
| 2002/0132817 A1 | 9/2002 | Natsugari et al. |
| 2003/0050320 A1 | 3/2003 | Hashimoto et al. |
| 2004/0002424 A1 | 1/2004 | Minn et al. |
| 2004/0038973 A1 | 2/2004 | Nahra et al. |
| 2005/0004204 A1 | 1/2005 | Suzuki et al. |
| 2005/0020593 A1 | 1/2005 | Mailliet et al. |
| 2005/0234065 A1 | 10/2005 | Hulin et al. |
| 2006/0135557 A1 | 6/2006 | Nan et al. |
| 2007/0032497 A1 | 2/2007 | Hashimoto et al. |
| 2007/0112038 A1 | 5/2007 | Marlow et al. |
| 2007/0258887 A1 | 11/2007 | Tamagnan et al. |
| 2008/0277622 A1 | 11/2008 | Deshpande et al. |
| 2008/0287462 A1 | 11/2008 | Chessari et al. |
| 2009/0036423 A1 | 2/2009 | Pan et al. |
| 2009/0076275 A1 | 3/2009 | Bolin et al. |
| 2009/0233945 A9 | 9/2009 | Chessari et al. |
| 2009/0258871 A1 | 10/2009 | Jitsuoka et al. |
| 2009/0270405 A1 | 10/2009 | Cook, II et al. |
| 2010/0099684 A1 | 4/2010 | Cook, II et al. |
| 2011/0070193 A1 | 3/2011 | Wagner et al. |
| 2011/0189167 A1 | 8/2011 | Flynn et al. |
| 2011/0313003 A1 | 12/2011 | Shi et al. |
| 2012/0077840 A1 | 3/2012 | Turner et al. |
| 2012/0115903 A1 | 5/2012 | Frank et al. |
| 2012/0245163 A1 | 9/2012 | Gomtsyan et al. |
| 2012/0322837 A1 | 12/2012 | Maeba et al. |
| 2013/0143870 A1 | 6/2013 | Grauert et al. |
| 2013/0150347 A1 | 6/2013 | Rudolf et al. |
| 2014/0163001 A1 | 6/2014 | Yamamoto et al. |
| 2014/0228409 A1 | 8/2014 | Yamamoto et al. |
| 2019/0322687 A1 | 10/2019 | Claremon et al. |
| 2019/0352286 A1 | 11/2019 | Claremon et al. |

FOREIGN PATENT DOCUMENTS

| | | |
|---|---|---|
| CA | 2352612 A1 | 6/2000 |
| CA | 2524027 A1 | 12/2004 |
| CN | 1424770 A | 6/2003 |
| CN | 1869036 A | 11/2006 |
| CN | 101225070 A | 7/2008 |
| CN | 101455661 A | 6/2009 |
| CN | 102180780 A | 9/2011 |
| CN | 104024239 A | 9/2014 |
| DE | 4343922 A1 | 6/1995 |
| DE | 4446396 A1 | 7/1995 |
| EP | 254951 A2 | 2/1988 |
| EP | 321368 A1 | 6/1989 |
| EP | 468187 A2 | 1/1992 |
| EP | 520277 A2 | 12/1992 |
| EP | 520573 A1 | 12/1992 |
| EP | 540334 A1 | 5/1993 |
| EP | 655439 A2 | 5/1995 |
| EP | 733632 A1 | 9/1996 |
| EP | 1178048 A1 | 2/2002 |
| EP | 2327704 A1 | 6/2011 |
| FR | 2725946 A1 | 4/1996 |
| FR | 2926554 A1 | 7/2009 |
| GB | 2276384 A | 9/1994 |
| JP | H06-236056 A | 8/1994 |
| JP | H11-43489 A | 2/1999 |
| JP | 2000-007661 A | 1/2000 |
| JP | 2003-171380 A | 6/2003 |
| JP | 2003-531894 A | 10/2003 |
| JP | 2004-203791 A | 7/2004 |
| JP | 2015-124178 A | 7/2015 |
| WO | WO-1990/09787 A1 | 9/1990 |
| WO | WO-1994/00119 A1 | 1/1994 |
| WO | WO-1994/24712 A1 | 10/1994 |
| WO | WO-1995/11680 A1 | 5/1995 |
| WO | WO-1995/17397 A1 | 6/1995 |
| WO | WO-1996/26187 A1 | 8/1996 |
| WO | WO-1997/32832 A1 | 9/1997 |
| WO | WO-1998/40385 A1 | 9/1998 |
| WO | WO-1998/42666 A1 | 10/1998 |
| WO | WO-1999/47132 A2 | 9/1999 |
| WO | WO-1999/58495 A1 | 11/1999 |
| WO | WO-1999/58496 A1 | 11/1999 |
| WO | WO-2000/032192 A1 | 6/2000 |
| WO | WO-2000/067754 A1 | 11/2000 |
| WO | WO-2001/005790 A1 | 1/2001 |
| WO | WO-2001/09076 A2 | 2/2001 |
| WO | WO-2001/047883 A1 | 7/2001 |
| WO | WO-2001/051128 A1 | 7/2001 |
| WO | WO-2001/83438 A2 | 11/2001 |
| WO | WO-2001/083445 A1 | 11/2001 |
| WO | WO-2001/85722 A1 | 11/2001 |
| WO | WO-2002/024650 A2 | 3/2002 |
| WO | WO-2002/38107 A2 | 5/2002 |
| WO | WO-2002/081443 A1 | 10/2002 |
| WO | WO-2002/081447 A1 | 10/2002 |
| WO | WO-2002/081463 A1 | 10/2002 |
| WO | WO-2002/085855 A1 | 10/2002 |
| WO | WO-2002/094833 A1 | 11/2002 |
| WO | WO-2003/008421 A1 | 1/2003 |
| WO | WO-2003/029252 A1 | 4/2003 |
| WO | WO-2003/029254 A1 | 4/2003 |
| WO | WO-2003/043991 A1 | 5/2003 |
| WO | WO-2003/062241 A1 | 7/2003 |
| WO | WO-2003/066055 A1 | 8/2003 |
| WO | WO-2003/070710 A1 | 8/2003 |
| WO | WO-2003/076440 A1 | 9/2003 |
| WO | WO-2003/104216 A1 | 12/2003 |
| WO | WO-2004/014365 A1 | 2/2004 |
| WO | WO-2004/026871 A1 | 4/2004 |
| WO | WO-2004/042029 A2 | 5/2004 |
| WO | WO-2004/065351 A1 | 8/2004 |
| WO | WO-2004/089897 A1 | 10/2004 |
| WO | WO-2004/103309 A2 | 12/2004 |
| WO | WO-2004/108133 A2 | 12/2004 |
| WO | WO-2004/111010 A1 | 12/2004 |
| WO | WO-2004/113330 A1 | 12/2004 |
| WO | WO-2005/005392 A1 | 1/2005 |
| WO | WO-2005/011601 A2 | 2/2005 |
| WO | WO-2005/023806 A2 | 3/2005 |
| WO | WO-2005/025504 A2 | 3/2005 |
| WO | WO-2005/028480 A2 | 3/2005 |
| WO | WO-2005/039564 A1 | 5/2005 |
| WO | WO-2005/051301 A2 | 6/2005 |
| WO | WO-2005/060958 A1 | 7/2005 |
| WO | WO-2005/063296 A2 | 7/2005 |
| WO | WO-2005/097129 A2 | 10/2005 |
| WO | WO-2005/100334 A1 | 10/2005 |
| WO | WO-2005/117890 A2 | 12/2005 |
| WO | WO-2006/032631 A1 | 3/2006 |
| WO | WO-2006/062981 A2 | 6/2006 |
| WO | WO-2006/065842 A2 | 6/2006 |
| WO | WO-2006/074428 A2 | 7/2006 |
| WO | WO-2006/082001 A1 | 8/2006 |
| WO | WO-2006/092731 A1 | 9/2006 |
| WO | WO-2006/109085 A1 | 10/2006 |
| WO | WO-2007/007054 A1 | 1/2007 |
| WO | WO-2007/036733 A1 | 4/2007 |
| WO | WO-2007/036734 A1 | 4/2007 |
| WO | WO-2007/050124 A1 | 5/2007 |

(56) References Cited

FOREIGN PATENT DOCUMENTS

| | | |
|---|---|---|
| WO | WO-2007/084451 A1 | 7/2007 |
| WO | WO-2007/084455 A1 | 7/2007 |
| WO | WO-2007/084815 A2 | 7/2007 |
| WO | WO-2007/087231 A2 | 8/2007 |
| WO | WO-2007/097931 A2 | 8/2007 |
| WO | WO-2007/101224 A2 | 9/2007 |
| WO | WO-2007/107545 A1 | 9/2007 |
| WO | WO-2007/109596 A2 | 9/2007 |
| WO | WO-2007/131982 A2 | 11/2007 |
| WO | WO-2008/013963 A2 | 1/2008 |
| WO | WO-2008/044027 A2 | 4/2008 |
| WO | WO-2008/044029 A1 | 4/2008 |
| WO | WO-2008/044041 A1 | 4/2008 |
| WO | WO-2008/044045 A1 | 4/2008 |
| WO | WO-2008/044054 A2 | 4/2008 |
| WO | WO-2008/048991 A2 | 4/2008 |
| WO | WO-2008/073865 A2 | 6/2008 |
| WO | WO-2008/083070 A1 | 7/2008 |
| WO | WO-2008/086161 A1 | 7/2008 |
| WO | WO-2008/132155 A2 | 11/2008 |
| WO | WO-2008/135524 A2 | 11/2008 |
| WO | WO-2008/135526 A1 | 11/2008 |
| WO | WO-2008/149163 A2 | 12/2008 |
| WO | WO-2009/004496 A2 | 1/2009 |
| WO | WO-2009/013299 A2 | 1/2009 |
| WO | WO-2009/026248 A2 | 2/2009 |
| WO | WO-2009/050228 A2 | 4/2009 |
| WO | WO-2009/052319 A1 | 4/2009 |
| WO | WO-2009/052320 A1 | 4/2009 |
| WO | WO-2009/068463 A2 | 6/2009 |
| WO | WO-2009/073788 A1 | 6/2009 |
| WO | WO-2009/083526 A1 | 7/2009 |
| WO | WO-2009/097972 A1 | 8/2009 |
| WO | WO-2009/112445 A1 | 9/2009 |
| WO | WO-2009/112678 A2 | 9/2009 |
| WO | WO-2009/112826 A1 | 9/2009 |
| WO | WO-2009/112839 A1 | 9/2009 |
| WO | WO-2009/124755 A1 | 10/2009 |
| WO | WO-2009/131926 A1 | 10/2009 |
| WO | WO-2009/144450 A1 | 12/2009 |
| WO | WO-2010/003022 A1 | 1/2010 |
| WO | WO-2010/021878 A1 | 2/2010 |
| WO | WO-2010/033350 A1 | 3/2010 |
| WO | WO-2010/056194 A1 | 5/2010 |
| WO | WO-2010/056195 A1 | 5/2010 |
| WO | WO-2010/077680 A2 | 7/2010 |
| WO | WO-2010/086311 A1 | 8/2010 |
| WO | WO-2011/078143 A1 | 6/2011 |
| WO | WO-2011/090473 A1 | 7/2011 |
| WO | WO-2011/094545 A2 | 8/2011 |
| WO | WO-2011/107248 A1 | 9/2011 |
| WO | WO-2011/140936 A1 | 11/2011 |
| WO | WO-2011/146358 A1 | 11/2011 |
| WO | WO-2011/159297 A1 | 12/2011 |
| WO | WO-2012/019015 A2 | 2/2012 |
| WO | WO-2012/027965 A1 | 3/2012 |
| WO | WO-2012/028100 A1 | 3/2012 |
| WO | WO-2012/031197 A1 | 3/2012 |
| WO | WO-2012/043505 A1 | 4/2012 |
| WO | WO-2012/062462 A1 | 5/2012 |
| WO | WO-2012/064744 A2 | 5/2012 |
| WO | WO-2012/100732 A1 | 8/2012 |
| WO | WO-2012/100734 A1 | 8/2012 |
| WO | WO-2012/106995 A1 | 8/2012 |
| WO | WO-2012/125521 A1 | 9/2012 |
| WO | WO-2012/136296 A1 | 10/2012 |
| WO | WO-2012/139775 A1 | 10/2012 |
| WO | WO-2013/000994 A1 | 1/2013 |
| WO | WO-2013/019621 A1 | 2/2013 |
| WO | WO-2013/019626 A1 | 2/2013 |
| WO | WO-2013/019635 A1 | 2/2013 |
| WO | WO-2013/019653 A1 | 2/2013 |
| WO | WO-2013/019682 A1 | 2/2013 |
| WO | WO-2013/029338 A1 | 3/2013 |
| WO | WO-2013/045431 A1 | 4/2013 |
| WO | WO-2013/064231 A1 | 5/2013 |
| WO | WO-2013/067036 A1 | 5/2013 |
| WO | WO-2013/078233 A1 | 5/2013 |
| WO | WO-2013/078240 A1 | 5/2013 |
| WO | WO-2013/079223 A1 | 6/2013 |
| WO | WO-2013/083741 A1 | 6/2013 |
| WO | WO-2013/087739 A1 | 6/2013 |
| WO | WO-2013/092460 A1 | 6/2013 |
| WO | WO-2013/092939 A1 | 6/2013 |
| WO | WO-2013/092941 A1 | 6/2013 |
| WO | WO-2013/096496 A2 | 6/2013 |
| WO | WO-2013/100027 A1 | 7/2013 |
| WO | WO-2013/159095 A1 | 10/2013 |
| WO | WO-2013/160418 A1 | 10/2013 |
| WO | WO-2013/160419 A1 | 10/2013 |
| WO | WO-2013/166013 A1 | 11/2013 |
| WO | WO-2013/169588 A1 | 11/2013 |
| WO | WO-2013/169704 A2 | 11/2013 |
| WO | WO-2013/169864 A2 | 11/2013 |
| WO | WO-2013/171729 A2 | 11/2013 |
| WO | WO-2013/178362 A1 | 12/2013 |
| WO | WO-2014/008214 A1 | 1/2014 |
| WO | WO-2014/009447 A1 | 1/2014 |
| WO | WO-2014/026327 A1 | 2/2014 |
| WO | WO-2014/026328 A1 | 2/2014 |
| WO | WO-2014/026329 A1 | 2/2014 |
| WO | WO-2014/026330 A1 | 2/2014 |
| WO | WO-2014/028589 A2 | 2/2014 |
| WO | WO-2014/028591 A2 | 2/2014 |
| WO | WO-2014/028597 A2 | 2/2014 |
| WO | WO-2014/028600 A2 | 2/2014 |
| WO | WO-2014/028669 A1 | 2/2014 |
| WO | WO-2014/044738 A1 | 3/2014 |
| WO | WO-2014/062938 A1 | 4/2014 |
| WO | WO-2014/086894 A1 | 6/2014 |
| WO | WO-2014/179564 A1 | 11/2014 |
| WO | WO-2015/083130 A1 | 6/2015 |
| WO | WO-2015/100420 A1 | 7/2015 |
| WO | WO-2015/101928 A1 | 7/2015 |
| WO | WO-2015/114157 A1 | 8/2015 |
| WO | WO-2015/116904 A1 | 8/2015 |
| WO | WO-2015/144480 A1 | 10/2015 |
| WO | WO-2015/144605 A1 | 10/2015 |
| WO | WO-2015/144609 A1 | 10/2015 |
| WO | WO-2015/144803 A1 | 10/2015 |
| WO | WO-2015/159233 A1 | 10/2015 |
| WO | WO-2016/061160 A1 | 4/2016 |
| WO | WO-2016/064970 A1 | 4/2016 |
| WO | WO-2017/024018 A1 | 2/2017 |
| WO | WO-2017/087608 A1 | 5/2017 |
| WO | WO-2017/132432 A1 | 8/2017 |

OTHER PUBLICATIONS

U.S. Appl. No. 14/609,798, filed Jan. 30, 2015, U.S. Pat. No. 9,266,886, Issued.
U.S. Appl. No. 14/990,430, filed Jan. 7, 2016, U.S. Pat. No. 9,624,217, Issued.
U.S. Appl. No. 15/455,481, filed Mar. 10, 2017, U.S Pat. No. 10,047,085, Issued.
U.S. Appl. No. 16/025,155, filed Jul. 2, 2018, U.S. Pat. No. 10,399,976, Issued.
U.S. Appl. No. 16/506,518, filed Jul. 9, 2019, Pending.
U.S. Appl. No. 15/178,796, filed Jun. 10, 2016, U.S. Pat. No. 9,481,674, Issued.
U.S. Appl. No. 15/277,836, filed Sep. 27, 2016, U.S. Pat. No. 9,796,710, Issued.
U.S. Appl. No. 15/709,903, filed Sep. 20, 2017, U.S. Pat. No. 10,087,184, Issued.
U.S. Appl. No. 16/394,275, filed Apr. 25, 2019, Pending.
U.S. Appl. No. 14/933,524, filed Nov. 5, 2015, U.S. Pat. No. 9,663,515, Issued.
U.S. Appl. No. 16/394,764, filed Apr. 25, 2019, Pending.
U.S. Appl. No. 15/749,322, filed Jan. 31, 2018, U.S. Pat. No. 10,301,261, Issued.
U.S. Appl. No. 15/776,836, filed May 17, 2018, 2019-0322687, Published.

(56) References Cited

OTHER PUBLICATIONS

U.S. Appl. No. 16/073,503, filed Jul. 27, 2018, 2019-0352286, Published.
Babu et al., Emerging therapeutic strategies in COPD. Drug Discov Today. Mar. 2015;20(3):371-9.
Bendele et al., Animal models of arthritis: relevance to human disease. Toxicol Pathol. Jan.-Feb. 1999;27(1):134-42.
Bendele, Animal models of rheumatoid arthritis. J Musculoskelet Neuronal Interact. Jun. 2001;1(4):377-85.
Campochiaro, The complexity of animal model generation for complex diseases. JAMA. Feb. 17, 2010;303(7):657-8.
Center for Disease Control, Classification of Diseases and Injuries. ICD-9-CM Tabular List of Diseases (FY03). 748 pages, accessed online Sep. 10, 2015.
Chaichian et al., Targeted Therapies in Systemic Lupus Erythematosus: A State-of-the-Art Review. J Clin Cell Immunol. 2013;S6:8 pages.
Chiba, Emerging Therapeutic Strategies in Alzheimer's Disease. InTech, retrieved online at: http://dx.doi.org/10.5772/55293. Chapter 9, pp. 181-225, (2013).
Cyr et al., Recent progress on nuclear receptor RORgamma modulators. Bioorganic & Medicinal Chemistry Letters. 2016;26:4387-4393.
Damia et al., Contemporary pre-clinical development of anticancer agents—What are the optimal preclinical models? European Journal of Cancer. 2009;45:2768-2781.
Edwards et al., Molecular genetics of AMD and current animal models. Angiogenesis. 2007;10(2):119-32.
Elborn, Cystic fibrosis. The Lancet. Retrieved online at: http://dx.doi.org/10.1016/S0140-6736(16)00576-6. 13 pages. Apr. 29, 2016.
Flowers et al., How we treat chronic graft-versus-host disease. Blood. Jan. 22, 2015;125(4):606-15.
Fries et al., O-divinylbenzene and naphthalene. Ber Dtsch Chem Ges B. 1936;69:715-22.
Fries et al., o-Divinylbenzol and Naphtalin. Annalen der Chemie. 1937;533:72-92.
Galiè et al., Guidelines for the diagnosis and treatment of pulmonary hypertension: the Task Force for the Diagnosis and Treatment of Pulmonary Hypertension of the European Society of Cardiology (ESC) and the European Respiratory Society (ERS), endorsed by the International Society of Heart and Lung Transplantation (ISHLT). Eur Heart J. Oct. 2009;30(20):2493-537.
Hackam et al., Translation of research evidence from animals to humans. JAMA. Oct. 11, 2006;296(14):1731-2.
Healthline, Overview. Retrieved online at: http://www.healthline.com/health/inflammatory-bowel-disease. 7 pages. (2005-2015).
Hynes et al., The discovery of (R)-2-(sec-butylamino)-N-(2-methyl-5-(methylcarbamoyl)phenyl) thiazole-5-carboxamide (BMS-640994)—A potent and efficacious p38alpha MAP kinase inhibitor. Bioorg Med Chem Lett. Mar. 15, 2008;18(6):1762-7.
Johnson et al., Relationships between drug activity in NCI preclinical in vitro and in vivo models and early clinical trials. Br J Cancer. May 18, 2001;84(10):1424-31.
Jordan, Tamoxifen: a most unlikely pioneering medicine. Nat Rev Drug Discov. Mar. 2003;2(3):205-13.
Lamotte et al., Discovery of novel indazole derivatives as dual angiotensin II antagonists and partial PPAR? agonists. Bioorg Med Chem Lett. Feb. 15, 2014;24(4):1098-103.
Ledford, US cancer institute to overhaul tumour cell lines. Nature. Feb. 25, 2016;530(7591):391.
Lim et al., Age-related macular degeneration. Lancet. May 5, 2012;379(9827):1728-38.
Lutz et al., Overview of Animal Models of Obesity. Curr Protoc Pharmacol. Sep. 2012. Chapter: Unit 5.61. 22 pages.
Maddur et al., Th17 cells: biology, pathogenesis of autoimmune and inflammatory diseases, and therapeutic strategies. Am J Pathol. Jul. 2012;181(1):8-18.
Makrilakis, Pathophysiology of Type 2 diabetes. Diabetes in Clinical Practice: Questions and Answers from Case Studies. John Wiley & Sons, Ltd. Chapter 3, pp. 43-58, (2006).
Marcoux et al., Annulation of ketones with vinamidinium hexafluorophosphate salts: an efficient preparation of trisubstituted pyridines. Org Lett. Jul. 27, 2000;2(15):2339-41.
Ocana et al.. Preclinical development of molecular-targeted agents for cancer. Nat Rev Clin Oncol. 2011;8:200-209.
Pilz et al., Modern multiple sclerosis treatment—what is approved, what is on the horizon. Drug Discov Today. Dec. 2008;13(23-24):1013-25.
Quinby, Conventional Therapy. Psoriasis and Psoriatic Arthritism. An Integrated Approach. Kenneth B. Gordon (Ed.), Springer-Verlag, Berlin Heidelberg. Chapter 9, pp. 134-184, (2005).
Sangshetti et al., Antileishmanial drug discovery: comprehensive review of the last 10 years. RSC Adv. 2015;5:32376-32415.
Schlecker et al., Regioselective Metalation of Pyridinylcarbamates and Pyridinecarboxamides with (2,2,6,6-Tetramethylpiperidino)magnesium Chloride. J Org Chem. 1995;60:8414-8416.
Schlecker et al., Regioselective Monometalation of 2,5-Pyridinedicarboxamides with (2,2,6,6-Tetramethylpiperidino)magnesium Chloride (TMPMgCl). Liebigs Ann. 1995;8:1441-1446.
Sharma et al., Cell line-based platforms to evaluate the therapeutic efficacy of candidate anticancer agents. Nat Rev Cancer. Apr. 2010;10(4):241-53.
Sime et al., Discovery of GSK1997132B a novel centrally penetrant benzimidazole PPAR? partial agonist. Bioorg Med Chem Lett. Sep. 15, 2011;21(18):5568-72.
University of Cambridge, Alzheimer's disease and tauopathy. John van Geest Centre for Brain Repair, School of Clinical Medicine. 1 page, (2016).
Vickers et al., The utility of animal models to evaluate novel anti-obesity agents. Br J Pharmacol. Oct. 2011;164(4):1248-62.
Vourloumis et al., Solid-phase synthesis of benzimidazole libraries biased for RNA targets. Tetrahedron Letters. 2003;44:2807-2811.
Wang et al., Structure-Based Design of Tetrahydroisoquinoline-7-carboxamides as Selective Discoidin Domain Receptor 1 (DDR1) Inhibitors. J Med Chem. Jun. 23, 2016;59(12):5911-6.
Yan et al., Quality control in combinatorial chemistry: determination of the quantity, purity, and quantitative purity of compounds in combinatorial libraries. J Comb Chem. Sep.-Oct. 2003;5(5):547-59.
European Office Action for Application No. 16816023.2, dated Jun. 27. 2019, 6 pages.
Co-pending U.S. Appl. No. 16/506,518, filed Jul. 9, 2019.
Co-pending U.S. Appl. No. 16/394,275, filed Apr. 25, 2019.
Co-pending U.S. Appl. No. 16/394,764, filed Apr. 25, 2019.

SUBSTITUTED BENZOIMIDAZOLES AS MODULATORS OF ROR-γ

RELATED APPLICATIONS

This application is a continuation of U.S. Pat. No. 10,301,261, filed Jan. 31, 2018, which is a 35 U.S.C. § 371 national stage filing of International Application No. PCT/US2016/045318, filed Aug. 3, 2016, which claims priority to U.S. Provisional Application No. 62/341,999, filed May 26, 2016, U.S. Provisional Application No. 62/320,890, filed Apr. 11, 2016, and U.S. Provisional Application No. 62/201,348, filed Aug. 5, 2015. The entire contents of the aforementioned applications are incorporated herein by reference in their entirety.

TECHNICAL FIELD

The present disclosure is directed to novel retinoic acid receptor-related orphan receptor gamma ("RORγ" or "ROR-gamma") modulators, processes for their preparation, pharmaceutical compositions containing these modulators, and their use in the treatment of inflammatory, metabolic, autoimmune and other diseases mediated by RORγ.

BACKGROUND

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal, 7:e003, doi:10.1621/nrs.07003, Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertnstert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., 2012, ACS Chem. Biol., 7:1515-1519, Epub 2012 Jul. 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Recently, IL-17-producing neutrophils have been identified as promoting inflammation leading to both microbial clearance and IL-17-associated tissue damage in the cornea and other tissues (Taylor et al., 2014, J. Inmunol, 192:3319-3327; Taylor et al., 2014, Nat. Immunol., 15:143-151), supporting a role for compounds that inhibit RORγ activity in the treatment of corneal ulcers and other diseases and disorders associated with IL-17 expressing neutrophils.

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6). Recent evidence also shows that RORγ is overexpressed and amplified in metastatic castration-resistant prostate cancer tumors, and that RORγ antagonists suppressed tumor growth in multiple androgen receptor-expressing xenograft prostate cancer models. See e.g., Nature Medicine, Mar. 28, 2016, advance online publication, doi: 10.1038/nm.4070.

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256; Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity, including IL17 production, will be of significant therapeutic benefit. It is therefore desirable to prepare compounds that inhibit RORγ activity and hence have utility in the treatment of inflammatory, autoimmune, metabolic, circadian effect, cancer, and other diseases mediated by RORγ, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY

It has now been found that compounds described herein, and pharmaceutically acceptable compositions thereof, are effective modulators of RORγ (see e.g., Table 1). Such compounds include those of Formula I:

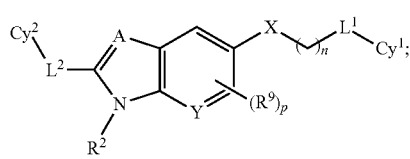

(I)

or a pharmaceutically acceptable salt thereof, wherein each of $Cy^2$, $L^2$, $R^2$, A, Y, $R^9$, p, X, n, $L^1$, and $Cy^1$ are as defined and described herein.

The provided compounds, and pharmaceutically acceptable compositions thereof, are modulators of RORγ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

DETAILED DESCRIPTION OF CERTAIN EMBODIMENTS

1. General Description of Compounds

In certain embodiments, the present disclosure provides a compound of Formula I:

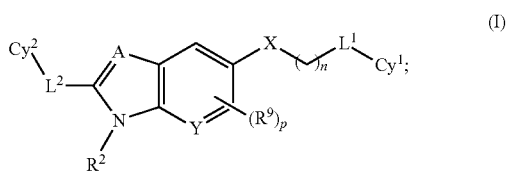

(I)

or a pharmaceutically acceptable salt thereof, wherein
  X is —C(O)NH— or —NHC(O)—;
  A is CH or N;
  Y is $CR^{10}$ or N;
  n is 0, 1, 2, or 3;
  p is 0, 1, or 2;
  $L^2$ is $CH_2$, $CH_2CH_2$, CHMe, O, C(=O), CH(OH), or $CH_2O$, where the oxygen atom in $CH_2O$ can either be attached to $Cy^2$ or to the carbon atom on the center ring bridging $NR^2$ and A;
  L is absent or is $CR^7R^8$;
  $Cy^1$ is selected from aryl, heteroaryl, heterocyclyl, and cycloalkyl, wherein the aryl, heteroaryl, heterocyclyl, and cycloalkyl are each substituted with 1 to 3 groups independently selected from $R^5$;
  $Cy^2$ is selected from aryl, heteroaryl, monocyclic cycloalkyl, and monocyclic heterocyclyl, wherein the aryl, heteroaryl, monocyclic cycloalkyl, and monocyclic heterocyclyl are each optionally substituted with 1 to 3 groups independently selected from $R^6$;
  $R^2$ is $(C_1-C_4)$alkyl, $(C_2-C_4)$alkenyl, $(C_1-C_4)$haloalkyl, or monocyclic cycloalkyl;
  $R^5$ and $R^6$ are each independently selected from halogen, —CN, —$OR^c$, —$NR^dR^e$, —$S(O)_kR^c$, —$NR^cS(O)_2R^c$, —$S(O)_2NR^dR^e$, —C(=O)$OR^c$, —OC(=O)$OR^c$, —OC(=O)$R^c$, —OC(=S)$OR^c$, —C(=S)$OR^c$, —OC(=S)$R^c$, —C(=O)$NR^dR^e$, —$NR^cC$(=O)$R^c$, —C(=S)$NR^dR^e$, —$NR^cC$(=S)$R^c$, —$NR^cC$(=O)$OR^c$, —OC(=O)$NR^dR^e$, —$NR^c$(C=S)$OR^c$, —OC(=S)$NR^dR^e$, —$NR^cC$(=O)$NR^dR^e$, —$NR^c$(C=S)$NR^dR^e$, —C(=S)$R^c$, —C(=O)$R^c$, $(C_1-C_6)$alkyl, cycloalkyl, —$(CH_2)_{1-4}$-cycloalkyl, heterocyclyl, —$(CH_2)_{1-4}$-heterocyclyl, aryl, —NHC(=O)-heterocyclyl, —NHC(=O)-cycloalkyl, —$(CH_2)_{1-4}$-aryl, heteroaryl and —$(CH_2)_{1-4}$-heteroaryl,
  wherein the alkyl, cycloalkyl, heterocyclyl, aryl or heteroaryl portion present in each of said $(C_1-C_6)$alkyl, cycloalkyl, —$(CH_2)_{1-4}$-cycloalkyl, heterocyclyl, —$(CH_2)_{1-4}$-heterocyclyl, aryl, —$(CH_2)_{1-4}$-aryl, heteroaryl and —$(CH_2)_{1-4}$-heteroaryl substituent for $R^6$ are further optionally substituted with halogen, $OR^c$, —$NO_2$, —CN, —$NR^cC$(=O)$R^c$, —$NR^dR^e$, —$S(O)_kR^c$, —C(=O)$OR^c$, —C(=O)$NR^dR^e$, —C(=O)$R^c$, $(C_1-C_3)$alkyl, halo$(C_1-C_3)$alkyl, $(C_1-C_3)$alkoxy$(C_1-C_3)$alkyl, $(C_1-C_3)$alkoxy, or halo$(C_1-C_3)$alkoxy; each $R^c$ is independently selected from hydrogen and $(C_1-C_6)$alkyl optionally substituted with 1 to 3 halogen;
  each $R^d$ and $R^e$ is independently selected from hydrogen and $(C_1-C_6)$alkyl;
  k is 0, 1 or 2;
  any heterocyclyl or heteroaryl portion of $Cy^1$ or $Cy^2$ is further optionally substituted with =O;
  $R^7$ and $R^8$ are each independently hydrogen, OH, $(C_1-C_3)$alkyl, hydroxy$(C_1-C_3)$alkyl, —O$(C_1-C_3)$alkyl, —$(C_1-C_3)$alkyl-O—$(C_1-C_3)$alkyl, —$(C_1-C_3)$alkyl-$NH_2$, —$(C_1-C_3)$alkyl-N-di$(C_1-C_3)$alkyl, $CO_2H$, $(CH_2)_{1-3}COOH$, monocyclic heterocyclyl, —CO—$(C_1-C_3)$alkoxy, —$(C_1-C_3)$alkoxy-C(O)—$NH_2$, —$(C_1-C_3)$alkyl-O—$(C_1-C_3)$alkyl-C(O)—$NH_2$, —$(C_1-C_3)$alkyl-C(O)—$(C_1-C_3)$alkoxy, —$(C_1-$ $C_3$)alkyl-C(O)—NH$_2$, halophenyl, —(C$_1$-C$_3$)alkyl-halophenyl, or quinolin-2(1H)one-4yl-methyl;

$R^9$ is independently (C$_1$-C$_4$)alkyl, (C$_1$-C$_4$)haloalkyl, (C$_1$-C$_4$)alkoxy, or halogen; and $R^{10}$ is hydrogen, (C$_1$-C$_4$)alkyl, (C$_1$-C$_4$)haloalkyl, (C$_1$-C$_4$) alkoxy, or halogen;

provided that:

when A is N, Y is CR$^{10}$, R$^{10}$ is hydrogen, R$^2$ is cyclohexyl, L$^2$ is CH$_2$, Cy$^2$ is phenyl, X is —C(O)NH, n is 0, p is 0, L$^1$ is CR$^7$R$^8$, and one of R$^7$ or R$^8$ is COOH and the other is hydrogen, then Cy$^1$ is not 1H-indol-5-ol-3yl;

when A is N, Y is CR$^{10}$, R$^{10}$ is hydrogen, R$^2$ is (C$_1$-C$_4$) alkyl, X is —NHC(O), L$^2$ is CH$_2$, p is 0, n is 0, L$^1$ is CR$^7$R$^8$, and both of R$^7$ and R$^8$ are hydrogen, then Cy$^1$ is not piperidinyl; and when A is N, Y is CR$^{10}$, R$^{10}$ is hydrogen, R$^2$ is methyl, Cy$^1$ is aryl, L$^2$ is CH$_2$, p is 0, X is —C(O)NH, n is 0, L$^1$ is CR$^7$R$^8$, and both of R$^7$ or R$^8$ are hydrogen, then Cy$^2$ is not phenyl substituted with CN.

2. Compounds and Definitions

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, and bromine.

The terms "cycloalkyl" and "cycloaliphatic", used alone or as part of a larger moiety, refer to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl. It will be understood that when specified, optional substituents on a cycloalkyl or cycloaliphatic group may be present on any substitutable position and, include, e.g., the position at which the cycloalkyl or cycloaliphatic group is attached.

The term "carbocycle", "carbocyclyl", "carbocyclo", or "carbocyclic" used alone or as part of a larger moiety refer to saturated, partially saturated, or aromatic ring systems comprising all carbon atoms having, unless otherwise specified, a total of 3 to 10 ring members. It will be understood that when specified, optional substituents on a carbocycle, carbocyclyl, carbocyclo, or carbocyclic may be present on any substitutable position and, include, e.g., the position at which the cycloalkyl is attached.

The term "aryl" used alone or as part of a larger moiety as in "aralkyl", "aralkoxy", or "aryloxyalkyl", refers to an aromatic carbocyclic ring system having, unless otherwise specified, a total of 6 to 10 ring members. The term "aryl" may be used interchangeably with the term "aryl ring", "aryl group", "aryl moiety," or "aryl radical". In certain embodiments of the present disclosure, "aryl" refers to an aromatic ring system which includes, but is not limited to, phenyl (abbreviated as "Ph"), naphthyl and the like. It will be understood that when specified, optional substituents on an aryl group may be present on any substitutable position and, include, e.g., the position at which the aryl is attached.

The term "heteroaryl" used alone or as part of a larger moiety as in "heteroarylalkyl", "heteroarylalkoxy", or "heteroarylaminoalkyl", refers to a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl" may be used interchangeably with the terms "heteroaryl ring", "heteroaryl group", or "heteroaromatic". The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. It will be understood that when specified, optional substituents on a heteroaryl group may be present on any substitutable position and, include, e.g., the position at which the heteroaryl is attached.

The term "heterocyclyl" means a 4-, 5-, 6- and 7-membered saturated or partially unsaturated heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. A heterocyclyl group may be mono- or bicyclic. Unless otherwise specified, bicyclic heterocyclyl groups include, e.g., unsaturated heterocyclic radicals fused to another unsaturated heterocyclic radical or aromatic or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

As used herein, a hyphen ("-") at the beginning or end of a recited group designates the point at which a recited group is attached to a defined group. For example, —SO$_2$—(C$_1$-C$_3$)alkyl-(C$_2$-C$_6$)cycloalkyl means that the group is attached via the sulfonyl.

"Racemate" or "racemic mixture" means a compound of equimolar quantities of two enantiomers, wherein such mixtures exhibit no optical activity, i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. When a disclosed compound is named or depicted by structure without indicating a particular geometric isomer form, it is to be understood that the name or structure encompasses one geometric isomer free of other geometric isomers, mixtures of geometric isomers, or all geometric isomers.

The compounds of the herein may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and e.g, the compound has at least two chiral centers, it is to be understood that the name or structure encompasses one stereoisomer free of other stereoisomers, mixtures of stereoisomers, and mixtures of stereoisomers in which one or more stereoisomers is enriched relative to the other stereoisomer(s). For example, the name or structure may encompass one stereoisomer free of other diastereomers, mixtures of stereoisomers, and mixtures of stereoisomers in which one or more diastereomers is enriched relative to the other diastereomer(s).

The compounds of the herein may be present in the form of pharmaceutically acceptable salts. For use in medicines, the salts of the compounds of the invention refer to nontoxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present disclosure provides a compound of Formula I,

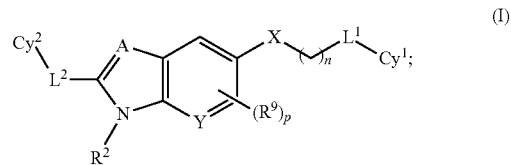

or a pharmaceutically acceptable salt thereof, wherein the variables are as described above.

In a second embodiment, the present disclosure provides a compound of Formula I,

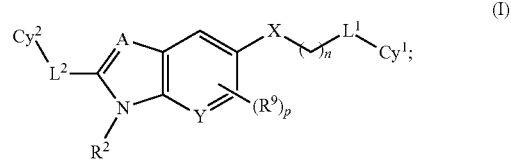

or a pharmaceutically acceptable salt thereof, wherein the variables are as described above, provided that when A is N, Y is $CR^{10}$, $R^{10}$ is hydrogen, and $R^2$ is monocyclic cycloalkyl, neither $R^7$ nor $R^8$ are $(C_1-C_3)$alkyl; and when A is N, Y is $CR^{10}$, $R^{10}$ is hydrogen, and $R^2$ is $(C_4)$alkyl, neither $R^7$ nor $R^8$ are $(C_1-C_3)$alkyl.

In a third embodiment, the compound of Formula I is of Formula II:

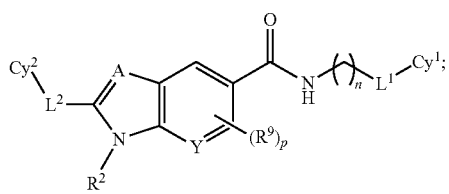

(II)

or a pharmaceutically acceptable salt thereof, wherein $R^7$ and $R^8$ are each independently hydrogen, OH, $(C_1-C_2)$alkyl, hydroxy$(C_1-C_3)$alkyl, —O$(C_1-C_3)$alkyl, —$(C_1-C_3)$alkyl-O—$(C_1-C_3)$alkyl, —$(C_1-C_3)$alkyl-NH$_2$, —$(C_1-C_3)$alkyl-N-di$(C_1-C_3)$alkyl, $(CH_2)_{1-3}$COOH, monocyclic heterocyclyl, —CO—$(C_1-C_3)$alkoxy, —$(C_1-C_3)$alkoxy-C(O)—NH$_2$, —$(C_1-C_3)$alkoxy-O—$(C_1-C_3)$alkyl-C(O)—NH$_2$, —$(C_1-C_3)$alkyl-C(O)—$(C_1-C_3)$alkoxy, —$(C_1-C_3)$alkyl-C(O)—NH$_2$, halophenyl, —$(C_1-C_3)$alkyl-halophenyl, or quinolin-2(1H)one-4yl-methyl, and wherein the variables in structural Formula II are as described for Formula I. Alternatively, the compound of Formula I is of Formula II:

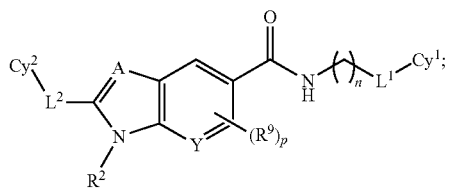

(II)

or a pharmaceutically acceptable salt thereof, wherein $R^7$ and $R^8$ are each independently hydrogen, OH, $(C_1-C_2)$alkyl, hydroxy$(C_1-C_3)$alkyl, —O$(C_1-C_3)$alkyl, —$(C_1-C_3)$alkyl-O—$(C_1-C_3)$alkyl, —$(C_1-C_3)$alkyl-NH$_2$, —$(C_1-C_3)$alkyl-N-di$(C_1-C_3)$alkyl, $(CH_2)_{1-3}$COOH, monocyclic heterocyclyl, —CO—$(C_1-C_3)$alkoxy, —$(C_1-C_3)$alkoxy-C(O)—NH$_2$, —$(C_1-C_3)$alkoxy-O—$(C_1-C_3)$alkyl-C(O)—NH$_2$, —$(C_1-C_3)$alkyl-C(O)—$(C_1-C_3)$alkoxy, —$(C_1-C_3)$alkyl-C(O)—NH$_2$, halophenyl, —$(C_1-C_3)$alkyl-halophenyl, or quinolin-2(1H)one-4yl-methyl; and p is 1, and wherein the variables in structural Formula II are as described for Formula I. In another alternative, the compound of Formula I is of Formula II:

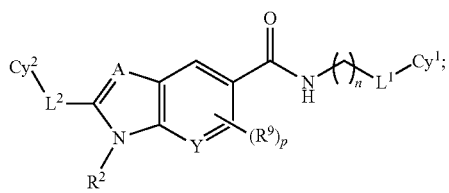

(II)

or a pharmaceutically acceptable salt thereof, wherein $R^7$ and $R^8$ are each independently hydrogen, OH, $(C_1-C_2)$alkyl, hydroxy$(C_1-C_3)$alkyl, —O$(C_1-C_3)$alkyl, —$(C_1-C_3)$alkyl-O—$(C_1-C_3)$alkyl, —$(C_1-C_3)$alkyl-NH$_2$, —$(C_1-C_3)$alkyl-N-di$(C_1-C_3)$alkyl, $(CH_2)_{1-3}$COOH, monocyclic heterocyclyl, —CO—$(C_1-C_3)$alkoxy, —$(C_1-C_3)$alkoxy-C(O)—NH$_2$, —$(C_1-C_3)$alkoxy-O—$(C_1-C_3)$alkyl-C(O)—NH$_2$, —$(C_1-C_3)$alkyl-C(O)—$(C_1-C_3)$alkoxy, —$(C_1-C_3)$alkyl-C(O)—NH$_2$, halophenyl, —$(C_1-C_3)$alkyl-halophenyl, or quinolin-2(1H)one-4yl-methyl; p is 1; and $R^9$ is $(C_1-C_4)$alkoxy or halogen, and wherein the variables in structural Formula II are as described for Formula I.

In a fourth embodiment, the compound of Formula I is of Formula IIa:

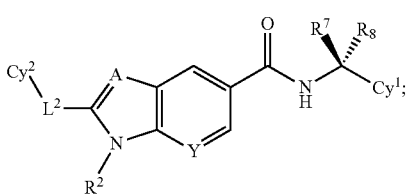

(IIa)

or a pharmaceutically acceptable salt thereof, wherein the variables in structural Formula III are as described for Formula I or the third embodiment.

In a fifth embodiment, the compound of Formula I is of Formula III:

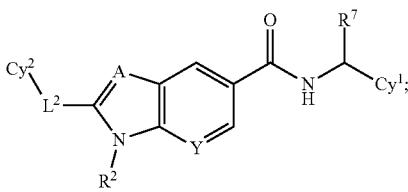

(III)

or a pharmaceutically acceptable salt thereof, wherein the variables in structural Formula III are as described for Formula I or the third embodiment.

In a sixth embodiment, the compound of Formula I is of Formula IIIa:

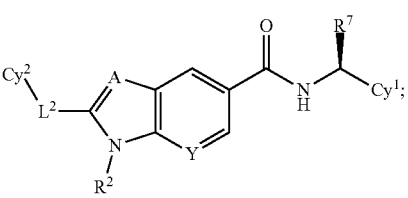

(IIIa)

or a pharmaceutically acceptable salt thereof, wherein the variables in structural Formula IIIa are as described for Formula I or the third embodiment.

In a seventh embodiment, $L^2$ in Formulas I to III is $CH_2$, CHMe, O, or C(=O), wherein the remaining variables are as described for Formula I or the third embodiment.

In an eighth embodiment, the compound of Formula I is of Formula IV, IVa, V, or Va:

or a pharmaceutically acceptable salt thereof, wherein the variables in structural Formula VI and structural Formula VII are as described for Formula I and the third or seventh embodiment.

In a tenth embodiment, $R^7$ in structural Formulae I to VII is hydrogen, $(C_1-C_2)$alkyl, hydroxy$(C_1-C_3)$alkyl, —$(C_1-C_3)$alkylNH$_2$, —$(C_1-C_3)$alkyl-N-di$(C_1-C_3)$alkyl, or —$(C_1-C_3)$alkoxy-C(O)—NH$_2$; and $R^8$ is hydrogen, wherein the remaining variables are as described for Formula I and the third or seventh embodiment. Alternatively, $R^7$ in structural Formulae I to VII is hydroxy$(C_1-C_3)$alkyl; and $R^8$ is hydrogen, wherein the remaining variables are as described for Formula I and the third or seventh embodiment.

In an eleventh embodiment, the compound of Formula I is of Formula VIII or Formula IX:

or a pharmaceutically acceptable salt thereof, wherein the variables in structural Formula (VIII) or structural Formula (IX) are as described for Formula (I) and the third, seventh or tenth embodiment.

In a twelfth embodiment, $R^2$ in Formulae I to IX is $(C_1-C_4)$alkyl or cyclopropyl, wherein the remainder of the variables are as described in Formula (I) and the third, seventh, tenth, or eleventh embodiment.

In a thirteenth embodiment, $Cy^1$ in Formulae I to IX is aryl or heteroaryl, each substituted with 1 to 3 groups independently selected from $R^5$, wherein the remainder of the variables are as described in Formula (I) and third, seventh, tenth, eleventh, or twelfth, embodiment. Alternatively, $Cy^1$ in Formulae I to IX is phenyl or pyridyl, each substituted with 1 to 3 groups independently selected from $R^5$, wherein the remainder of the variables are as described in Formula (I) and third, seventh, tenth, eleventh, or twelfth, embodiment.

In a fourteenth embodiment, $Cy^1$ in Formulae I to IX is phenyl or pyridinyl, each substituted with 1 to 3 groups independently selected from $R^5$, wherein at least one $R^5$ is —SO$_2$—$(C_1-C_3)$alkyl, wherein the remainder of the variables are as described in Formula (I) and third, seventh, tenth, eleventh, twelfth, or thirteenth embodiment. Alternatively, $Cy^1$ in Formulae I to IX is pyridinyl substituted with 1 to 3 groups independently selected from $R^5$, wherein at least one $R^5$ is $-SO_2-(C_1-C_3)$alkyl, wherein the remainder of the variables are as described in Formula (I) and the third, seventh, tenth, eleventh, twelfth, or thirteenth embodiment.

In a fifteenth embodiment, $Cy^2$ in Formulae I to IX is selected from phenyl, pyridinyl, cyclohexyl, tetrahydropyranyl, cyclopropyl, and cyclobutyl, each optionally substituted with 1 to 3 groups independently selected from $R^6$, wherein the remainder of the variables are as described in Formula (I) and the third, seventh, tenth, eleventh, twelfth, thirteenth, or fourteenth embodiment.

In a sixteenth embodiment, $Cy^2$ in Formulae I to IX is selected from phenyl, pyridinyl, piperidinyl, cyclohexyl, or tetrahydropyranyl, each optionally substituted with 1 to 3 groups independently selected from $R^6$, wherein the remainder of the variables are as described in Formula (I) and the third, seventh, tenth, eleventh, twelfth, thirteenth, fourteenth, or fifteenth embodiment.

In a seventeenth embodiment, $Cy^2$ in Formulae I to IX is selected from phenyl and cyclohexyl, each optionally substituted with 1 to 3 groups independently selected from $R^6$, wherein the remainder of the variables are as described in Formula (I) and the third, seventh, tenth, eleventh, twelfth, thirteenth, fourteenth, fifteenth, or sixteenth embodiment.

In an eighteenth embodiment, $Cy^1$ in Formulae I to IX is phenyl substituted with 1 to 3 groups independently selected from $R^5$, wherein at least one $R^5$ is $-SO_2-(C_1-C_3)$alkyl; and $Cy^2$ is cyclohexyl substituted with 1 to 3 groups independently selected from $R^6$, wherein the remainder of the variables are as described in Formula (I) and the third, seventh, tenth, eleventh, twelfth, thirteenth, fourteenth, fifteenth, sixteenth, or seventeenth embodiment.

In a nineteenth embodiment, $R^5$ in Formulae I to IX is selected from halogen, $-CN$, $-OR^c$, $-NR^dR^e$, $-NR^cS(O)_2R^c$, $-S(O)_2NR^dR^e$, $-C(=O)OR^c$, $-C(=O)NR^dR^e$, $-NR^cC(=O)R^c$, $-NR^cC(=O)OR^c$, $-OC(=S)NR^dR^e$, $-C(=O)R^c$, $-SO_2-(C_1-C_3)$alkyl, and $(C_1-C_4)$alkyl optionally substituted with halogen; and $R^6$ is selected from halogen, $-CN$, $-OR^c$, $-NR^dR^e$, $-NR^cS(O)_2R^c$, $-S(O)_2NR^dR^e$, $-C(=O)OR^c$, $-OC(=O)OR^c$, $-OC(=O)R^c$, $-C(=O)NR^dR^e$, $-NR^cC(=O)R^c$, $-C(=S)NR^dR^e$, $-NR^cC(=S)R^c$, $-NR^cC(=O)OR^c$, $-OC(=O)NR^dR^e$, $-NR^cC(=S)OR^c$, $-OC(=S)NR^dR^e$, $-NR^cC(=O)NR^dR^e$, $-NR^cC(=S)NR^dR^e$, $-C(=S)R^c$, $-C(=O)R^c$, $-SO_2-(C_1-C_3)$alkyl, and $(C_1-C_4)$alkyl optionally substituted with halogen, wherein the remainder of the variables are as described in Formula (I) and the third, seventh, tenth, eleventh, twelfth, thirteenth, fourteenth, fifteenth, sixteenth, seventeenth, or eighteenth embodiment.

In a twentieth embodiment, $R^5$ in Formulae I to IX is $-SO_2-(C_1-C_3)$alkyl; $R^6$ is selected from halo, $-OR^c$, and $(C_1-C_4)$alkyl optionally substituted with halogen and $R^c$ is $(C_1-C_4)$alkyl optionally substituted with halogen, wherein the remainder of the variables are as described in Formula (I) and the third, seventh, tenth, eleventh, twelfth, thirteenth, fourteenth, fifteenth, sixteenth, seventeenth, eighteenth, or nineteenth embodiment.

In a twenty-first embodiment, $R^6$ in Formulae I to IX is $CF_3$, wherein the remainder of the variables are as described in Formula (I) and the third, seventh, tenth, eleventh, twelfth, thirteenth, fourteenth, fifteenth, sixteenth, seventeenth, eighteenth, nineteenth, or twentieth embodiment.

Specific examples of compounds are provided in the EXEMPLIFICATION. Pharmaceutically acceptable salts as well as the neutral forms of these compounds are included herein.

In certain embodiments, the present disclosure provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present disclosure provides a method of treating a subject (e.g., a human) with a disorder mediated by RORγ using a composition comprising a compound of Formula I and a pharmaceutically acceptable carrier, adjuvant, or vehicle. In certain embodiments, the amount of compound of Formula I in a provided composition is such that it is effective as an inverse agonist or antagonist to RORγ in a biological sample or in a subject. In certain embodiments, a provided composition is formulated for administration to a subject in need of such composition. In some embodiments, a provided composition is formulated for oral administration to a subject.

The term "pharmaceutically acceptable carrier, adjuvant, or vehicle" refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope herein. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for modulating RORγ. Thus, in some embodiments, the present disclosure provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Modulation of RORγ (or to modulate RORγ), means that a change or alternation in the activity of RORγ has occurred from the administration of one or more of the compounds described herein. Modulation may be an upregulation (increase) or a downregulation (decrease) in the magnitude of the activity or function of RORγ. Exemplary activities and functions include e.g., binding characteristics, enzymatic activity, cell receptor activation, transcriptional activity, and signal transduction. In one aspect, the compounds described herein inhibit RORγ. In further aspects, the compounds described herein act as agonists, antagonists, or inverse agonists of RORγ.

In another aspect, compounds and compositions described herein are useful for reducing the amount of IL-17 in a subject. Thus, in some embodiments, provided herein are methods of reducing the amount of IL-17 in a subject comprising administering an effective amount of a provided compound or composition. RORγ modulators disclosed in WO 2014/179564, WO 2015/116904, WO 2016/061160 and U.S. patent application Ser. Nos. 14/933,468 and 14/933,524 can also be used in such methods.

In another aspect, compounds and compositions described herein are useful for inhibiting the synthesis IL-17 in a subject. Thus, in some embodiments, provided herein are methods of inhibiting the synthesis of IL-17 is a subject comprising administering an effective amount of a provided compound or composition. RORγ modulators disclosed in WO 2014/179564, WO 2015/116904, WO 2016/061160 and U.S. patent application Ser. Nos. 14/933,468 and 14/933,524 can also be used in such methods.

Diseases and conditions treatable according to the methods herein include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to lung cancer, gastric cancer, breast cancer and colon cancer. In one aspect, an exemplified form of cancer treatable according to the methods herein also includes prostate cancer e.g., (metastatic castration-resistant prostate cancer tumors). In another aspect, an exemplified form of cancer treatable according to the methods herein includes e.g., malignant tumor, angiogenesis glaucoma, infantile hemangioma, multiple myeloma, acute myeloblastic leukemia, chronic sarcoma, chronic myelogenous leukemia, metastasis melanoma, Kaposi's sacroma, vascular proliferation, cachexia, colorectal cancer (e.g., familial colorectal cancer, hereditary nonpolyposis colorectal cancer, and gastrointestinal stromal tumor), lung cancer (e.g., non-small cell lung cancer, small cell lung cancer and malignant mesothelioma), mesothelioma, pancreatic cancer (e.g., pancreatic duct cancer), gastric cancer (e.g., papillary adenocarcinoma, mucinous adenocarcinoma and adenosquamous carcinoma), breast cancer (e.g., invasive ductal carcinoma, ductal carcinoma in situ, inflammatory breast cancer and metastatic breast cancer), ovarian cancer (e.g., ovarian epithelial carcinoma, extragonadal germ cell tumor, ovarian germ cell tumor, and ovarian low malignant potential tumor), hormone-dependent prostate cancer, non-hormone dependent prostate cancer, liver cancer (e.g., primary liver cancer and extrahepatic bile duct cancer), thyroid cancer (e.g., medullary thyroid carcinoma), kidney cancer (e.g., renal cell carcinoma, and transitional cell carcinoma in kidney and urinary duct), uterine cancer, endometrial cancer, brain tumor (e.g., pineal astrocytoma, pilocytic astrocytoma, diffuse astrocytoma and anaplastic astrocytoma), melanoma, sarcoma, urinary bladder cancer, hematologic cancer, hypophyseal adenoma, glioma, acoustic neurinoma, retinoblastoma, head and neck cancer, head and neck squamous cell carcinoma, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervical cancer, endometrial cancer, uterus sarcoma, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, chronic myelocytic leukemia, malignant myeloma, adult T cell leukemia, chronic bone marrow proliferative disease, pancreatic endocrine tumor, fibrous histiocytoma, leiomyosarcoma, rhabdomyosarcoma, cancer of unknown primary, cancer-driven myelopoiesis, tumor growth, and metastasis.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's disease and other central nervous system (CNS) disorders associated with altered sleep and/or circadian rhythms.

Also included in the diseases and disorders treatable by the compounds described herein are diseases and disorders mediated by IL-17 expression, including STAT3-mediated IL-17 expression, in neutrophils, and include, e.g., corneal fungal infection; risk of corneal fungal infection; corneal ulcer; corneal ulcer resulting from fungal keratitis; corneal ulcer resulting from fungal infection; corneal fungal infection and related inflammation; keratitis; fungal keratitis; corneal inflammation; corneal disease; ocular disease; fungal-mediated corneal infection, corneal ulcer, corneal inflammation, or ocular ulcer, inflammation or infection; bacterial-mediated corneal infection, corneal ulcer, corneal inflammation, or ocular ulcer, inflammation or infection; microbial disease; bacterial infections; fungal infections; *Aspergillus* keratitis; *Fusarium* keratitis; cutaneous T cell lymphoma; lung inflammation; acute kidney ischemia-reperfusion injury; anthrax, including, cutaneous anthrax, inhalation anthrax, gastrointestinal anthrax and injection anthrax; aspergillosis, including, pulmonary aspergillosis, chronic pulmonary aspergillosis (CPA), chronic aspergillosis, chronic cavitary pulmonary aspergillosis (CCPA), allergic bronchopulmonary aspergillosis (ABPA), allergic *Aspergillus* sinusitis, aspergilloma, invasive aspergillosis, chronic necrotizing aspergillosis and cutaneous (skin) aspergillosis; and histoplasmosis, including, systemic histoplasmosis. In particular embodiments, the fungus or fungal infection meditating the disease or disorder described above includes one or more of *Aspergillus, Fusarium, Alternaria, Candida, Curvularia* or *Histoplasma*.

Diseases and disorders mediated by IL-17 expression, and which are treatable using the compounds described herein also include e.g., chronic graft-versus-host disease, acute graft-versus-host disease, celiac sprue, emphysema, lung fibrosis, giant cell arteritis, arteriosclerosis, hepatitis, chronic active hepatitis, alcoholic hepatitis, alcoholic liver fibrosis, alcoholic cirrhosis, viral hepatitis, hepatitis B viral liver disorder, autoimmune hepatitis, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, spondyloarthritis, juvenile ankylosing spondylitis, juvenile enteropathic arthritis, juvenile reactive arthritis, juvenile Reiter's syndrome, seronegative enthesopathy and arthropathy (SEA) syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reiter's syndrome, vasculitis, myositis, polymyositis, autoimmune myositis, osteoarthritis, polyarteritis nodossa, arteritis, polymyalgia rheumatica, sclerosis, primary biliary sclerosis, sclerosing cholangitis, enthesitis, enthesopathy, dermatitis, atopic eczema, eczema, atherosclerosis, Still's disease, Addison's disease, Raynaud's phenomenon, psoriatic epidermal hyperplasia, plaque psoriasis, guttate psoriasis, inverse psoriasis, pustular psoriasis, erythrodermic psoriasis, giant cell arteritis, noninfectious uveitis, Vogt-Koyanagi-Harada syndrome, mucosal leishmaniasis, Kawasaki disease, Hashimoto's thyroiditis, immune thrombocytopenic purpura (also known as immune thrombocytopenia, idiopathic immune thrombocytopenia, idiopathic thrombocytopenic thrombotic purpura, primary immune thrombocytopenia, idiopathic thrombocytopenic purpura, primary immune thrombocytopenic purpura, or autoimmune thrombocytopenic purpura), kidney inflammation, interstitial kidney inflammation, kidney disease, chronic kidney disease, renal failure, acute renal failure, end stage kidney disease, acute kidney injury, cisplatin induced acute renal failure, sepsis induced acute renal failure, nephritis, nephrotoxic nephritis, glomerulonephritis, acute glomerulonephritis, antineutrophil cytoplasmic autoantibody (ANCA) associated vasculitis, microscopic polyangiitis, granulomatosis with polyangiitis, Wegener's granulomatosis, amyotrophic lateral sclerosis, lupus nephritis, allergic eczema, transplant rejection, non-radiographic spondyloarthropathy, ophthalmic disorders, organ allograft rejection, fibroid lung, renal insufficiency, diabetic complications, diabetic nephropathy, diabetic retinopathy, diabetic retinitis, diabetic microangiopathy, insulitis, tuberculosis, invasive staphylococcia, invasive *Staphylococcus aureus* infection, inflammation after cataract surgery, allergic conjunctivitis, urticaria, chronic urticaria, allergic asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, acute pancreatitis, chronic pancreatitis, asthma, bronchial asthma, acute respiratory distress syndrome, adult respiratory distress syndrome, inflammatory bone disease, inflammatory pulmonary disease, ischemic attack, transient ischemic attack, systemic inflammatory response syndrome, glaucoma, orbital cellulitis, sudden orbital inflammation, postoperative inflammation, posttraumatic inflammation, allergic inflammation, intestinal inflammation, mucosal inflammation, prostate inflammation, prostatitis, chronic pelvic pain syndrome, testicular inflammation, chronic testicular inflammation, orchitis, orchitis mediated infertility, liver disorder, liver injury, hepatoxicity, pneumonia, meningitis, cystitis, pharyngolaryngitis, gastric mucosal injury, chronic pneumonia, pulmonary infarction, silicosis, pulmonary sarcoidosis, autoimmune anemia, autoimmune hemolytic anemia, Goodpasture's syndrome, sinusitis, chronic hypertrophic rhinitis, chronic inflammatory demyelinating polyneuropathy, mixed connective tissue disease, cognitive impairment, cognitive impairment in Alzheimer's disease, Parkinson's disease, spinal muscular atrophy, spinal cerebellar atrophy, progressive supranuclear palsy, Fisher syndrome, central nervous system lupus, encephalomyelitis, acute disseminated encephalomyelitis, multiple system atrophy, Huntington's disease, cerebrovascular dementia, diffuse Lewy body disease, cerebrovascular disorder, cerebral infarction, transient ischemic attack, intracerebral hemorrhage, vascular disease of the spinal cord, spinal cord infarction, Lambert-Eaton syndrome, muscular dystrophy, metabolic myopathy, inflammatory myopathy, inclusion body myositis, encephalitis, pemphigus, pemphigus vulgaris, profundus lupus erythematosus, chronic thyroiditis, autoimmune gastritis, sepsis, burn injury, pain, neuropathy, chronic pain, optic neuropathy, traumatic optic neuropathy, ischemic brain injury, deep venous thrombosis, autoimmune hemolytic anemia, autoimmune neutropenia, thrombocytopenia, abnormal immunoresponse, radiodermatitis, osteoporosis, parasitic infection, clonorchiasis, *Cryptosporidium* infection, *Streptococcus pneumoniae* carriage, chronic pneumococcal carriage, and an immune disorder associated with or arising from activity of pathogenic lymphocytes.

In one embodiment, a human patient is treated with a compound of Formula I and a pharmaceutically acceptable carrier, adjuvant, or vehicle, wherein said compound is present in an amount to treat or ameliorate one or more of the diseases and conditions recited above. In an alternative embodiment, the diseases and conditions treated or ameliorated by a compound of Formula I include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus (SLE), scleroderma, psoriasis, psoriatic arthritis (PsA), steroid resistant asthma and rheumatoid arthritis in the patient.

The present disclosure further relates to a combination therapy for treating or ameliorating a disease or a disorder described herein. In some embodiments, the combination therapy comprises administering at least one compound represented by Structural Formula I in combination with one or more agents for treating or ameliorating inflammatory, metabolic and autoimmune diseases or disorders mediated by RORγ. In some embodiments, the combination therapy comprises administering at least one compound represented by Structural Formula I in combination with one or more agents for the treatment of diseases including asthma, chronic obstructive pulmonary disease (COPD), bronchitis, allergic rhinitis, atopic dermatitis, contact dermatitis, acne, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to, lung cancer, gastric cancer, breast cancer and colon cancer.

The compounds herein may also be used in combination with immunotherapies for the treatment of a disease or disorder disclosed herein.

Combination therapy includes, e.g., co-administration of a compound described herein and one or more other agents, sequential administration of a compound of the described and one or more other agents, administration of a composition containing a compound herein and one or more other agents, or simultaneous administration of separate compositions containing a compound described herein and one or more other agents.

The present disclosure further provides a method of treating a subject, such as a human, suffering from one of the abovementioned disorders or diseases.

In one aspect, RORγ modulators disclosed in WO 2014/179564, WO 2015/116904, WO 2016/061160 and U.S. patent application publication Nos. U.S. 2016/0122318 and U.S. 2016/0122345 can also be used in the methods disclosed herein to treat or ameliorate, in a subject, one or more of the diseases and/or disorders and/or conditions recited herein. In one embodiment, a subject is treated with one or more RORγ modulators disclosed in WO 2014/179564, WO 2015/116904, WO 2016/061160 and U.S. patent application publication Nos. U.S. 2016/0122318 and U.S. 2016/0122345 and a pharmaceutically acceptable carrier, adjuvant, or vehicle, wherein said RORγ modulator is present in an amount to treat or ameliorate a disease or disorder selected from corneal fungal infection; risk of corneal fungal infection; corneal ulcer; corneal ulcer resulting from fungal keratitis; corneal ulcer resulting from fungal infection; corneal fungal infection and related inflammation; keratitis; fungal keratitis; corneal inflammation; corneal disease; ocular disease; fungal-mediated corneal infection, corneal ulcer, corneal inflammation, or ocular ulcer, inflammation or infection; bacterial-mediated corneal infection, corneal ulcer, corneal inflammation, or ocular ulcer, inflammation or infection; microbial disease; bacterial infections; fungal infections; *Aspergillus* keratitis; *Fusarium* keratitis; cutaneous T cell lymphoma; lung inflammation; acute kidney ischemia-reperfusion injury; anthrax, including, cutaneous anthrax, inhalation anthrax, gastrointestinal anthrax and injection anthrax; aspergillosis, including, pulmonary aspergillosis, chronic pulmonary aspergillosis (CPA), chronic aspergillosis, chronic cavitary pulmonary aspergillosis (CCPA), allergic bronchopulmonary aspergillosis (ABPA), allergic *Aspergillus* sinusitis, aspergilloma, invasive aspergillosis, chronic necrotizing aspergillosis and cutaneous (skin) aspergillosis; histoplasmosis, including, systemic histoplasmosis; and prostate cancer.

In an alternative, a subject is treated with one or more RORγ modulators disclosed in WO 2014/179564, WO 2015/116904, WO 2016/061160 and U.S. patent application publication Nos. U.S. 2016/0122318 and U.S. 2016/0122345 and a pharmaceutically acceptable carrier, adjuvant, or vehicle, wherein said RORγ modulator is present in an amount to treat or ameliorate a disease or disorder selected from chronic graft-versus-host disease, acute graft-versus-host disease, celiac sprue, emphysema, lung fibrosis, giant cell arteritis, arteriosclerosis, hepatitis, chronic active hepatitis, alcoholic hepatitis, alcoholic liver fibrosis, alcoholic cirrhosis, viral hepatitis, hepatitis B viral liver disorder, autoimmune hepatitis, epidermal hyperplasia, cartilage inflammation, bone degradation, juvenile arthritis, juvenile rheumatoid arthritis, pauciarticular juvenile rheumatoid arthritis, polyarticular juvenile rheumatoid arthritis, systemic onset juvenile rheumatoid arthritis, spondyloarthritis, juvenile ankylosing spondylitis, juvenile enteropathic arthritis, juvenile reactive arthritis, juvenile Reiter's syndrome, seronegative enthesopathy and arthropathy (SEA) syndrome, juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, enteropathic arthritis, reactive arthritis, Reiter's syndrome, vasculitis, myositis, polymyositis, autoimmune myositis, osteoarthritis, polyarteritis nodossa, arteritis, polymyalgia rheumatica, sclerosis, primary biliary sclerosis, sclerosing cholangitis, enthesitis, enthesopathy, dermatitis, atopic eczema, eczema, atherosclerosis, Still's disease, Addison's disease, Raynaud's phenomenon, psoriatic epidermal hyperplasia, plaque psoriasis, guttate psoriasis, inverse psoriasis, pustular psoriasis, erythrodermic psoriasis, giant cell arteritis, noninfectious uveitis, Vogt-Koyanagi-Harada syndrome, mucosal leishmaniasis, Kawasaki disease, Hashimoto's thyroiditis, immune thrombocytopenic purpura (also known as immune thrombocytopenia, idiopathic immune thrombocytopenia, idiopathic thrombocytopenic thrombotic purpura, primary immune thrombocytopenia, idiopathic thrombocytopenic purpura, primary immune thrombocytopenic purpura, or autoimmune thrombocytopenic purpura), kidney inflammation, interstitial kidney inflammation, kidney disease, chronic kidney disease, renal failure, acute renal failure, end stage kidney disease, acute kidney injury, cisplatin induced acute renal failure, sepsis induced acute renal failure, nephritis, nephrotoxic nephritis, glomerulonephritis, acute glomerulonephritis, antineutrophil cytoplasmic autoantibody (ANCA) associated vasculitis, microscopic polyangiitis, granulomatosis with polyangiitis, Wegener's granulomatosis, amyotrophic lateral sclerosis, lupus nephritis, allergic eczema, transplant rejection, non-radiographic spondyloarthropathy, ophthalmic disorders, organ allograft rejection, fibroid lung, renal insufficiency, diabetic complications, diabetic nephropathy, diabetic retinopathy, diabetic retinitis, diabetic microangiopathy, insulitis, tuberculosis, invasive staphylococcia, invasive *Staphylococcus aureus* infection, inflammation after cataract surgery, allergic conjunctivitis, urticaria, chronic urticaria, allergic asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, acute pancreatitis, chronic pancreatitis, asthma, bronchial asthma, acute respiratory distress syndrome, adult respiratory distress syndrome, inflammatory bone disease, inflammatory pulmonary disease, ischemic attack, transient ischemic attack, systemic inflammatory response syndrome, glaucoma, orbital cellulitis, sudden orbital inflammation, postoperative inflammation, posttraumatic inflammation, allergic inflammation, intestinal inflammation, mucosal inflammation, prostate inflammation, prostatitis, chronic pelvic pain syndrome, testicular inflammation, chronic testicular inflammation, orchitis, orchitis mediated infertility, liver disorder, liver injury, hepatoxicity, pneumonia, meningitis, cystitis, pharyngolaryngitis, gastric mucosal injury, chronic pneumonia, pulmonary infarction, silicosis, pulmonary sarcoidosis, autoimmune anemia, autoimmune hemolytic anemia, Goodpasture's syndrome, sinusitis, chronic hypertrophic rhinitis, chronic inflammatory demyelinating polyneuropathy, mixed connective tissue disease, cognitive impairment, cognitive impairment in Alzheimer's disease, Parkinson's disease, spinal muscular atrophy, spinal cerebellar atrophy, progressive supranuclear palsy, Fisher syndrome, central nervous system lupus, encephalomyelitis, acute disseminated encephalomyelitis, multiple system atrophy, Huntington's disease, cerebrovascular dementia, diffuse Lewy body disease, cerebrovascular disorder, cerebral infarction, transient ischemic attack, intracerebral hemorrhage, vascular disease of the spinal cord, spinal cord infarction, Lambert-Eaton syndrome, muscular dystrophy, metabolic myopathy, inflammatory myopathy, inclusion body myositis, encephalitis, pemphigus, pemphigus vulgaris, *profundus* lupus erythematosus, chronic thyroiditis, autoimmune gastritis, sepsis, burn injury, pain, neuropathy, chronic pain, optic neuropathy, traumatic optic neuropathy, ischemic brain injury, deep venous thrombosis, autoimmune hemolytic anemia, autoimmune neutropenia, thrombocytopenia, abnormal immunoresponse, radiodermatitis, osteoporosis, parasitic infection, clonorchiasis, *Cryptosporidium* infection, *Streptococcus pneumoniae* carriage, chronic pneumococcal carriage, and an immune disorder associated with or arising from activity of pathogenic lymphocytes.

In some embodiments, the one or more RORγ modulator disclosed in WO 2014/179564, WO 2015/116904, WO 2016/061160 and U.S. patent application publication Nos. U.S. 2016/0122318 and U.S. 2016/0122345 is administered in combination with one or more additional agent for treating the disease or disorder.

The present disclosure further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds herein, the following general methods, and other methods known to one of ordinary skill in the art, can be applied to all compounds and subclasses and species of each of these compounds, as described herein.

General Description of Synthesis

The compounds described herein can be readily prepared according to the following reaction schemes and examples, or modifications thereof, using readily available starting materials, reagents and conventional synthesis procedures. Many of the reactions can also be carried out under microwave (MW) conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds described herein will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, $2^{nd}$ edition, John Wiley & Sons, 1991, and Richard Larock, Comprehensive Organic Transformations, $4^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The invention is illustrated by way of the following examples, in which the following abbreviations may be employed.

| Abbreviation | Meaning |
| --- | --- |
| ACN, MeCN, $CH_3CN$ | acetonitrile |
| AIBN | azobisisobutyronitrile |
| aq | aqueous |
| Boc | tert-butoxycarbonyl or t-butoxycarbonyl |
| brine | saturated aqueous NaCl |
| c-Bu | cyclobutyl |
| Cbz | benzyloxy carbonyl |
| $CeCl_3$ | ceric chloride |
| $Cs_2CO_3$ | cesium carbonate |
| CuI | cuprous iodide |
| c-Pr | cyclopropyl |
| DCM or $CH_2Cl_2$ | methylene chloride |
| DIEA | diisopropyl ethyl amine |
| DMF | dimethyl formamide |
| $DMS/Me_2S$ | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |
| $Et_2O$ | ethyl ether |
| $Et_3SiH$ | triethylsilane |
| $Et_3N$ | triethylamine |
| EtOAc, EA, AcOEt | ethyl acetate |
| EtOH | ethanol |
| $FeCl_3$ | ferric chloride |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |
| HCl | hydrochloric acid |
| $H_2O$ | water |
| $H_2O_2$ | hydrogen peroxide |
| HPLC | high performance liquid chromatography |
| i-BuOCOCl | iso-butoxycarbonyl chloride |
| ICl | iodochloride |
| $K_2CO_3$ | potassium carbonate |
| $K_3PO_4$ | tripotassium phosphate |
| LC-MS | liquid chromatography-mass spectrometry |
| LDA | lithium diiisopropylamide |
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| $MgSO_4$ | magnesium sulfate (anhydrous) |
| min | minute(s) |
| mL | milliliters |
| mmol | millimoles |
| mp, m.p. | melting point |
| MS | mass spectrometry |
| MW, uwave | microwave |
| $NaBH_4$ | sodium borohydride |
| $NaBH_3CN$ | sodium cyanoborohydride |
| NaH | sodium hydride |
| $NaHCO_3$ | sodium bicarbonate |
| NaOH | sodium hydroxide |
| NaOMe | sodium methoxide |
| $Na_2S_2O_3$ | sodium thiosulfate |
| $Na_2S_2O_5$ | sodium dithionate |
| $Na_2SO_4$ | sodium sulfate |
| $NH_4OH$ | ammonium hydroxide |
| $(NH_4)_2CO_3$ | ammonium carbonate |
| $NH_4Cl$ | ammonium chloride |
| $Na_2CO_3$ | sodium carbonate |
| $NaHCO_3$ | sodium bicarbonate |
| NaH | sodium hydride |
| NBS | N-bromosuccinimide |
| n-BuLi | n-butyllithium |
| NMM | N-methyl-morpholine |
| NMP | N-methyl-pyrrolidin-2-one |
| OTf | trifluoromethanesulfonate |
| OTs | tosylate |

-continued

| Abbreviation | Meaning |
|---|---|
| $PdCl_2dppf$ | [1,1-bis(diphenylphosphino)ferrocene]dichloropalladium(ii) |
| $Pd_2(dba)_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| $Ti(OEt)_4$ | titanium tetra ethoxide |
| Zn | zinc |
| $Zn(CN)_2$ | zinc cyanide |

LCMS Methods

Method 1

| HPLC System: | Waters ACQUITY |
|---|---|
| Column: | Waters ACQUITY CSH ™ C18 1.7 uM |
| Guard column: | Waters Assy. Frit, 0.2uM, 2.1 mm. |
| Column tem: | 40° C. |
| Mobile Phase: | A: TFA:Water (1:1000, v:v) |
|  | B: TFA:ACN (1:1000, v:v) |

| | Time (min) | B % |
|---|---|---|
| Gradient Program: | 0 | 5 |
| | 1.9 | 95 |
| | 2.20 | 95 |
| | 2.21 | 5 |

| Flow Rate: | 0.65 mL/min |
|---|---|
| Mass Spectrometer Parameters | |
| Mass Spectrometer | Waters SQD |
| Ionization | Positive Electrospray Ionization (ESI) |
| Mode | Scan (100-1400 m/z in every 0.2 second) |
| ES Capilary Voltage: | 3.5 kv |
| ES Cone Voltage: | 25 v |
| Source Temperature | 120° C. |
| Disolvation Temperature: | 500° C. |
| Desolvation Gas Flow: | Nitrogen Setting 650 (L/hr) |
| Cone Gas Flow: | Nitrogen Setting 50 (L/hr) |

Method 2

5-95AB_1.5MIN

| Column | MERCK,RP-18e 25-2 mm |
|---|---|
| | A: water (4 L) + TFA (1.5 mL) |
| | B: acetonitrile (4 L) + TFA (0.75 mL) |

| | TIME (min) | B % |
|---|---|---|
| Mobile Phase | 0 | 5 |
| | 0.7 | 95 |
| | 1.1 | 95 |
| | 1.11 | 5 |
| | 1.5 | 5 |

| Flow Rate | 1.5 mL/min |
|---|---|
| wavelength | UV 220 nm |
| Oven Temp | 50° C. |
| MS ionization | ESI |

Method 3

10-80CD_3MIN

| Column | Xbrige Shield RP-18.5um, 2.1 * 50 mm |
|---|---|
| | A: water (1 L) + NH3H2O (0.5 mL) |
| | B: acetonitrile |

| | TIME (min) | B % |
|---|---|---|
| Mobile Phase | 0 | 10 |
| | 2 | 80 |
| | 2.48 | 80 |
| | 2.49 | 10 |
| | 3 | 10 |

| Flow Rate | 1.0 mL/min |
|---|---|
| wavelength | UV 220 nm&254 nm |
| Oven Temp | 30° C. |
| MS ionization | ESI |

Method 4

10-80AB_2MIN

| Column | Xtimate C18 2.1 * 30 mm, 3 um |
|---|---|
| | A: water (4 L) + TFA (1.5 mL) |
| | B: acetonitrile (4 L) + TFA (0.75 mL) |

| | TIME (min) | B % |
|---|---|---|
| Mobile Phase | 0 | 10 |
| | 0.9 | 80 |
| | 1.5 | 80 |
| | 1.51 | 10 |
| | 2 | 10 |

| Flow Rate | 1.2 mL/min |
|---|---|
| wavelength | UV 220 nm |
| Oven Temp | 50° C. |
| MS ionization | ESI |

In a first process, a compound of Formula I, wherein X═CONH, is prepared from a carboxylic acid of Formula 100 and an amine of Formula 105, using peptide bond formation reagents such as EDC, HOBt or HATU.

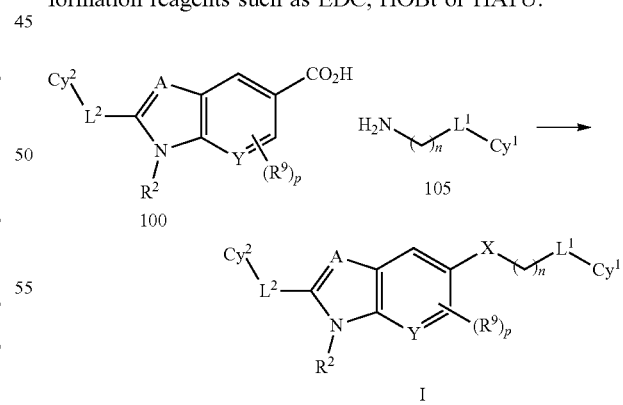

In a second process, a compound of Formula I, wherein X═CONH, is prepared from a compound of Formula 110, wherein $R^{100}$ is iodine, bromine, chlorine or trifluoromethanesulfonyloxy, carbon monoxide and an amine of Formula 105. The reaction is carried out in the presence of a palladium catalyst.

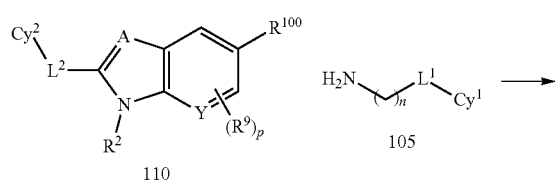

110 + 105 →

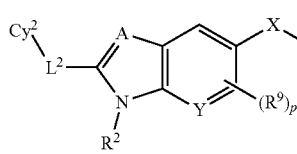

I

In a third process, a compound of Formula I, wherein X=NHCO, is prepared from an amine of Formula 115 and a carboxylic acid of Formula 120, using peptide bond formation reagents such as EDC, HOBt or HATU. Alternatively, the carboxylic acid 120 may be converted to it acid chloride prior to reaction.

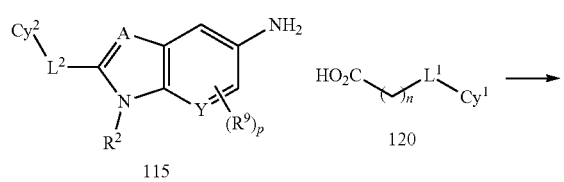

115 + 120 →

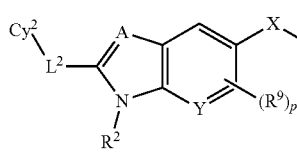

I

In a fourth process, an amine of Formula 4 is prepared from a compound of Formula 110 using NaN$_3$ in the presence of CuI or benzophenone imine in the presence of a palladium catalyst.

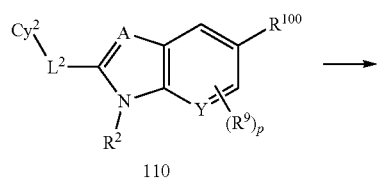

110 →

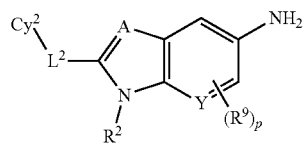

115

In a fifth process, a compound of Formula I is prepared from another compound of Formula I. For example a compound of Formula I, wherein L$^2$ is CH$_2$ or CHOH, is oxidized to a compound of Formula I, wherein L$^2$ is C=O, using, for example MnO$_2$.

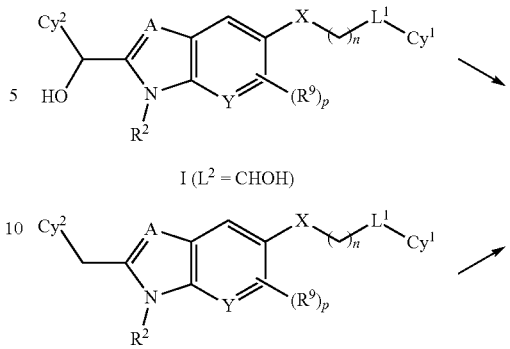

I (L$^2$ = CHOH) →

I (L$^2$ = CH$_2$) →

I (L$^2$ = CO)

In an alternative, a compound of Formula I, wherein L$^2$=CO, is reduced to a compound of Formula I, wherein L$^2$=CHOH, using, for example NaBH$_4$.

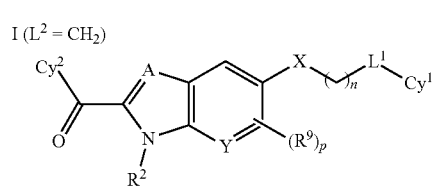

I (L$^2$ = CO) →

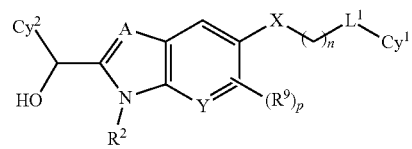

I (L$^2$ = CHOH)

In an alternative, a compound of Formula I, wherein R$^7$ (or R$^8$) is CH$_2$OH is derivatized to provide a compound of Formula I, wherein R$^7$ (or R$^8$) is CH$_2$OC(=O)NH$_2$ by the action of Cl$_3$CC(=O)NCO, followed by K$_2$CO$_3$ in MeOH.

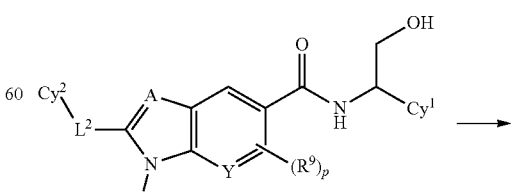

I (L$^7$ = CH$_2$OH) →

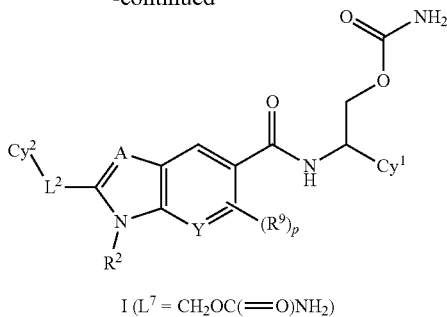

I ($L^7$ = $CH_2OC(=O)NH_2$)

In another alternative, a compound of Formula I, wherein $R^6$ (or $R^5$) is $CONH_2$, is treated with trifluoroacetic anhydride in the presence of a base such as $Et_3N$ or pyridine, to provide a compound of Formula I wherein $R^6$ (or $R^5$) is CN.

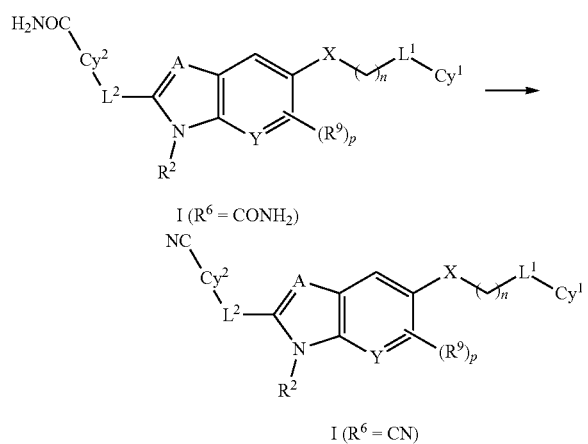

In a sixth process, a compound of Formula I, wherein A is N, is prepared from a compound of Formula 125 by treatment with acid, for example heating in HOAc at 100° C.

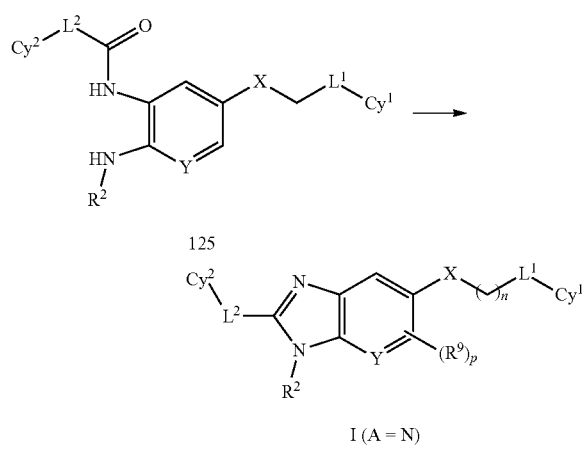

In a seventh process, a compound of Formula 125 is prepared by $S_NAr$ reaction, or Buchwald-Hartwig coupling, of an ortho halo nitro compound of Formula 7, wherein Hal=F, Cl, Br or I, with an amine of Formula 135 to give a compound of Formula 140. Reduction of 140, using for example zinc dust in the presence of $NH_4Cl$, water and THF, gives a diamine of Formula 145. Acylation of 145 with acids of Formula 150, mediated by peptide coupling reagents such as HATU, gives compounds of Formula 125. Alternatively, the acid chloride of 150 can be employed in the final step.

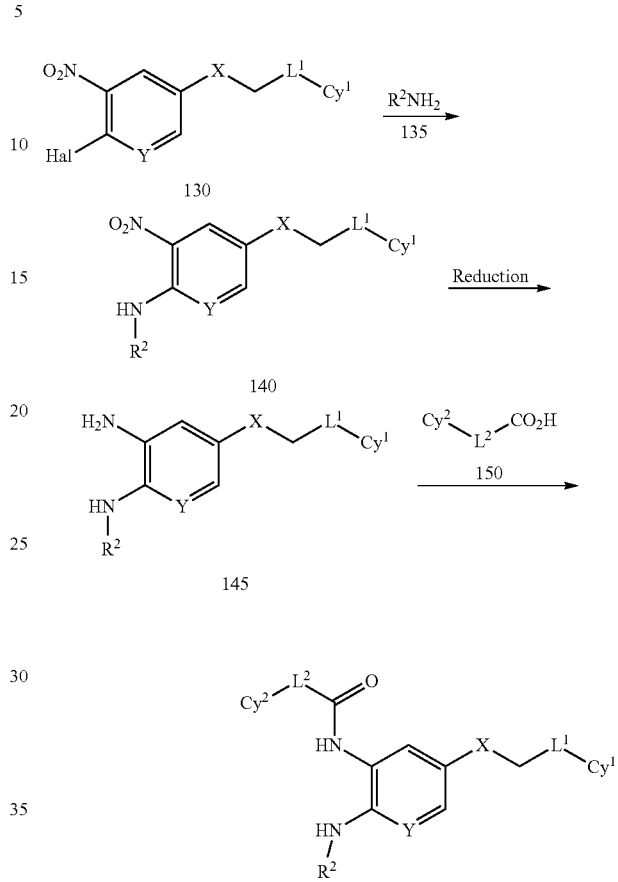

In an eighth process, a carboxylic acid of Formula 100 is prepared as follows. A compound of Formula 160 is prepared by $S_NAr$ reaction, or Buchwald-Hartwig coupling, of an ortho halo nitro compound of Formula 155, wherein Hal is F, Cl, Br or I and $R^{101}$ is lower alkyl, with an amine of Formula 135 to give an ortho amino nitro compound of Formula 160. Reduction of 160, using for example zinc dust in the presence of $NH_4Cl$ or hydrogen in the presence of palladium on carbon, gives a diamine of Formula 165. Acylation of 165 with acids of Formula 150, mediated by peptide coupling reagents such as HATU, gives amide compounds of Formula 170. Alternatively, the acid chloride of 150 can be employed in this step. Treatment of 170 with acids, for example HOAc at 100° C. or TFA at room temperature affords compounds of Formula 175 Finally the ester moiety in 175 is hydrolyzed with MOH, wherein M=an alkali metal, to afford carboxylic acids of Formula 100.

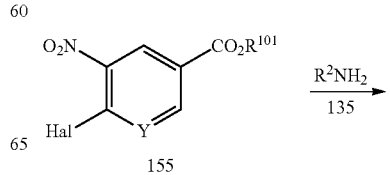

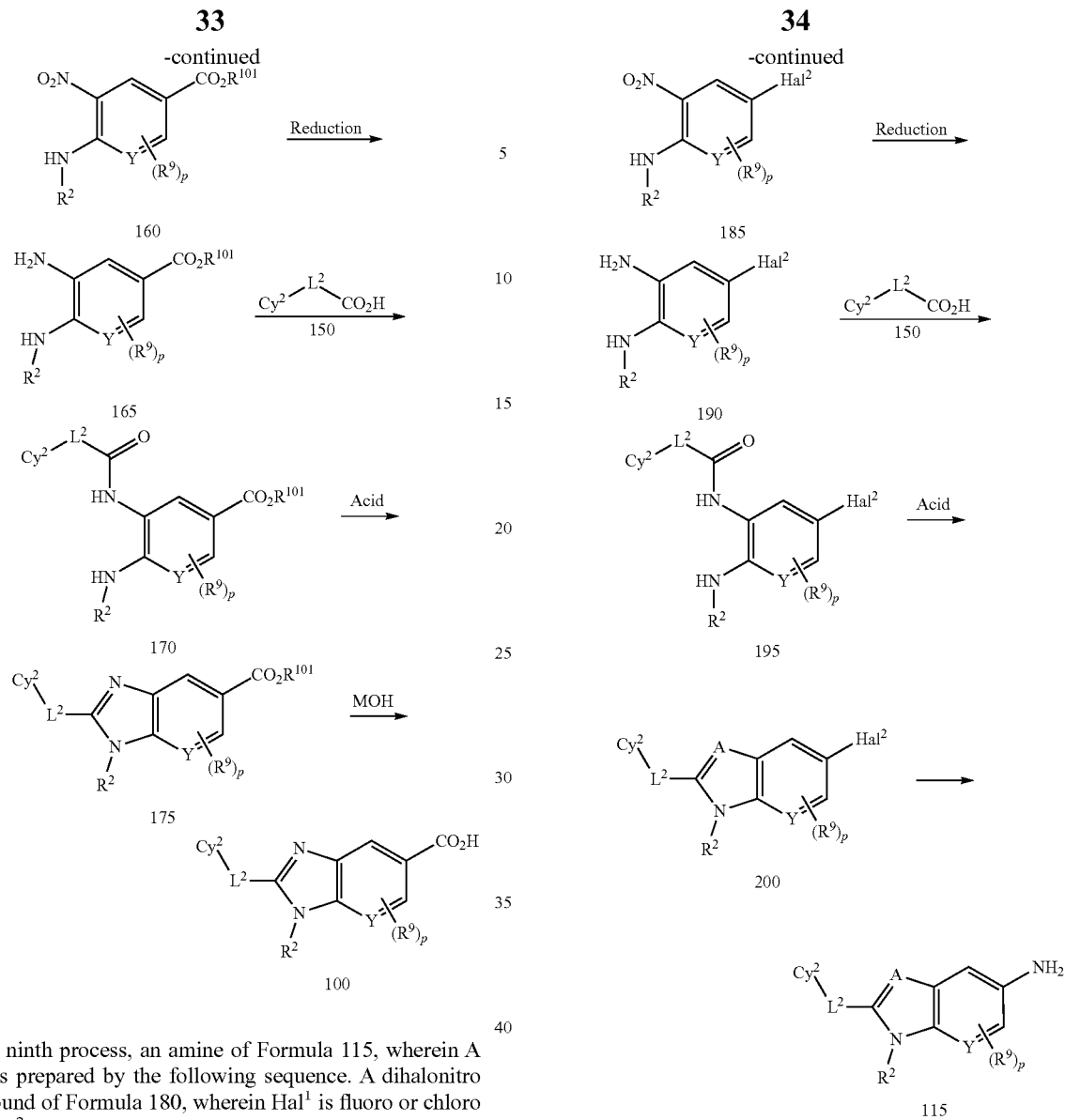

In a ninth process, an amine of Formula 115, wherein A is N, is prepared by the following sequence. A dihalonitro compound of Formula 180, wherein Hal¹ is fluoro or chloro and Hal² is bromo or iodo, is reacted with an amine of Formula 135 under $S_NAr$ reaction conditions, for example i-PrzNEt in MeCN, to give a compound of Formula 185. The nitro group in 185 is selectively reduced using for example $SnCl_2$ in EtOH or DMF, to afford a diamine of Formula 190. Acylation of 190 with acids of Formula 150, mediated by peptide coupling reagents such as HATU, gives amide compounds of Formula 20. Alternatively, the acid chloride of 150 can be employed in this step. Treatment of 195 with acids, for example HOAc at 100° C. or TFA at room temperature, affords compounds of Formula 200 Finally, Hal² in 200 is converted to an amino group using, for example, $NaN_3$ in the presence of CuI or benzophenone imine in the presence of a palladium source and a suitable ligand to give a compound of Formula 115.

In a tenth process, a carboxylic acid of Formula 100, wherein A is CH and $R^{101}$ is lower alkyl, is prepared as follows. A halo benzene or pyridine of Formula 205, wherein Hal² is bromine or iodine, is coupled to a terminal alkyne of Formula 210 under Sonogashira conditions e.g. $PdCl_2(PPh_3)_2$, CuI, $Et_3N$, to give a compound of Formula 215. Treatment of 215 with a non nucleophilic base such as NaH effects ring closure to afford an indole or azaindole of Formula 220. Finally, the ester moiety in 220 is hydrolyzed with MOH, wherein M=an alkali metal, to afford a carboxylic acid of Formula 100.

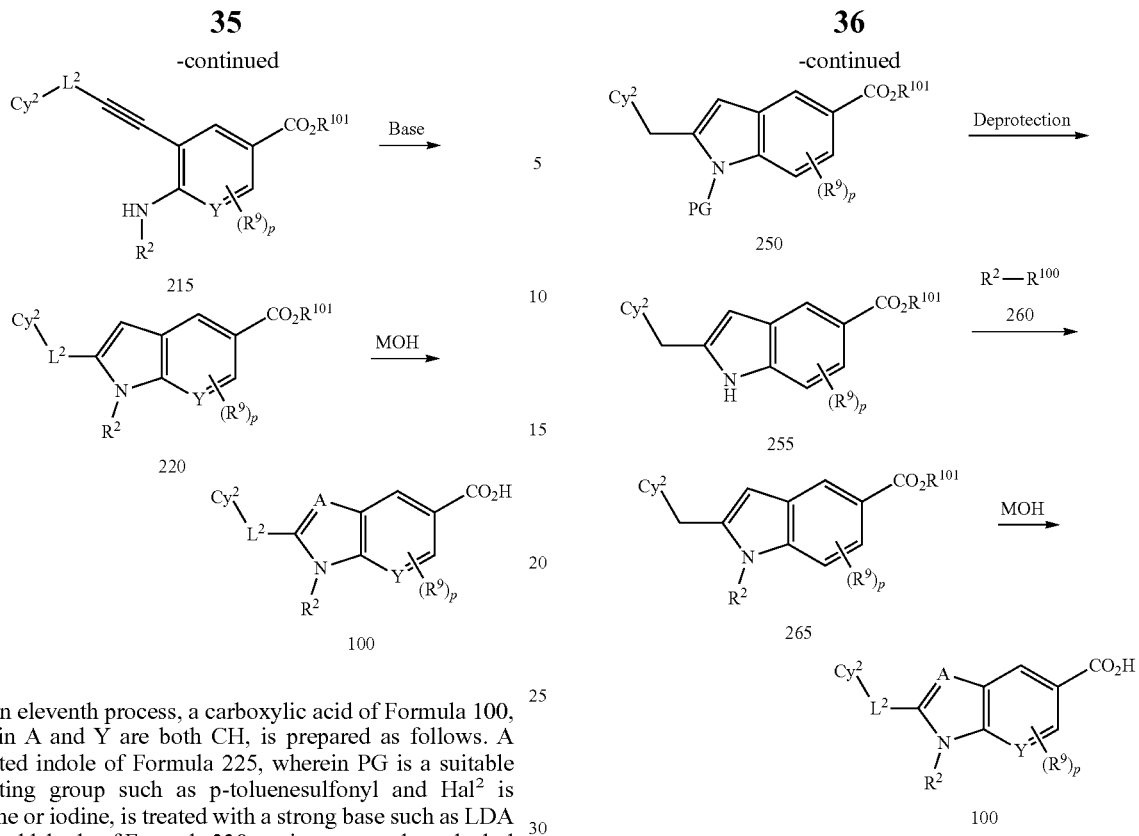

In an eleventh process, a carboxylic acid of Formula 100, wherein A and Y are both CH, is prepared as follows. A protected indole of Formula 225, wherein PG is a suitable protecting group such as p-toluenesulfonyl and Hal² is bromine or iodine, is treated with a strong base such as LDA and an aldehyde of Formula 230 to give a secondary alcohol of Formula 235. Reduction of the alcohol moiety of 235 with, for example Et₃SiH, provides a compound of Formula 240. Carbonylation of 240 with carbon monoxide in the presence of an alcohol of Formula 245, wherein $R^{101}$ is lower alkyl, a palladium catalyst such as PdCl₂(dppt) or Pd(OAc)₂/dcpp, affords an ester of Formula 250. Removal of the protecting group from 250 gives a compound of Formula 255 which is reacted with alkylating agent 260, wherein $R^{100}$ is iodine, bromine, or trifluoromethanesulfonyloxy to yield a compound of Formula 265. Finally the ester moiety in 265 is hydrolyzed with MOH, wherein M=an alkali metal, to afford a carboxylic acid of Formula 100, wherein A and Y are both CH.

In a twelfth process, an amine of Formula 115 in which both A and Y are CH is prepared as follows. A suitably protected indole of Formula 240 is deprotected to give a compound of Formula 270. Reaction of 270 with an alkylating agent of Formula 260, wherein $R^{100}$ is iodine, bromine, or trifluoromethanesulfonyloxy, in the presence of a base affords a compound of Formula 275. Finally, Hal² in 275 is converted to an amino group using, for example, NaN₃ in the presence of CuI or benzophenone imine in the presence of a palladium source and a suitable ligand to give a compound of Formula 115.

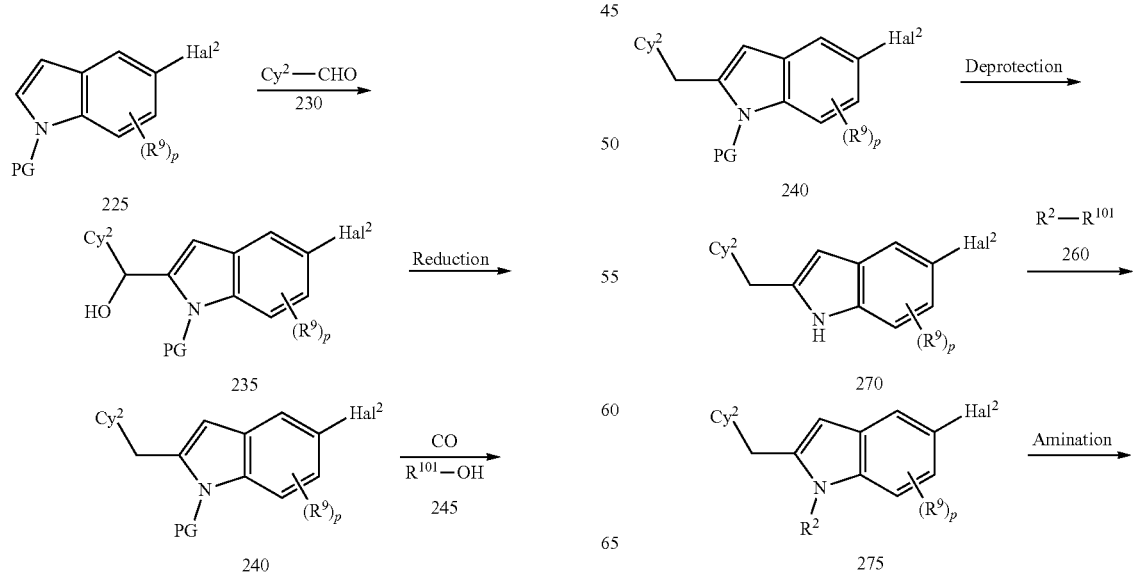

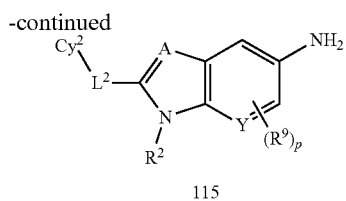

115

PREPARATION OF INTERMEDIATES

Preparation 1

4-(ethylsulfonyl)phenyl)methanamine

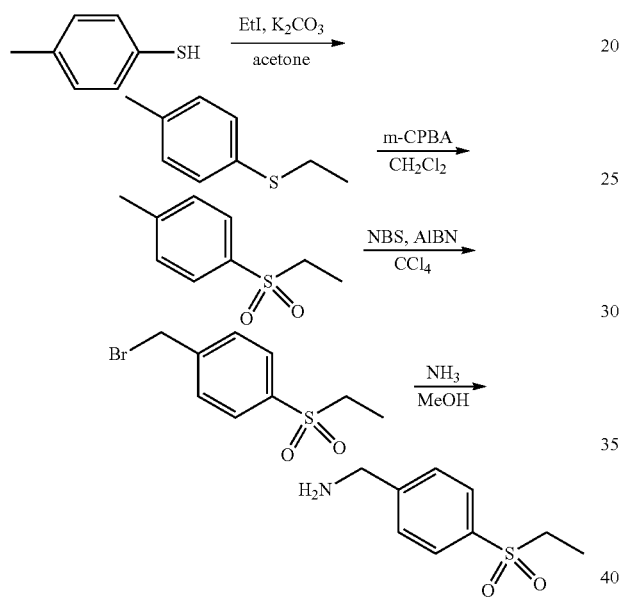

Step 1

To a mixture of 4-methylbenzenethiol (100 g, 0.8 mol) in acetone (1 L) was added iodoethane (190 g, 1.2 mol) and potassium carbonate (220 g, 1.6 mol). The mixture was stirred at 60° C. overnight. The mixture was filtered and the filtrate was concentrated under reduced pressure to afford crude ethyl(p-tolyl)sulfane (120 g, 99%) as a yellow solid, which was used for the next step without further purification.

Step 2

To a solution of crude ethyl(p-tolyl)sulfane (35 g, 0.23 mol) in CH2Cl2 (1.5 L) was added m-chloroperoxybenzoic acid (101 g, 0.59 mol) at 0° C. The mixture was stirred at rt overnight. The mixture was filtered. The filtrate was added to saturated aqueous Na2SO3 (500 mL) slowly and then stirred for 0.5 h. After partitioning, the organic layer was washed with saturated aqueous NaHCO$_3$(500 mL), dried over anhydrous Na2SO4, filtered and concentrated under reduced pressure to afford crude 1-(ethylsulfonyl)-4-methylbenzene (42.3 g, 100%) as a pale yellow solid. This material was used for the next step without further purification.

Step 3

To a solution of 1-(ethylsulfonyl)-4-methylbenzene (5 g, 25.7 mmol) in CCl$_4$ (30 mL) was added N-bromosuccinimide (5.54 g, 30.8 mmol) and azobisisobutyronitrile (0.46 g, 2.57 mmol). The mixture was stirred at 80° C. overnight. The mixture was filtered and the filtrate was concentrated under reduced pressure. The residue was added to water (50 mL) and extracted with EtOAc (3×30 mL). The combined organic layers were washed with water (2×40 mL) then brine (50 mL), dried over anhydrous Na$_2$SO$_4$, filtered and concentrated under reduced pressure to afford crude 1-(bromomethyl)-4-(ethylsulfonyl)benzene (6.62 g, 98%) as a yellow solid. This material was used for the next step without further purification.

Step 4

To a solution of 1-(bromomethyl)-4-(ethylsulfonyl)benzene (6.62 g, 25.2 mmol) in MeOH (30 mL) was added a 28% aqueous ammonium hydroxide solution (30 mL). The mixture was stirred at rt overnight. The mixture was then concentrated under reduced pressure. The residue was purified by basic preparative HPLC method B separation to afford (4-(ethylsulfonyl)phenyl) methanamine (1.5 g, 30%) as a yellow solid. LC-MS tR=1.747 min in 0-30CD_3 min chromatography (Durashell C18, 2.1*30 mm, 3 μm), MS (ESI) m/z 200.0 [M+H]+ and 399.0 [2M+H]+. 1H NMR (CDCl$_3$, 400 MHz): δ 7.85 (d, J=8.0 Hz, 2H), 7.53 (d, J=8.0 Hz, 2H), 3.98 (s, 2H), 3.10 (q, J=7.6 Hz, 2H), 1.26 (t, J=7.6 Hz, 3H).

Preparation 2

(R)-2-amino-2-(4-(ethylsulfonyl)phenyl)ethan-1-ol (3:2 mixture of enantiomers, R:S)

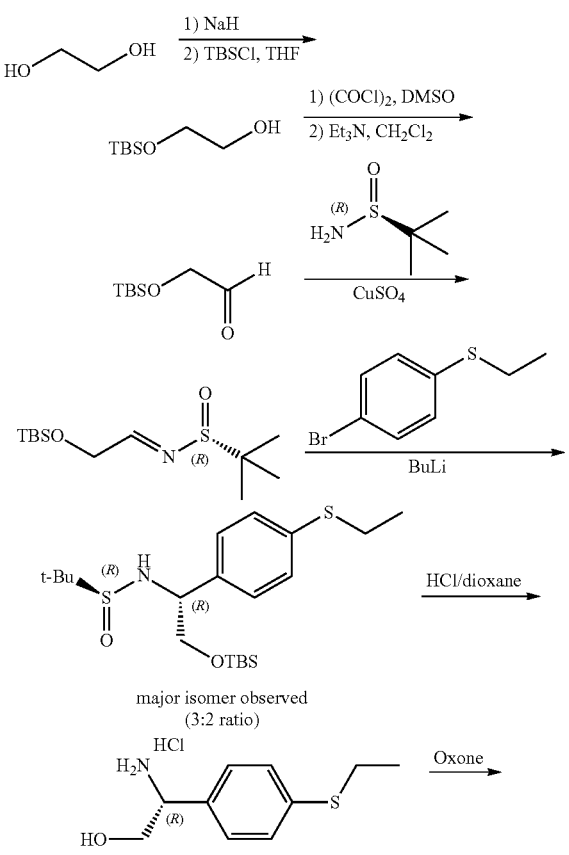

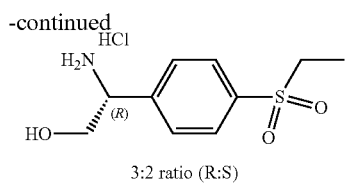

3:2 ratio (R:S)

To a suspension of NaH (12.9 g, 0.322 mol, 60% in mineral oil) in dry THF (500 mL) was added a solution of ethane-1,2-diol (20.0 g, 0.322 mol) in dry THF (100 mL) dropwise. The mixture was stirred for 1 h at rt, then TBSCl (48.59 g, 0.322 mol) was added and the mixture was stirred for another 1 h at rt. The mixture was quenched with an aqueous $K_2CO_3$ solution (100 mL, 10%) and extracted with MTBE (3×300 mL). The combined organic layers were dried over anhydrous $Na_2SO_4$, filtered and concentrated under reduced pressure. The crude residue was purified by column chromatography on silica gel (eluting with a gradient of 1% to 33% ethyl acetate in petroleum ether) to afford 2-((tert-butyldimethylsilyl)oxy)ethanol (55.0 g, 96%) as a colorless oil.

To a solution of $(COCl)_2$ (13.7 mL, 162.2 mmol) in anhydrous $CH_2Cl_2$ (400 mL) was added DMSO (25.1 mL, 353.9 mmol) at −78° C. under $N_2$. After being stirred for 30 min, a solution of 2-((tert-butyldimethylsilyl)oxy)ethanol (26.0 g, 147.5 mmol) in anhydrous $CH_2Cl_2$ (100 mL) was added dropwise. The mixture was stirred at −78° C. for 30 min and then $Et_3N$ (102.74 mL, 737.0 mmol) was added dropwise. After being stirred at −78° C. for 30 min, the reaction was allowed to warm to rt and stirred for 1 h. The reaction mixture was acidified with 2 N aqueous HCl solution to pH=4 and then extracted with $CH_2Cl_2$ (3×400 mL). The combined organic layers were dried over anhydrous $Na_2SO_4$, filtered and concentrated under reduced pressure to afford 2-((tert-butyldimethylsilyl)oxy)acetaldehyde (34.0 g, 100%) as a colorless oil. This material was used for the next step directly without further purification. To a solution of 2-((tert-butyldimethylsilyl)oxy)acetaldehyde (34.0 g, 147.5 mmol) and (R)-2-methylpropane-2-sulfinamide (19.6 g, 162.2 mmol) in DCM (400 mL) was added $CuSO_4$ (47.2 g, 295.0 mmol) at rt. The mixture was stirred at 25° C. for 48 h. The mixture was filtered and the filtrate was concentrated under reduced pressure. The residue was purified by column chromatography on silica gel (eluting with a gradient of 1% to 10% ethyl acetate in petroleum ether) to afford (R,E)-N-(2-((tert-butyldimethylsilyl)oxy)ethylidene)-2-methylpropane-2-sulfinamide (30.0 g, 73%) as a yellow oil. $^1$H NMR (CDCl$_3$ 400 MHz): δ 7.96 (t, J=3.2 Hz, 1H), 4.45 (d, J=3.2 Hz, 2H), 1.11 (s, 9H), 0.82 (s, 9H), 0.00 (s, 6H).

To a solution of (4-bromophenyl)(ethyl)sulfane (1.88 g, 8.65 mmol) in anhydrous THF (15 mL) was added n-BuLi (14.4 mL, 36.0 mmol, 2.5 M in THF) at −78° C. under $N_2$. The reaction mixture was stirred at −78° C. for 0.5 h, then a solution of (R,E)-N-(2-((tert-butyldimethylsilyl)oxy)ethylidene)-2-methylpropane-2-sulfinamide (2.0 g, 7.2 mmol) in THF (1 mL) was added dropwise to the mixture at −78° C. The reaction mixture was stirred at −78° C. for 0.5 h and was allowed to warm to rt. After 0.5 h at rt, the reaction mixture was quenched with water (10 mL) and extracted with ethyl acetate (3×20 mL). The combined organic layers were washed with $H_2O$ (10 mL) then brine (10 mL), dried over anhydrous sodium sulfate, filtered and concentrated under reduced pressure.

The crude residue was purified by column chromatography on silica gel (eluting with a gradient of 5% to 10% ethyl acetate in petroleum ether) to afford a 3:2 mixture of (R)—N—((R)-2-((tert-butyldimethylsilyl)oxy)-1-(4-(ethylthio)phenyl)ethyl)-2-methylpropane-2-sulfinamide and (R)—N—((S)-2-((tert-butyldimethylsilyl)oxy)-1-(4-(ethylthio)phenyl)ethyl)-2-methylpropane-2-sulfinamide (2.86 g, 47.9%) as a yellow oil. This 3:2 mixture of diastereomers was used for the subsequent reactions. $^1$H NMR (CDCl$_3$ 400 MHz): δ 7.24-7.16 (m, 4H), 4.47-4.40 (m, 1H), 4.21 (s, 1H), 3.75-3.67 (m, 1H), 3.60-3.47 (m, 1H), 2.90 (q, J=7.2 Hz, 2H), 1.27 (t, J=7.2 Hz, 3H), 1.18 (s, 9H), 0.85 (s, 9H), 0.02 (s, 3H), 0.00 (s, 3H).

To a solution of (R)—N—((R)-2-((tert-butyldimethylsilyl)oxy)-1-(4-(ethylthio)phenyl)ethyl)-2-methylpropane-2-sulfinamide (2.86 g, 6.86 mmol), as a 3:2 mixture of diastereomers from previous step, in dioxane (10 mL) was added HCl in dioxane (20 mL, 4 M) at it. The mixture was stirred for 3 h at rt and was then concentrated under reduced pressure to afford crude (R)-2-amino-2-(4-(ethylthio)phenyl)ethan-1-ol HCl salt (3.0 g, 100%) as a white solid. This crude material was a 3:2 mixture of enantiomers (R:S) and used for the next step without further purification.

To a solution of (R)-2-amino-2-(4-(ethylthio)phenyl)ethan-1-ol HCl salt (3.0 g, 6.86 mmol), as a 3:2 mixture of enantiomers/R:S, in $H_2O$ (30 mL) was added Oxone® monopersulfate (8.4 g, 13.72 mmol) at rt. The mixture was stirred for 1.5 h at rt and was lyophilized directly. After lyophilization, the crude product was purified by flash column chromatography on silica gel (eluting with MeOH) to give crude (R)-2-amino-2-(4-(ethylsulfonyl)phenyl)ethan-1-ol HCl salt (3:2 mixture of enantiomers, R:S) (1.25 g, 80%) as a yellow solid. $^1$H NMR (CDCl$_3$ 400 MHz): δ 7.99 (d, J=8.4 Hz, 2H), 7.73 (d, J=8.0 Hz, 2H), 4.55-4.50 (m, 1H), 3.99-3.91 (m, 1H), 3.85-3.80 (m, 1H), 3.23 (q, J=7.2 Hz, 2H), 1.21 (t, J=7.2 Hz, 3H).

Preparation 3

(5-(ethylsulfonyl)pyridin-2-yl) methanamine

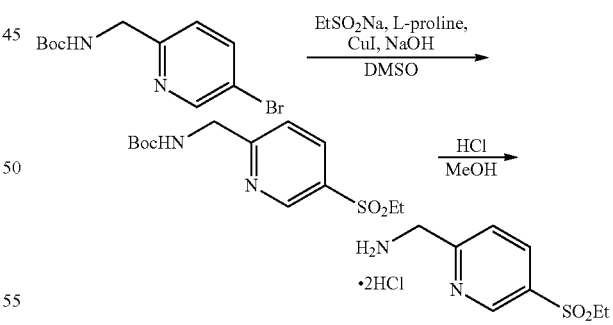

To a flame dried flask equipped with a stir bar was added tert-butyl ((5-bromopyridin-2-yl)methyl)carbamate (2.92 g, 10.2 mmol), ethane sulfinic acid sodium salt (2.36 g, 20.3 mmol), L-proline (234 mg, 2.03 mmol), copper (I) iodide (194 mg, 1.02 mmol) and sodium hydroxide (81.3 mg, 2.03 mmol). The flask was purged with $N_2$, then DMSO (35 mL) was added. The reaction mixture was heated to 110° C. and stirred for 15 h. The flask was then cooled to rt and the mixture was partitioned between EtOAc (150 mL) and saturated aqueous ammonium chloride (150 mL). The organic phase was separated, washed with brine (50 mL), dried over anhydrous MgSO₄, filtered and concentrated under reduced pressure. The residue was purified by silica gel chromatography (eluting with 35% EtOAc in hexanes, gradient to 60%) to afford tert-butyl((5-bromopyridin-2-yl)methyl)carbamate (1.81 g, 59%). LC-MS t$_R$=0.74 min in 1 min chromatography, MS (ESI) m/z 301.4 [M+H]⁺. ¹H NMR (CDCl₃, 400 MHz): δ 9.02 (dd, J=0.8 Hz, 2.0 Hz, 1H), 8.15 (dd, J=2.4 Hz, 8.4 Hz, 1H), 7.49 (dd, J=0.8 Hz, 8.4 Hz, 1H), 5.49 (broad s, 1H), 4.55 (d, J=7.0 Hz, 2H), 3.15 (q, J=7.2 Hz, 2H), 1.47 (s, 9H), 1.31 (t, J=7.2 Hz, 3H).

To a solution of tert-butyl ((5-bromopyridin-2-yl)methyl)carbamate (1.81 g, 6.03 mmol) in MeOH (40 mL) at 0° C. was added acetyl chloride (4.30 mL, 60.3 mmol) dropwise over 5 min. The solution was allowed to warm to rt and was stirred for 3 h. The mixture was concentrated under reduced pressure to yield 1.64 g (5-(ethylsulfonyl)pyridin-2-yl)methanamine bis-hydrochloride salt (~100%). This material was used directly for the next step without purification. LC-MS t$_R$=0.25 min in 1 min chromatography, MS (ESI) m/z 201.2 [M+H]⁺. ¹H NMR (CD₃OD, 400 MHz): δ 9.09 (d, J=1.2 Hz, 1H), 8.35 (dd, J=2.4 Hz, 8.4 Hz, 1H), 7.49 (d, J=8.4 Hz, 1H), 4.45 (s, 2H), 3.31 (q, J=7.2 Hz, 2H), 1.26 (t, J=7.2 Hz, 3H).

Preparation 4

2-(6-(trifluoromethyl)tetrahydro-2H-pyran-3-yl)acetic acid

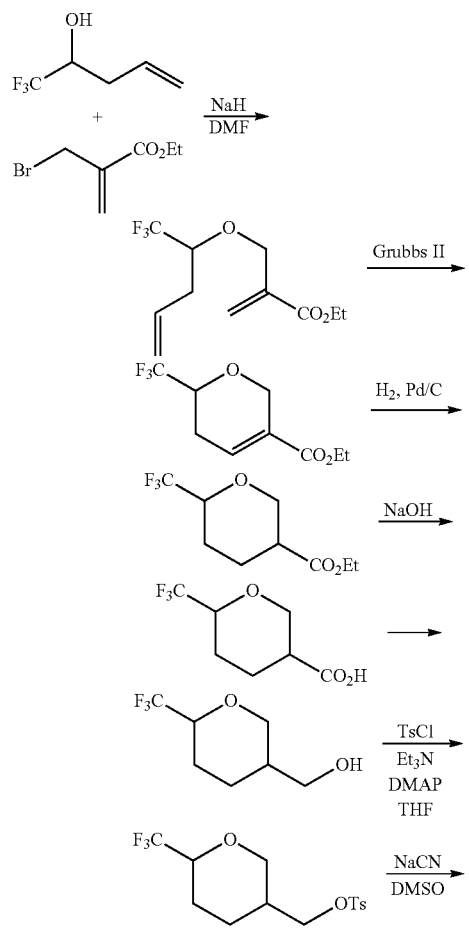

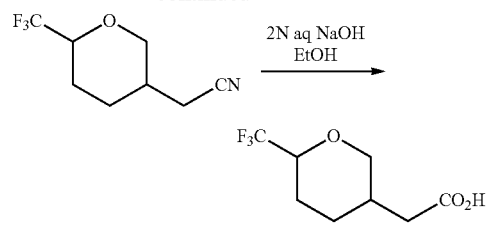

Preparation of Compounds of Formula I

Compounds of Formula I were prepared according to the general procedures outlined below.

Example 1

1-ethyl-N-(4-(ethylsulfonyl)benzyl)-2-(4-(trifluoromethyl)benzyl)-1H-indole-5-carboxamide (Compound IN-1)

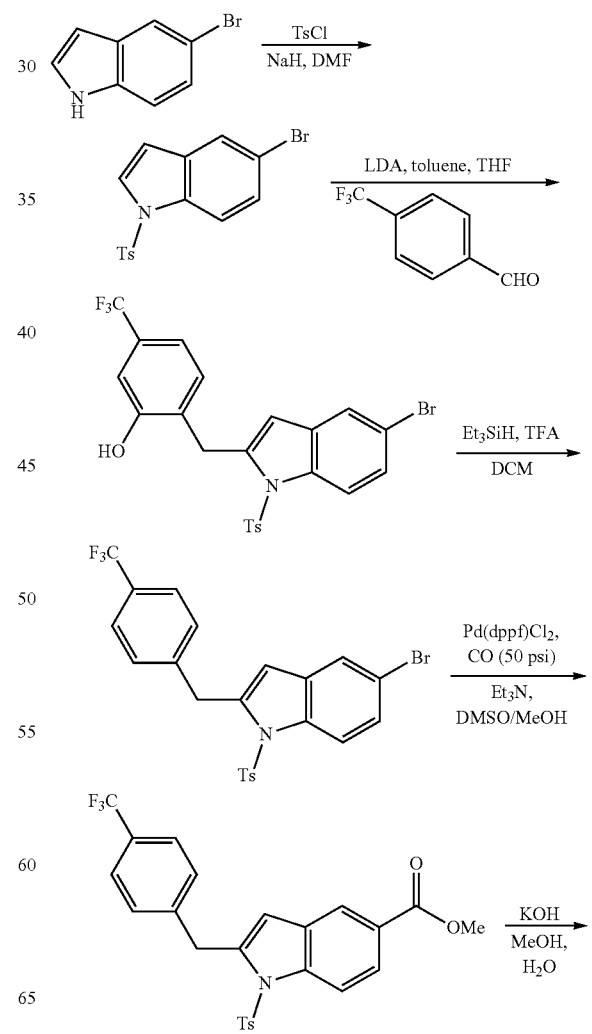

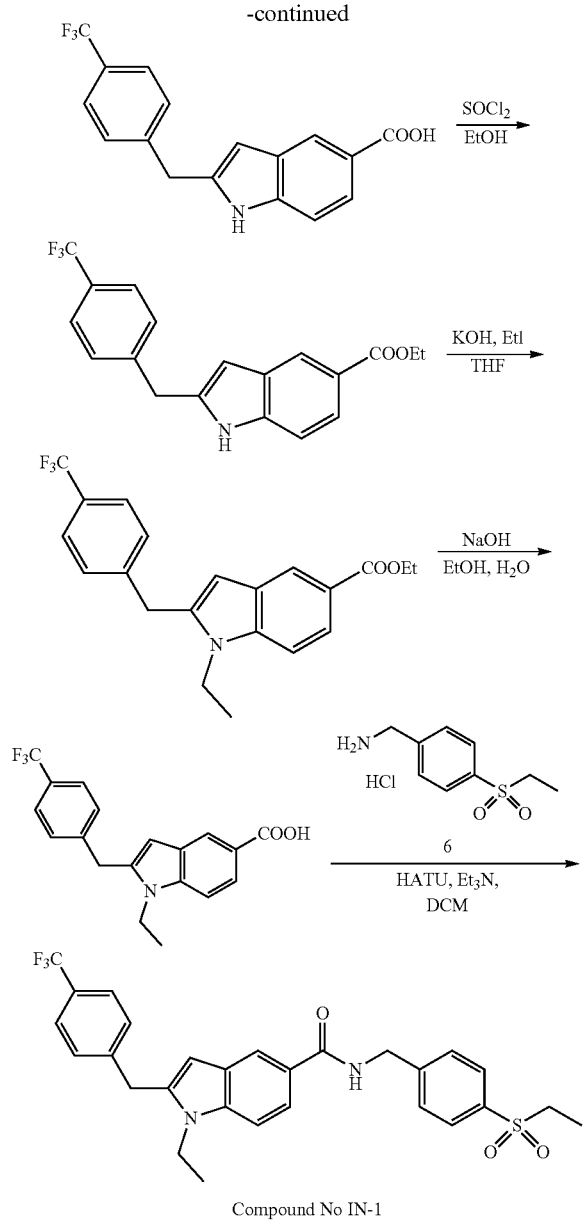

Compound No IN-1

Step 1

To a solution of 5-bromo-1H-indole (5.0 g, 25.5 mmol) in anhydrous DMF (100 mL) was added NaH (1.2 g, 30.6 mmol, 60% in mineral oil) under $N_2$. The reaction mixture was stirred at 0° C. for 1 h. 4-methylbenzene-1-sulfonyl chloride (5.8 g, 30.6 mmol) in anhydrous DMF (25 mL) was added dropwise at 0° C. and the reaction mixture was stirred at room temperature for 4 h. TLC (petroleum ether/EtOAc=5/1) showed the reaction was completed. Water (50 mL) was added at 0° C. Most solid was precipitated out. Then the solid was filtered and washed with water. The solid was collected and dried under reduced pressure to afford 5-bromo-1-tosyl-1H-indole (8.2 g, 92% yield) as a white solid. $^1$H NMR (CDCl$_3$ 400 MHz): δ 7.86 (d, J=8.4 Hz, 1H), 7.74 (d, J=8.4 Hz, 2H), 7.66 (d, J=1.6 Hz, 1H), 7.56 (d, J=7.6 Hz, 1H), 7.38 (d, J=8.4 Hz, 1H), 7.23 (d, J=8.0 Hz, 2H), 6.59 (d, J=3.2 Hz, 1H), 2.35 (s, 3H).

Step 2

To a solution of 5-bromo-1-tosyl-1H-indole (0.5 g, 1.43 mmol) in anhydrous toluene (5 mL) was added LDA (0.855 mL, 1.71 mmol, 2.0 M in THF) at −78° C. under $N_2$. After addition, the reaction mixture was stirred at −78° C. for 30 min. 4-(trifluoromethyl)benzaldehyde (298 mg, 1.71 mmol) in THF (3 mL) was added dropwise at −78° C. under $N_2$. The reaction mixture was stirred at room temperature for 2 h. TLC (petroleum ether/EtOAc=5/1) showed the reaction was completed. The mixture was quenched with water (10 mL) and extracted with EtOAc (3×15 mL). The combined organic layers were dried over anhydrous $Na_2SO_4$, filtered and concentrated under reduced pressure. The residue was purified by column chromatography on silica gel eluting with petroleum ether:ethyl acetate=7:3 to afford (5-bromo-1-tosyl-1H-indol-2-yl)(4-(trifluoromethyl)phenyl)methanol (0.36 g, 48%) as a yellow solid. $^1$H NMR (CDCl$_3$ 400 MHz): δ 7.97 (d, J=8.8 Hz, 1H), 7.62 (d, J=8.0 Hz, 2H), 7.59 (d, J=8.0 Hz, 2H), 7.54 (d, J=4.0 Hz, 1H), 7.51 (d, J=8.0 Hz, 2H), 7.41 (d, J=8.0 Hz, 1H), 7.21 (d, J=8.4 Hz, 2H), 6.42 (d, J=4.8 Hz, 1H), 6.13 (s, 1H), 3.64 (d, J=5.2 Hz, 1H), 2.37 (s, 3H).

Step 3

To a solution of (5-bromo-1-tosyl-1H-indol-2-yl)(4-(trifluoromethyl)phenyl)methanol (260 mg, 0.5 mmol) in $CH_2Cl_2$ (10 mL) was added $Et_3SiH$ (1.4 mL) and TFA (1.4 mL) at 0° C. under $N_2$. The reaction mixture was stirred at room temperature for 2 h. TLC (petroleum ether/EtOAc=5/1) showed the reaction was completed. The mixture was quenched with water (10 mL) and extracted with DCM (3×10 mL). The combined organic layers were dried over anhydrous $Na_2SO_4$, filtered and concentrated under reduced pressure. The residue was purified by column chromatography on silica gel eluting with petroleum ether:ethyl acetate=96:4 to afford 5-bromo-1-tosyl-2-(4-(trifluoromethyl)benzyl)-1H-indole (0.23 g, 91%) as a white solid. LC-MS Method 2 $t_R$=1.018 min in 5-95AB_1.5 min chromatography (Merck RP-18e 25-2 mm), MS (ESI) m/z 507.8 [M+H]$^+$. $^1$H NMR (CDCl$_3$ 400 MHz): δ 8.05 (d, J=8.8 Hz, 1H), 7.55 (d, J=4.0 Hz, 1H), 7.51 (d, J=8.0 Hz, 3H), 7.43 (d, J=8.0 Hz, 2H), 7.39 (dd, J=4.0, 8.0 Hz, 1H), 7.28 (s, 1H), 7.12 (d, J=8.0 Hz, 2H), 6.17 (s, 1H), 4.42 (s, 2H), 2.34 (s, 3H).

Step 4

To a solution of 5-bromo-1-tosyl-2-(4-(trifluoromethyl)benzyl)-1H-indole (300 mg, 0.59 mmol) in dry MeOH (20 mL) was added DMSO (1 mL) and $Et_3N$ (1 mL). Then Pd(dppf)Cl$_2$ (20 mg, 0.024 mmol) was added under $N_2$. The mixture was stirred at 75° C. under CO (50 psi) for 20 h. The reaction mixture was filtered and the filter cake was washed with EtOAc (20 mL). The combined solvents were removed under reduced pressure. The mixture was partitioned between ethyl acetate (30 mL) and water (30 mL). The organic layer was washed with brine, dried over anhydrous $Na_2SO_4$, filtered and concentrated to afford crude product. The crude product was purified by column chromatography on silica gel eluting with petroleum ether:ethyl acetate=93:7 to afford methyl 1-tosyl-2-(4-(trifluoromethyl)benzyl)-1H-indole-5-carboxylate (142 mg, 49%) as a white solid. LC-MS Method 2 $t_R$=1.11 min in 5-95AB_1.5 min chromatography (Merck RP-18e 25-2 mm), MS (ESI) m/z 488.0 [M+H]$^+$.

Step 5

To a solution of methyl 1-tosyl-2-(4-(trifluoromethyl)benzyl)-1H-indole-5-carboxylate (90 mg, 0.19 mmol) in MeOH (3 mL) was added KOH (207 mg, 3.69 mmol) and water (1.0 mL). The reaction mixture was stirred at 50° C. for 20 h. The solvents were removed. Water (5 mL) was added. The mixture was acidified with 1 N HCl solution to pH=6 and most solid was precipitated out. The solid was filtered and then dried under reduced pressure to afford 2-(4-(trifluoromethyl)benzyl)-1H-indole-5-carboxylic acid (59 mg, 100%) as a pale yellow solid. LC-MS Method 2 $t_R$=0.754 min in 5-95AB_1.5 min chromatography (Merck RP-18e 25-2 mm), MS (ESI) m/z 319.9 [M+H]$^+$.

Step 6

To a solution of 2-(4-(trifluoromethyl)benzyl)-1H-indole-5-carboxylic acid (59 mg, 0.185 mmol) in EtOH (5 mL) was added SOCl$_2$ (1 mL). Then the mixture was stirred at 60° C. for 3.5 h. Then the reaction solution was concentrated under reduced pressure. The residue was purified by preparative TLC (petroleum ether:ethyl acetate=5:1) to afford ethyl 2-(4-(trifluoromethyl)benzyl)-1H-indole-5-carboxylate (40 mg, 63%) as a red solid.

LC-MS Method 2 $t_R$=0.996 min in 5-95AB_1.5 min chromatography (Merck RP-18e 25-2 mm), MS (ESI) m/z 347.9 [M+H]$^+$.

Step 7

To a solution of ethyl 2-(4-(trifluoromethyl)benzyl)-1H-indole-5-carboxylate (30 mg, 0.086 mmol) in dry THF (2 mL) was added KOH (14 mg, 0.258 mmol) and EtI (27 mg, 0.172 mmol). Then the mixture was stirred at 50° C. for 1 h. TLC (petroleum ether/EtOAc=5/1) showed the reaction was completed. The mixture was quenched with water (5 mL) and extracted with EtOAc (3×5 mL). The combined organic layers were dried over anhydrous Na$_2$SO$_4$, filtered and concentrated under reduced pressure. The residue was purified by preparative TLC (petroleum ether:ethyl acetate=5:1) to afford ethyl 1-ethyl-2-(4-(trifluoromethyl)benzyl)-1H-indole-5-carboxylate (17 mg, 53%) as a red solid. LC-MS Method 2 $t_R$=0.938 min in 5-95AB_1.5 min chromatography (Merck RP-18e 25-2 mm), MS (ESI) m/z 376.0 [M+H]$^+$.

Step 8

To a solution of ethyl 1-ethyl-2-(4-(trifluoromethyl)benzyl)-1H-indol-5-carboxylate (18 mg, 0.048 mmol) in EtOH (2 mL) was added H$_2$O (0.5 mL) and NaOH (38 mg, 0.96 mmol). The reaction mixture was stirred at room temperature for 20 h. TLC (petroleum ether/EtOAc=5/1) showed the reaction was completed. The solvent was removed and water (5 mL) was added. The mixture was acidified with 1 N HCl solution to pH=5-6 and extracted with EtOAc (3×10 mL). The combined organic layers were dried over anhydrous Na$_2$SO$_4$, filtered and concentrated to afford crude 1-ethyl-2-(4-(trifluoromethyl)benzyl)-1H-indole-5-carboxylic acid (16 mg, 96% yield) as a white solid, which was used for next step without further purification.

Step 9

To a mixture of 1-ethyl-2-(4-(trifluoromethyl)benzyl)-1H-indole-5-carboxylic acid (16 mg, 0.046 mmol), (4-(ethylsulfonyl)phenyl)methanamine hydrochloride (16 mg, 0.069 mmol) and HATU (9 mg, 0.069 mmol) in dry CH$_2$Cl$_2$ (2 mL) was added Et$_3$N (14 mg, 0.138 mmol). Then the mixture was stirred at room temperature for 1 h. Water (8 mL) was added. The mixture was extracted with CH$_2$Cl$_2$ (3×10 mL). The combined organic layers were washed with brine, dried over anhydrous sodium sulfate, filtered and concentrated under reduced pressure. The residue was purified by basic preparative HPLC separation, then lyophilized directly to afford 1-ethyl-N-(4-(ethylsulfonyl)benzyl)-2-(4-(trifluoromethyl)benzyl)-1H-indole-5-carboxamide (IN-1, 17.60 mg, 72%) as a white solid. LC-MS Method 2 $t_R$=0.822 min in 5-95AB_1.5 min chromatography (MK RP-18e 25-2 mm), MS (ESI) m/z 529.0 [M+H]$^+$. $^1$H NMR (CDCl$_3$ 400 MHz): δ 8.07 (s, 1H), 7.86 (d, J=8.0 Hz, 2H), 7.70 (dd, J=4.0, 8.0 Hz, 1H), 7.58 (d, J=8.0 Hz, 2H), 7.56 (d, J=8.0 Hz, 2H), 7.33 (d, J=8.0 Hz, 2H), 7.32 (d, J=8.0 Hz, 1H), 6.64 (t, J=6.0 Hz, 1H), 6.33 (s, 1H), 4.78 (d, J=6.0 Hz, 2H), 4.20 (s, 2H), 4.07 (q, J=7.2 Hz, 2H), 3.10 (q, J=7.6 Hz, 2H), 1.27 (t, J=7.6 Hz, 3H), 1.21 (t, J=7.6 Hz, 3H).

Basic Preparative HPLC Method

Mobile phase A: water with 0.05% NH$_3$.H$_2$O

Mobile phase B: CH$_3$CN

Flow rate: 25 mL/min.

Detection: UV 220 nm/254 nm

Column: Gemini 150*25 mm*5 um

Column temperature: 30° C.

| Time in min | % A | % B |
|---|---|---|
| 0.00 | 48 | 52 |
| 10.00 | 18 | 82 |
| 10.20 | 0 | 100 |
| 12.00 | 0 | 100 |

The following compounds are prepared by similar procedures:

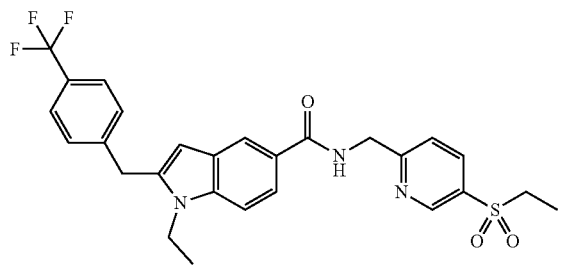

Compound IN-2

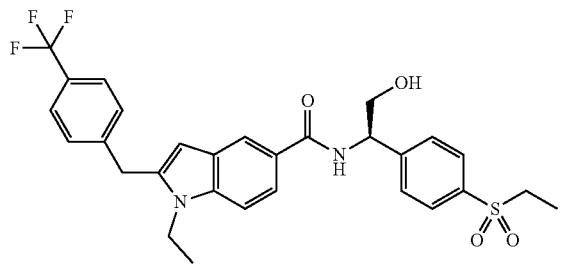

Compound IN-3

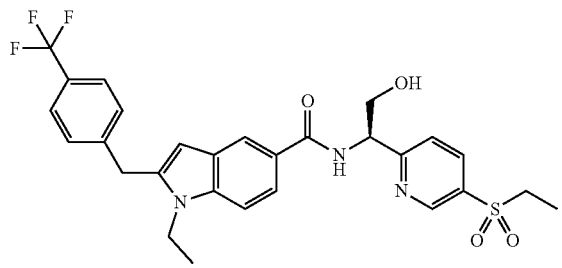

Compound IN-4

Isomer 1$^{a,b}$

Compound IN-4
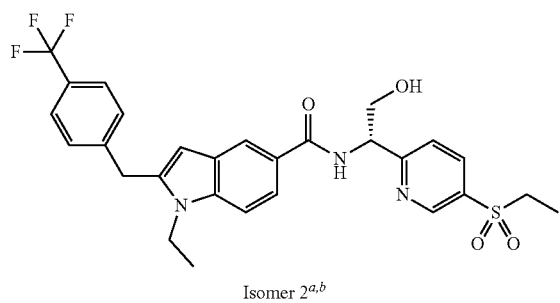
Isomer 2[a,b]
Compound IN-5
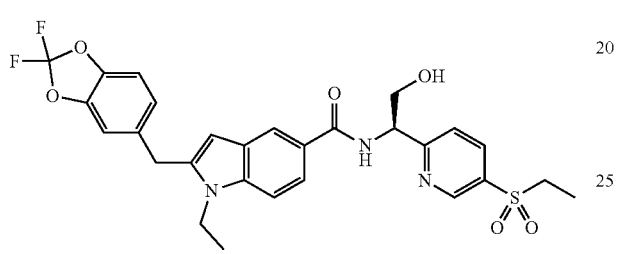
Compound IN-6
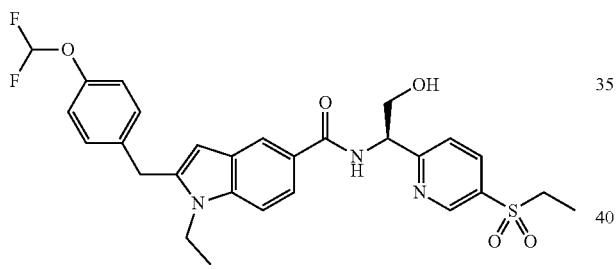
Compound IN-7
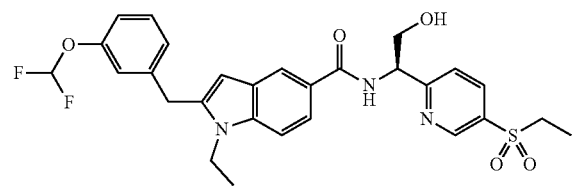
Compound IN-8
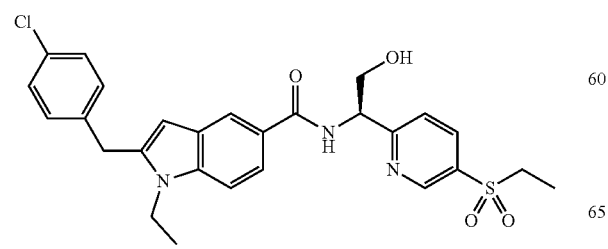
Compound IN-9[d]
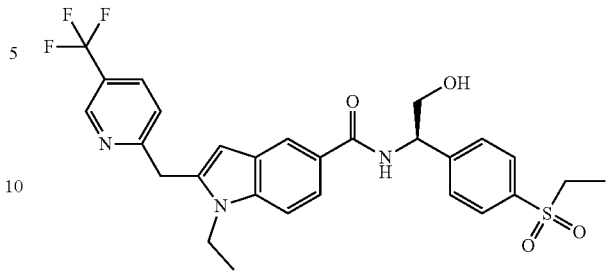
Example 2
1-cyclopropyl-N-(4-(ethylsulfonyl)benzyl)-2-(((1r,4r)-4-(trifluoromethyl)cyclohexyl)methyl)-1H-pyrrolo[2,3-b]pyridine-5-carboxamide (Compound AI-1)
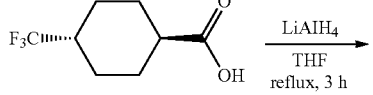
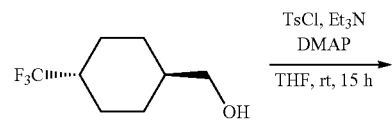
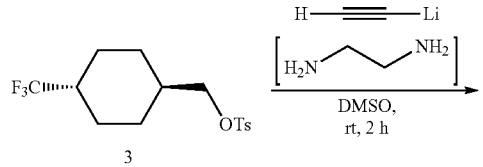
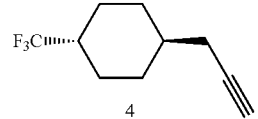
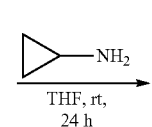
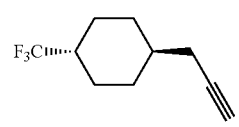

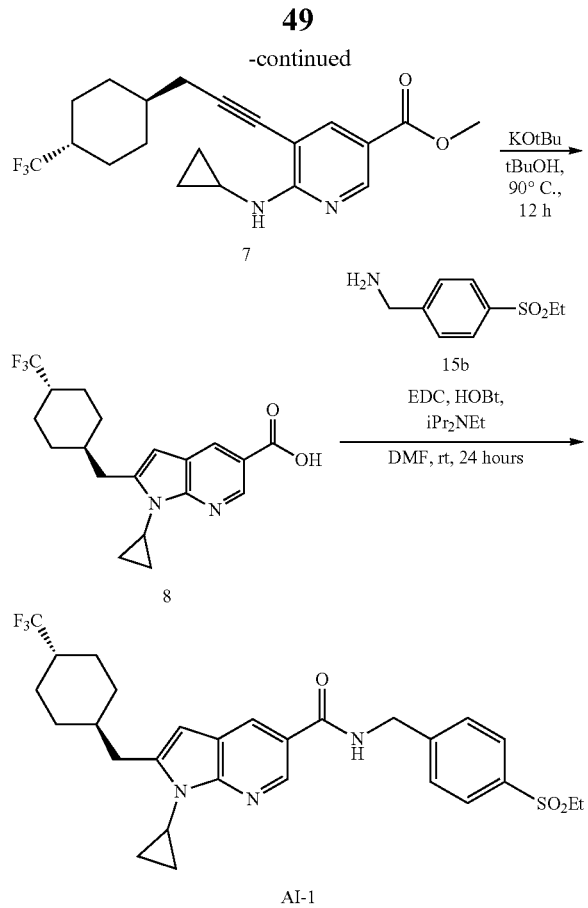

Step 1

To a solution of 1 (650 mg, 3.31 mmol) in THF (5 mL) was added a 1M solution of LiAlH$_4$ in THF (3.97 mL, 3.97 mmol) dropwise at room temperature. The reaction was refluxed for 3 hours (~80° C. oil bath). After cooling to room temp, Et$_2$O (5 mL) was added and the reaction was filtered through celite. The filtrate was carefully quenched at 0° C. using 1 N NaOH until the bubbling subsided and the mixture stirred at room temp for 10 minutes after quenching. Et$_2$O and H$_2$O were added for the workup. The Et$_2$O layer was separated and dried using MgSO$_4$. Carefully evaporation of the Et$_2$O gave product 2 as an oil. This material was used directly for the next step without purification.

Step 2

To a solution of crude 2 (from above), Et$_3$N (0.92 mL, 6.62 mmol) and DMAP (40 mg, 0.33 mmol) in THF (5 mL) was added TsCl (948 mg, 4.48 mmol) at room temp. The reaction stirred for 15 hours. A sat. NaHCO$_3$ solution (5 mL) and DCM (10 mL) was added for the workup. The DCM layer was separated, washed with brine, dried using Na$_2$SO$_4$ and evaporated. The crude material was purified by ISCO flash chromatography (eluting with 10% EtOAC in hexanes) to afford 250 mg of 3 as a crystalline solid (22%, 2 steps).

LC-MS $t_R$=1.809 min in 2 min chromatography (UV); no ionization peak $^1$H NMR (CDCl$_3$, 400 MHz): δ 7.93 (d, J=8.4 Hz, 1H), 7.78 (d, J=8.4 Hz, 1H), 7.41 (d, J=8.4 Hz, 1H), 7.35 (d, J=8.4 Hz, 1H), 3.84 (d, J=6.4 Hz, 2H), 2.46 (s, 3H), 1.98-1.82 (m, 5H), 1.69-1.63 (m, 1H), 1.33-1.23 (m, 2H), 1.03-0.93 (m, 2H).

Step 3

To a suspension of lithium acetylide ethylenediamine complex (71 mg, 0.77 mmol) in DMSO (2 mL) was added a solution of 3 (200 mg, 0.60 mmol) in DMSO (1 mL) at room temp. The reaction stirred for 2 hours at room temp. Water (10 mL) and Et$_2$O (15 mL) were added for the workup. The Et$_2$O layer was separated, washed with brine and dried using MgSO$_4$. Carefully evaporation of the Et$_2$O gave volatile product 4 as a colorless oil (34 mrg, 30%). This crude material was used for the next step without further purification. LC-MS $t_R$=No UV or ionization peak observed on LCMS $^1$H NMR (CDCl$_3$, 400 MHz): δ 3.48 (s, 1H), 2.61 (d, J=2.8 Hz, 2H), 2.13-2.10 (m, 2H), 1.98-1.96 (m, 4H), 1.42-1.32 (m, 2H), 1.11-1.05 (m, 2H).

Step 4

To a solution of 5 (300 mg, 1.19 mmol) in THF (5 mL) was added cyclopropylamine (0.18 mL, 2.5 mmol) dropwise at room temp. The reaction stirred for 24 hours at room temp. Water and EtOAc were added for the workup. The EtOAc layer was separated, washed with brine, dried using Na$_2$SO$_4$ and evaporated. The crude material was purified by ISCO flash chromatography (eluting with 30% EtOAc in hexanes) to give compound 6 (158 mg, 49%). LC-MS $t_R$=1.286 min in 2 min chromatography; MS (ESI) m/z 271.19 and 273.19 [M+H]$^+$.

Step 5

A suspension of 6 (50 mg, 0.18 mmol), 4 (34 mg, 0.18 mmol), PdCl$_2$(PPh$_3$)$_2$ (6 mg, 0.01 mmol), CuI (4 mg, 0.02 mmol) and Et$_3$N (0.05 mL, 0.36 mmol) in THF (2 mL) was degassed with N$_2$ for 5 min at room temp. The reaction vessel was sealed and heated to 85° C. for 15 hours. The reaction mixture was filtered through celite and evaporated. The crude material was purified by ISCO flash chromatography (eluting with 30% EtOAc in hexanes) to afford compound 7 (23 mg, 34%). LC-MS $t_R$=1.735 min in 2 min chromatography; MS (ESI) m/z 381.31 [M+H]$^+$. $^1$H NMR (CDCl$_3$, 400 MHz): δ 8.83 (s, 1H), 8.05 (s, 1H), 5.78 (s, 1H), 3.90 (s, 3H), 2.95-3.00 (m, 1H), 2.46 (d, J=5.2 Hz, 2H), 2.07-2.04 (m, 4H), 1.65-1.63 (m, 2H), 1.47-1.37 (m, 2H), 1.22-1.13 (m, 2H), 0.97-0.95 (m, 2H), 0.62-0.63 (m, 2H).

Step 6

To a solution of 7 (20 mg, 0.05 mmol) in t-BuOH (1 mL) was added KOtBu (30 mg, 0.26 mmol) at room temp. The reaction was heated to 90° C. for 12 hours. 1 N NaOH (2 mL) and iPrOAc (3 mL) were added for the workup. The iPrOAc layer was separated and extracted with 1 N NaOH (2 mL). The NaOH layers were combined and carefully acidified at 0° C. using conc. HCl to adjust the pH to ~4. The product (8) was then extracted into EtOAc twice. The EtOAc layers were combined, dried using Na$_2$SO$_4$ and evaporated to give nearly pure crude product 8 (16 mg, 84%). LC-MS $t_R$=1.477 min in 2 min chromatography; MS (ESI) m/z 367.32 [M+H]$^+$. $^1$H NMR (CDCl$_3$, 400 MHz): δ 8.80 (s, 1H), 8.25 (s, 1H), 6.06 (s, 1H), 2.97-2.94 (1H, m), 2.63 (d, J=6.8 Hz, 2H), 1.90-1.57 (m, 6H), 1.12-0.70 (m, 8H).

Step 7

A solution of 8 (16 mrg, 0.04 mmol), 4-(ethylsulfonyl) benzylamine (13 mg, 0.07 mmol), EDC (13 mg, 0.07), iPr$_2$NEt (9 mg, 0.07 mmol) and HOBt (10 mg, 0.07 mmol) in DMF (1 mL) was stirred at room temp for 24 hours. H$_2$O and EtOAc were added for the workup. The EtOAc layer was separated, dried using Na$_2$SO$_4$ and evaporated to give crude product. Purification by Gilson HPLC afforded 4.38 mg of compound AI-1 as the TFA salt. LC-MS $t_R$=1.652 min in 2 min chromatography; MS (ESI) m/z 548.55 [M+H]$^+$. $^1$H NMR (CD$_3$OD, 400 MHz): δ 9.12 (t, J=6.4 Hz, 1H), 8.66 (d, J=2.4 Hz, 1H), 8.30 (d, J=1.6 Hz, 1H), 7.83 (d, J=8.8 Hz, 2H), 7.58 (d, J=8.8 Hz, 2H), 6.32 (s, 1H), 4.66 (d, J=4.0 Hz, 2H), 3.20-3.18 (m, 1H), 3.13 (q, J=7.6 Hz, 2H), 2.84 (d, J=6.8 Hz, 2H), 2.09-2.02 (m, 1H), 1.91-1.88 (m, 4H), 1.82-1.77 (m, 1H), 1.35-1.03 (m, 8H), 1.14 (t, J=7.6 Hz, 3H). $^{19}$F NMR (CD$_3$OD, 400 MHz): δ −75.39 (d)

The following compounds are prepared using analogous procedures:

Compound AI-2

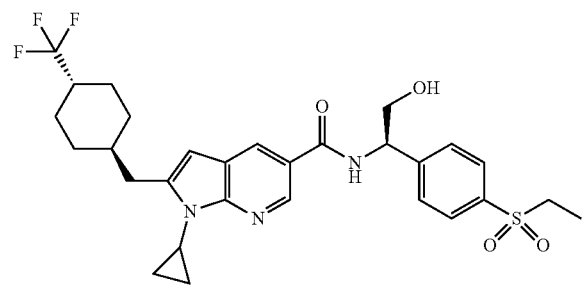

Compound AI-3

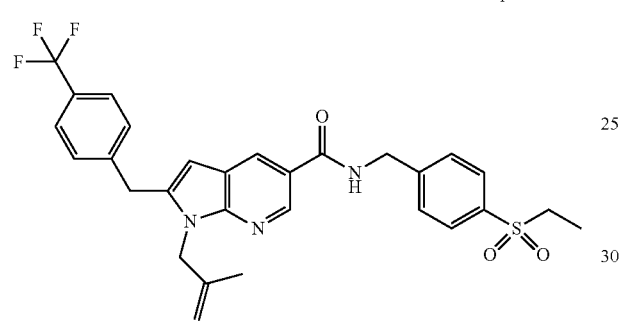

Example 3

1-cyclopropyl-N—((R)-1-(4-(ethylsulfonyl)phenyl)-2-hydroxyethyl)-2-(((1r,4R)-4-(trifluoromethyl)cyclohexyl)oxy)-1H-benzo[d]imidazole-5-carboxamide (Compound BE-1)

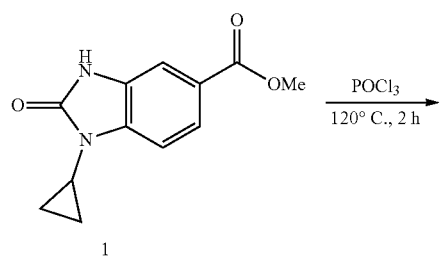

1

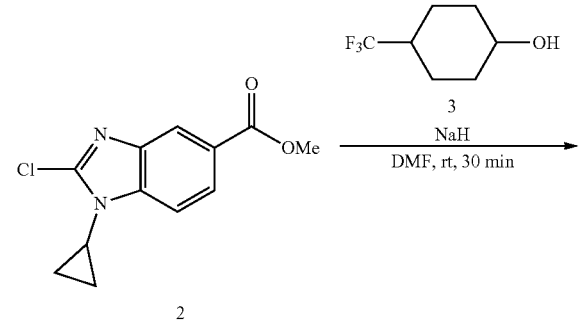

2

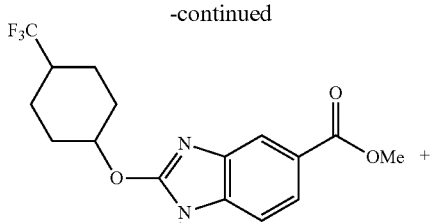

4 cis:trans mixture (~1:1)

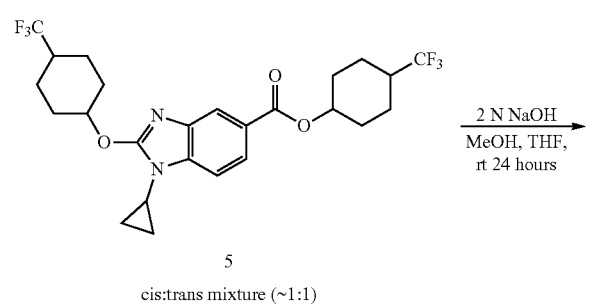

5 cis:trans mixture (~1:1)

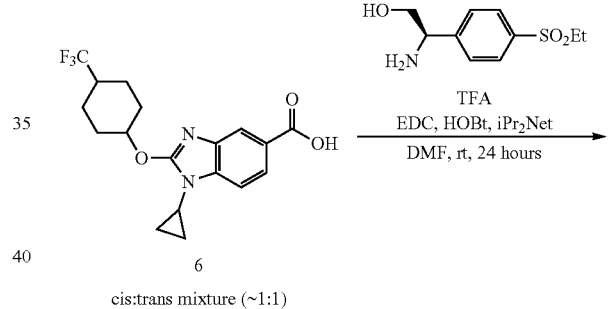

6 cis:trans mixture (~1:1)

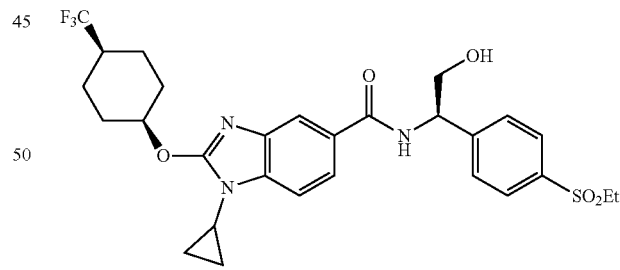

BE-1
(trans isomer isolated from HPLC)

Step 1

Compound 1 is known compound in the literature. Xu, Y.; Lin, H.; Ruan, X.; Yang, S.; Hao, G.; Yang, W.; Yang, G. *Eur. J. Med. Chem.* 2015, 92, 427-438.

A solution of 1 (500 mg, 2.16 mmol) in POCl$_3$ (3 mL) was stirred at 120° C. for 2 hours. Upon cooling, the POCl$_3$ was removed by rotovap to give the crude product. This crude product was taken up in 5 mL of DCM and washed with sat. NaHCO$_3$ (3 mL). The DCM layer was then dried using Na₂SO₄ and evaporated. The crude material was purified using ISCO flash chromatography (eluting with 50% EtOAc in hexanes) to afford 307 mg of 2 as a white solid (57%). LC-MS $t_R$=1.308 min in 2 min chromatography; MS (ESI) m/z 251.10 [M+H]⁺.

¹H NMR (CDCl₃, 400 MHz): δ 8.34 (s, 1H), 8.06 (d, J=8.8 Hz, 1H), 7.57 (d, J=8.8 Hz, 1H), 3.98 (s, 3H), 3.32-3.26 (m, 1H), 1.38-1.33 (m, 2H), 1.22-1.18 (m, 2H).

Step 2

To a solution of 3 (134 mg, 0.80 mmol) in DMF (2 mL) was added 60% NaH in mineral oil (30 mg, 0.76 mmol) at room temperature. The resulting orange colored reaction stirred at room temperature for 30 min before adding a solution of 2 (100 mg, 0.40 mmol) in DMF (1 mL) dropwise at room temperature. The reaction stirred for 30 min at which point a sat. NH₄Cl solution (1 mL) was carefully added at 0° C. to quench the reaction. The workup was done using EtOAc, washing the EtOAc layer once with brine. The EtOAc layer was separated, dried using Na₂SO₄ and evaporated to give the crude product containing a mixture of 4 as a cis:trans mixture (~1:1) in addition to compound 5 as a cis:trans mixture (~1:1). This crude mixture of product was used directly for the next step without further purification. LC-MS $t_R$=Compound 4/1.706 min in 2 min chromatography; MS (ESI) m/z 383.25 [M+H]⁺.

Step 3

A solution of the crude mixture of compounds 4 and 5 (crude material used directly from previous step) was stirred in a solution of 2N NaOH (1 mL), MeOH (1 mL), and THF (2 mL) at room temperature for 24 hours. iPrOAc (5 mL) was added followed by 1 N NaOH (3 mL). The iPrOAc layer was separated and extracted again with 1 N NaOH. The aqueous layers were combined and acidified to pH ~4 at 0° C. using conc. HCl. The product (6) was then extracted into EtOAc (2 times, 5 mL each). The EtOAc layer was then dried using Na₂SO₄ and evaporated to afford crude product 6 (~1:1 cis:trans mixture of isomers), which was used directly for the next step without further purification. LC-MS $t_R$=1.536 min in 2 min chromatography; MS (ESI) m/z 369.22 [M+H]⁺.

Step 4

A solution of 6 (23 mg, 0.06 mmol), (R)-2-amino-2-(4-(ethylsulfonyl)phenyl)ethan-1-ol (21 mg, 0.06 mmol), EDC (13 mg, 0.06 mmol), iPr₂NEt (15 mg, 0.12 mmol) and HOBt (10 mg, 0.07 mmol) in DMF (1 mL) was stirred for 24 hours at room temperature. H₂O and EtOAc were added for the workup. The EtOAc layer was separated, dried using Na₂SO₄ and evaporated to give crude product 7. Purification by Gilson HPLC afforded 3.21 mg of the pure trans isomer of 7 as the TFA salt, which was less polar on the HPLC compared to the cis isomer of 7.

LC-MS $t_R$=trans isomer/1.455 min in 2 min chromatography; MS (ESI) m/z 580.51 [M+H]⁺. ¹H NMR (CD₃OD, 400 MHz): δ 8.67 (d, J=7.2 Hz, 1H), 7.87 (s, 1H), 7.79 (d, J=8.8 Hz, 2H), 7.69 (d, J=8.4 Hz, 1H), 7.60 (d, J=8.0 Hz, 2H), 7.43 (d, J=8.4 Hz, 1H), 5.22-5.17 (m, 1H), 4.88-4.80 (m, 1H), 3.82 (d, J=6.0 Hz, 2H), 3.09 (q, J=7.6 Hz, 2H), 3.07-3.02 (m, 1H), 2.32-2.29 (m, 2H), 2.22-2.15 (m, 1H), 2.02-1.99 (m, 2H), 1.63-1.42 (m, 4H), 1.10 (t, J=7.6 Hz, 3H), 1.08-1.06 (m, 2H), 0.94-0.90 (m, 2H). ¹⁹F NMR (CD₃OD, 400 MHz): δ −74.93 (d)

The following compounds are prepared using analogous procedures:

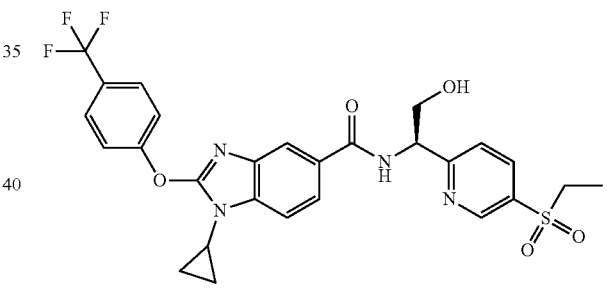

| Cpd | Cy² | L² | R² | R⁷ |
|---|---|---|---|---|
| BE-2 | trans-4-CF₃-cyclohexyl | O | Et | CH₂OH |
| BE-3 | trans-4-CF₃-cyclohexyl | O | c-Pr | H |
| BE-4.1ᵃ | trans-4-CF₃-cyclohexyl | O | i-Bu | H |
| BE-4.2ᵃ | cis-4-CF₃-cyclohexyl | O | i-Bu | H |
| BE-5 | 4-CF₃-phenyl | O | Et | H |
| BE-6 | 4-CF₃-phenyl | O | c-Pr | H |
| BE-7 | 4-CF₃-phenyl | O | c-Pr | CH₂OH |
| BE-8 | 4-CF₃-phenyl | O | Et | CH₂OH |
| BE-9 | 4-CF₃O-phenyl | O | Et | CH₂OH |
| BE-10 | 4-CF₃-phenyl | O | Et | CH₂NMe₂ |
| BE-11 | 4-CF₃-phenyl | O | Et | CH₂NH₂ |
| BE-12 | 4,4-difluorocyclohexyl | CH₂Oᵇ | Et | CH₂OH |
| BE-13 | 3,3-difluorocyclobutyl | CH₂Oᵇ | Et | CH₂OH |
| BE-14 | 4-CF₃-phenyl | CH₂Oᵇ | Et | CH₂OH |
| BE-15 | 4-CF₃-phenyl | CH₂Oᵇ | c-Pr | CH₂OH |
| BE-16 | 4,4-difluorocyclohexyl | CH₂Oᵇ | c-Pr | CH₂OH |
| BE-17 | cyclopropyl | CH₂Oᵇ | Et | CH₂OH |

ᵃIsomers were separated by chromatography.
ᵇCy² is attached to CH₂ and O is attached to the 2-position of the benzimidazole.

The following compound is prepared by using (R)-2-amino-2-(5-(ethylsulfonyl)pyridin-2-yl)ethan-1-ol in Step 4.

Compound BE-70

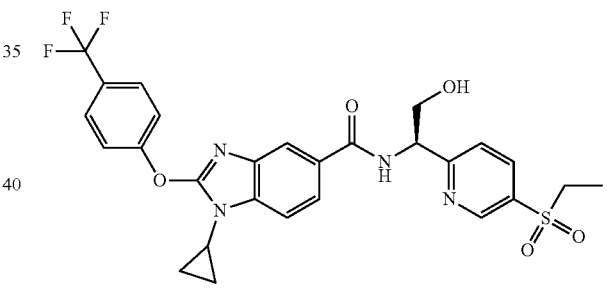

Example 4

1-cyclopropyl-N-(4-(ethylsulfonyl)benzyl)-2-((trans-4-(trifluoromethyl)cyclohexyl)methyl)-1H-benzo[d]imidazole-5-carboxamide (Compound BE-18.1) and 1-cyclopropyl-N-(4-(ethylsulfonyl)benzyl)-2-((cis-4-(trifluoromethyl)cyclohexyl)methyl)-1H-benzo[d]imidazole-5-carboxamide (Compound BE-18.2)

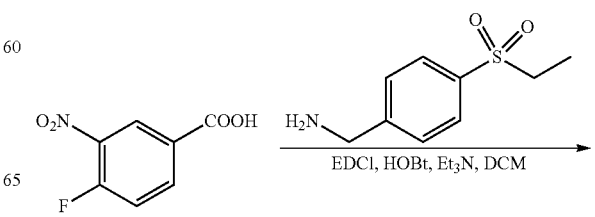

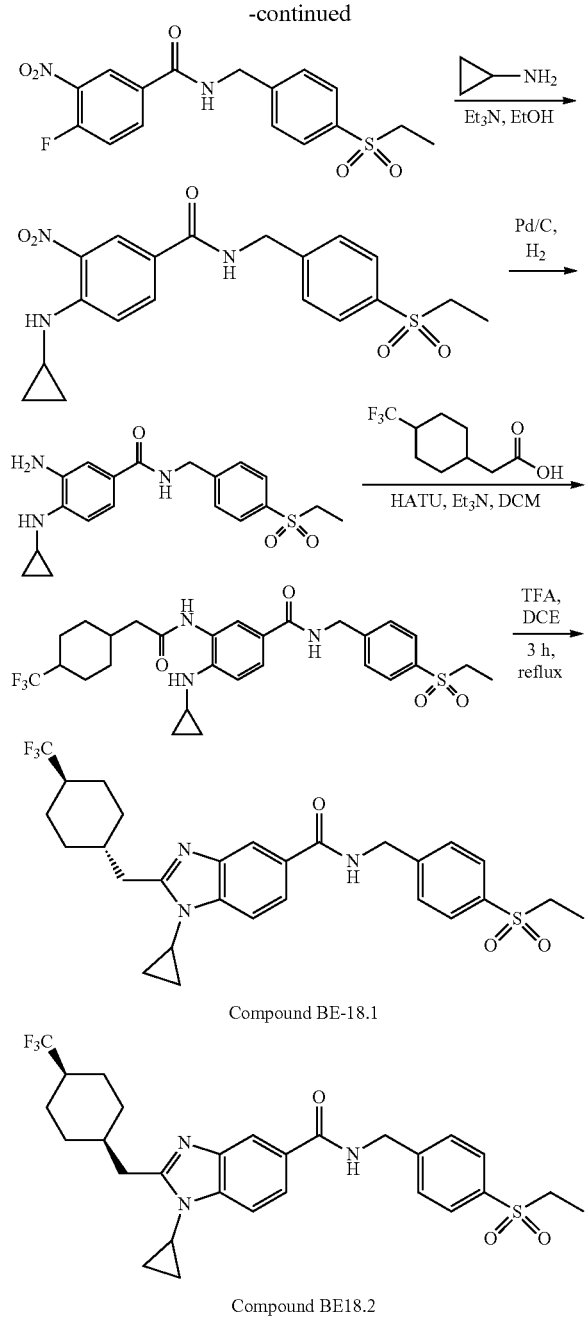

Compound BE-18.1

Compound BE18.2

Step 1

To a mixture of 4-fluoro-3-nitrobenzoic acid (4.3 g, 23.2 mmol) and (4-(ethylsulfonyl)phenyl)methanamine (2.3 g, 11.6 mmol) in anhydrous $CH_2Cl_2$ (120 mL) was added EDCI (4.4 g, 23.2 mmol), HOBt (3.1 g, 23.2 mmol) and $Et_3N$ (3.5 g, 34.8 mmol). The mixture was stirred at room temperature for 3 h under $N_2$ atmosphere. The mixture was quenched with $H_2O$ (100 mL). The aqueous layer was extracted with $CH_2Cl_2$ (3×100 mL). The combined organic layers were washed with brine (300 mL), dried over anhydrous $Na_2SO_4$, filtered and concentrated under reduced pressure. The residue was purified by column chromatography on silica gel eluting with petroleum ether/ethyl acetate 1/2 to afford N-(4-(ethylsulfonyl)benzyl)-4-fluoro-3-nitrobenzamide (4.0 g, 94%) as a yellow solid.

Step 2

To a mixture of N-(4-(ethylsulfonyl)benzyl)-4-fluoro-3-nitrobenzamide (2.0 g, 5.46 mmol) in EtOH (50 mL) was added cyclopropanamine (623 mg, 10.93 mmol) and $Et_3N$ (2.76 g, 27.3 mmol). The mixture was stirred at 70° C. under $N_2$ atmosphere for 3 h. The mixture was concentrated under reduced pressure. The residue was purified by column chromatography on silica gel eluting with $CH_2Cl_2$/MeOH 19/1 to afford 4-(cyclopropylamino)-N-(4-(ethylsulfonyl)benzyl)-3-nitrobenzamide (2.13 g, 97%) as a yellow solid.

Step 3

To a solution of 4-(cyclopropylamino)-N-(4-(ethylsulfonyl)benzyl)-3-nitrobenzamide (2.13 g, 5.3 mmol) in MeOH (50 mL) was added Pd/C (1.2 g, dry, 10% w/w). The mixture was stirred at room temperature under $H_2$ (30 psi) for 2 h. The mixture was filtered. The filtrate was concentrated under reduced pressure to afford crude 3-amino-4-(cyclopropylamino)-N-(4-(ethylsulfonyl)benzyl)benzamide (1.88 g, 95%) as a pale yellow solid, which was used for the next step without further purification. LC-MS $t_R$=0.691 min in 5-95 AB_1.5 min chromatography (Welch Merck RP-18e, 25-2 mm), MS (ESI) m/z 374.1 $[M+H]^+$.

Step 4

To a mixture of 3-amino-4-(cyclopropylamino)-N-(4-(ethylsulfonyl)benzyl)benzamide (213 mg, 0.57 mmol) and 2-(4-(trifluoromethyl)cyclohexyl)acetic acid (80 mg, 0.38 mmol) in anhydrous $CH_2Cl_2$ (4 mL) was added HATU (217 mg, 0.57 mmol) and $Et_3N$ (192 mg, 1.9 mmol). The mixture was stirred at room temperature for 3 h under $N_2$ atmosphere. The mixture was quenched with $H_2O$ (5 mL) and extracted with $CH_2Cl_2$ (3×5 mL). The combined organic layers were washed with brine (15 mL), dried over anhydrous $Na_2SO_4$, filtered and concentrated under reduced pressure. The residue was purified by column chromatography on silica gel eluting with petroleum ether/ethyl acetate=1/3 to afford 4-(cyclopropylamino)-N-(4-(ethylsulfonyl)benzyl)-3-(2-(4-(trifluoromethyl)cyclohexyl)acetamido)benzamide (260 mg, 100%) as a pale yellow oil. LC-MS $t_R$=0.888 min in 5-95 AB_1.5 min chromatography (Welch Merck RP-18e, 25-2 mm), MS (ESI) m/z 566.2 $[M+H]^+$.

Step 5

To a solution of 4-(cyclopropylamino)-N-(4-(ethylsulfonyl)benzyl)-3-(2-(4-(trifluoromethyl)cyclohexyl)acetamido)benzamide (130 mg, 0.23 mmol) in DCE (5 mL) was added TFA (0.5 mL). The mixture was stirred at 85° C. for 2 h under $N_2$ atmosphere. $H_2O$ (5 mL) was added and the mixture was extracted with $CH_2Cl_2$ (3×5 mL). The combined organic layers were washed with sat. aq. $NaHCO_3$ solution (15 mL), dried over anhydrous $Na_2SO_4$, filtered and concentrated under reduced pressure. The residue was purified by preparative TLC (petroleum ether/acetone=1/1), SFC separation (AD-H), basic preparative HPLC separation and then dry-freezing to afford 1-cyclopropyl-N-(4-(ethylsulfonyl)benzyl)-2-((trans-4-(trifluoromethyl)cyclohexyl)methyl)-1H-benzo[d]imidazole-5-carboxamide (BE-18.1, HCl salt, 21.8 mg, 31%) and 1-cyclopropyl-N-(4-(ethylsulfonyl)benzyl)-2-((cis-4-(trifluoromethyl)cyclohexyl)methyl)-1H-benzo[d]imidazole-5-carboxamide (BE-18.2, HCl salt, 7.5 mg, 11%) as white solids.

Before SFC Separation:

Isomer SFC $t_R$=4.144 and 5.392 min in 10 min chromatography (Column: AD-H; Method Name: AD-H_4_40_2_35ML.M, ee=53%).

SFC Separation Condition:
Instrument: Berger MultiGram™ SFC, Mettler Toledo Co, Ltd
Column: AD 250 mm*30 mm, 10 um
Mobile phase: A: Supercritical CO₂, B: iPrOH (0.05% NH₃H₂O), A:B=60:40 at 80 ml/min
Column Temp: 38° C.
Nozzle Pressure: 100 Bar
Nozzle Temp: 60° C.
Evaporator Temp: 20° C.
Trimmer Temp: 25° C.
Wavelength: 220 nm BE-18.1 LC-MS Method 2 $t_R$=0.803 min in 5-95AB_1.5 min chromatography (Welch Merck RP-18e 25-2 mm), MS (ESI) m/z 548.2 [M+H]⁺. ¹H NMR (CDCl₃, 400 MHz): δ 8.11 (s, 1H), 7.86 (d, J=8.4 Hz, 2H), 7.84 (d, J=8.0 Hz, 1H), 7.60-7.53 (m, 3H), 6.74 (t, J=5.6 Hz, 1H), 4.78 (d, J=5.6 Hz, 2H), 3.30-3.20 (m, 1H), 3.11 (q, J=7.6 Hz, 2H), 3.06 (d, J=7.6 Hz, 2H), 2.56-2.45 (m, 1H), 2.25-2.08 (m, 1H), 1.85-1.70 (m, 8H), 1.36-1.30 (m, 2H), 1.28 (t, J=7.6 Hz, 3H), 1.13-1.05 (m, 2H). Isomer SFC $t_R$=4.133 min in 10 min chromatography (Column: AD-H; Method Name: AD-H_4_40_2_35ML.M, ee=100%).

Basic Preparative HPLC Method:
Mobile phase A: water with 0.05% NH₃ H₂O solution
Mobile phase B: CH₃CN
Flow rate: 30 mL/min.
Detection: UV 220 nm
Column: Agela DuraShell C18 150*25*5 um
Column temperature: 40° C.

| Time in min | % A | % B |
|---|---|---|
| 0.00 | 54 | 46 |
| 8.00 | 24 | 76 |
| 8.20 | 0 | 100 |
| 10.00 | 0 | 100 |

BE-18.2 LC-MS Method 2 $t_R$=0.807 min in 5-95AB_1.5 min chromatography (Welch Merck RP-18e 25-2 mm), MS (ESI) m/z 548.1 [M+H]⁺. ¹H NMR (CDCl₃, 400 MHz): δ 8.11 (s, 1H), 7.87 (d, J=8.4 Hz, 2H), 7.84 (d, J=8.4 Hz, 1H), 7.60-7.54 (m, 3H), 6.74 (t, J=6.0 Hz, 1H), 4.78 (d, J=5.6 Hz, 2H), 3.30-3.20 (m, 1H), 3.11 (q, J=7.6 Hz, 2H), 2.95 (d, J=7.6 Hz, 2H), 2.20-1.90 (m, 6H), 1.43-1.31 (m, 4H), 1.28 (t, J=7.6 Hz, 3H), 1.23-1.03 (m, 4H). Isomer SFC $t_R$=5.360 min in 10 min chromatography (Column: AD-H; Method Name: AD-H_4_40_2.35ML.M, ee=99%).

Basic Preparative HPLC Method:
Mobile phase A: water with 0.05% NH₃ H₂O solution
Mobile phase B: CH₃CN
Flow rate: 30 mL/min.
Detection: UV 220 nm
Column: Agela DuraShell C18 150*25*5 um
Column temperature: 40° C.

| Time in min | % A | % B |
|---|---|---|
| 0.00 | 57 | 43 |
| 8.00 | 27 | 73 |
| 8.20 | 0 | 100 |
| 10.00 | 0 | 100 |

The following compounds are prepared using analogous procedures:

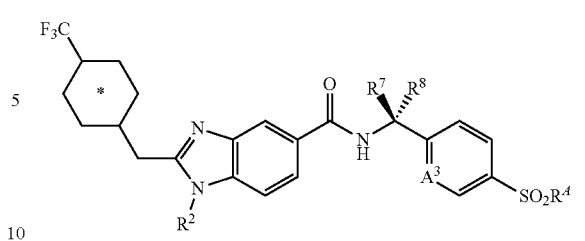

| Cpd No. | * | R² | R⁷ | R⁸ | A³ | R⁴ |
|---|---|---|---|---|---|---|
| BE-19.1[a] | trans | i-Bu | H | H | CH | Et |
| BE-19.2[a] | cis | i-Bu | H | H | CH | Et |
| BE-20 | trans | Et | H | H | CH | Et |
| BE-21 | trans | c-Pr | CH₂OH | H | CH | Et |
| BE-22 | trans | c-Pr | H | CH₂OH | CH | Et |
| BE-23 | trans | Et | CH₂OH | H | CH | Et |
| BE-24 | trans | Et | H | CH₂OH | CH | Et |
| BE-25 | trans | c-Pr | CH₂CH₂OH | H | CH | Et |
| BE-26.1[a] | trans | i-Bu | H | H | N | Et |
| BE-26.2[a] | cis | i-Bu | H | H | N | Et |
| BE-27.1[a] | trans | c-Pr | H | H | N | Et |
| BE-27.2[a] | cis | c-Pr | H | H | N | Et |
| BE-28 | trans | c-Pr | CH₂OH | H | N | Et |
| BE-29 | trans | c-Pr | H | CH₂OH | N | Et |
| BE-30 | trans | c-Pr | H | H | CH | Me |
| BE-31 | trans | c-Pr | H | H | N | NHMe |
| BE-32 | trans | c-Pr | CH₂OH | H | CH | Me |
| BE-33 | trans | c-Pr | H | H | CH | NHMe |

[a]Isomer pairs were separated by chromatography

The following compounds are prepared using analogous procedures:

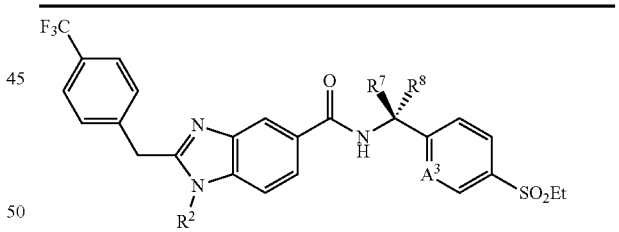

| Cpd No. | R² | R⁷ | R⁸ | A³ |
|---|---|---|---|---|
| BE-34 | Me | H | H | CH |
| BE-35 | Et | H | H | CH |
| BE-36 | c-Pr | H | H | CH |
| BE-37 | CF₃CH₂ | H | H | CH |
| BE-38 | c-Bu | H | H | CH |
| BE-39 | t-BuCH₂ | H | H | CH |
| BE-40 | i-Pr | H | H | N |
| BE-41 | i-Bu | H | H | CH |
| BE-42 | t-Bu | H | H | N |
| BE-43 | i-Bu | H | H | N |
| BE-44 | i-Bu | H | Me | CH |
| BE-45 | i-Bu | Me | H | CH |

The following compounds are prepared using analogous procedures:

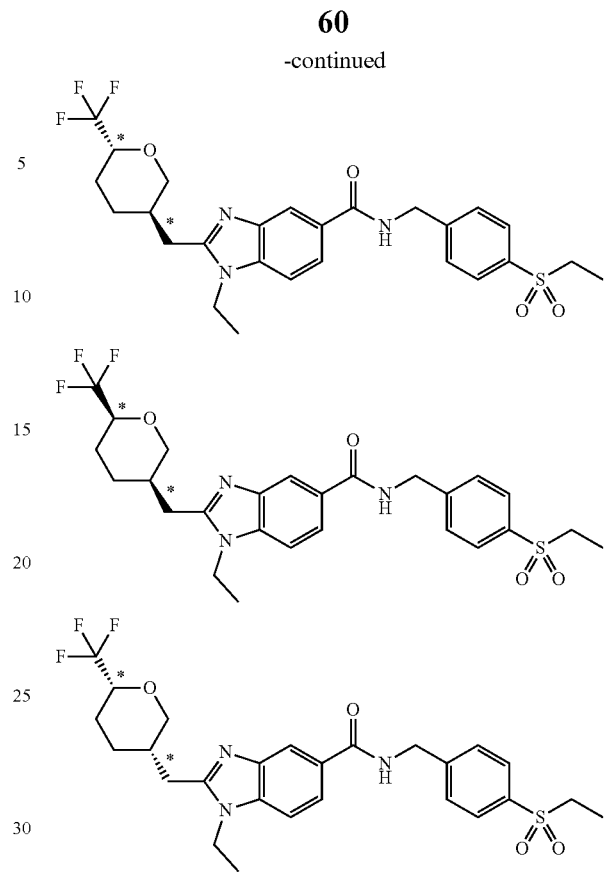

| Cpd No. | Cy2 | R² | R⁷ |
|---|---|---|---|
| BE-46.1[a] | trans-4-methoxycyclohexyl | c-Pr | H |
| BE-46.2[a] | cis-4-methoxycyclohexyl | c-Pr | H |
| BE-47 | 4-(trifluoromethoxy)phenyl | c-Pr | CH₂OH |
| BE-48 | 4-(difluoromethoxy)phenyl | c-Pr | H |
| BE-49 | 1-(t-butoxycarbonyl)piperidin-4-yl | c-Pr | H |
| BE-50 | 1-(2,2,2-trifluoroethyl)piperidin-4-yl | c-Pr | H |
| BE-51 | 6-(trifluoromethyl)pyridin-3-yl | c-Pr | H |
| BE-52 | 5-chloropyridin-2yl | c-Pr | H |
| BE-53 | 4-(trifluoromethyl)piperidin-1-yl | i-Bu | H |
| BE-54 | 4-(trifluoromethyl)piperidin-1-yl | c-Pr | CH₂OH |

[a]Isomers were separated by chromatography

The following compounds are prepared using analogous procedures:

Compound Nos BE-55.1 and -55.2

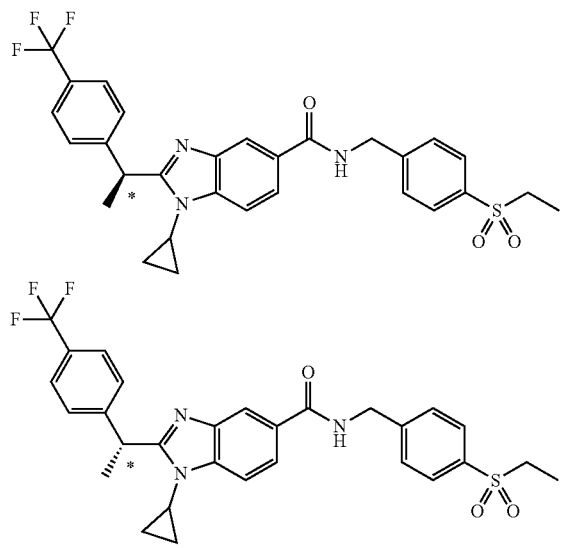

* isomers separated by chromatography, absolute configuration unknown

Compounds BE-56.1, -56.2, -56.3 and -56.4

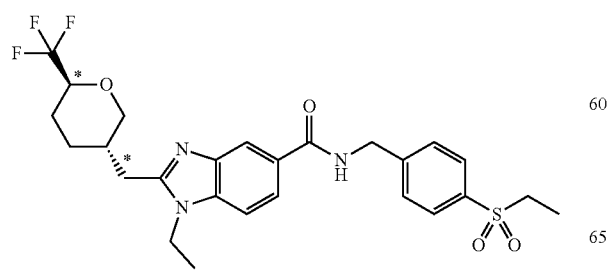

* isomers were separated by chromatography, absolute configuration unknown

Compounds BE-57.1, -57.2, -57.3 and -57.4

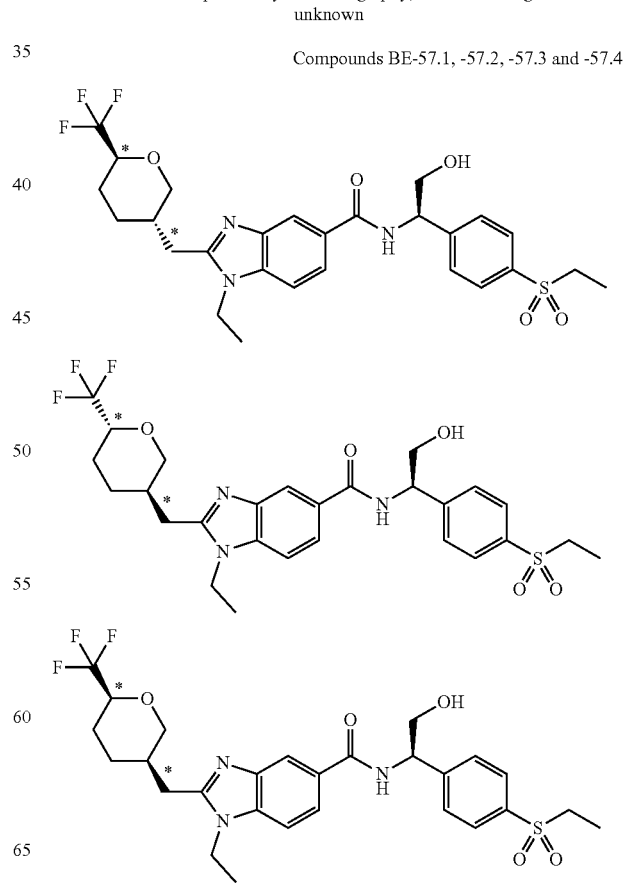

-continued
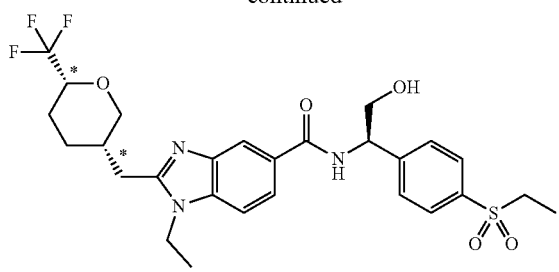
* isomers were separated by chromatography, absolute configuration unknown
Compound BE-58
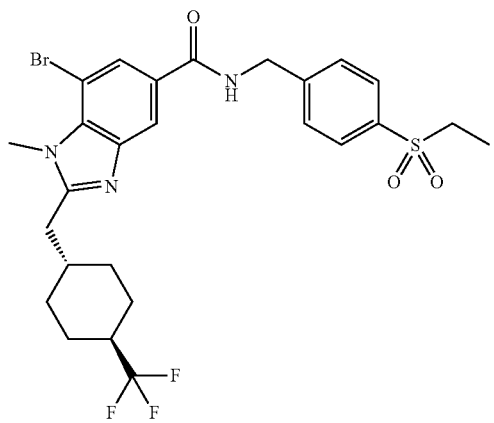
Compound BE-59
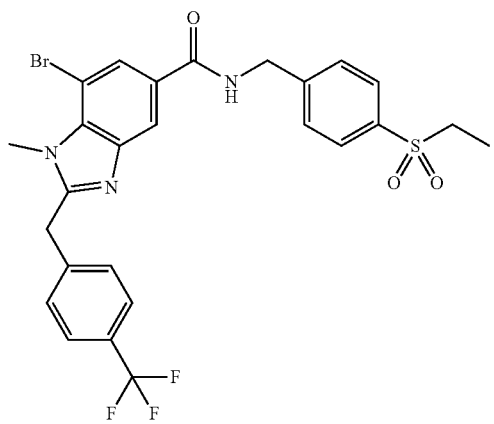
Compound BE-60
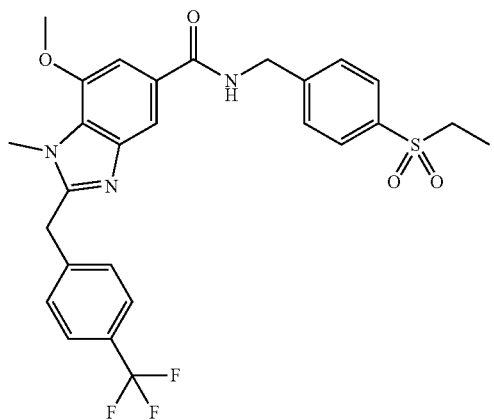
-continued
Compound BE-61
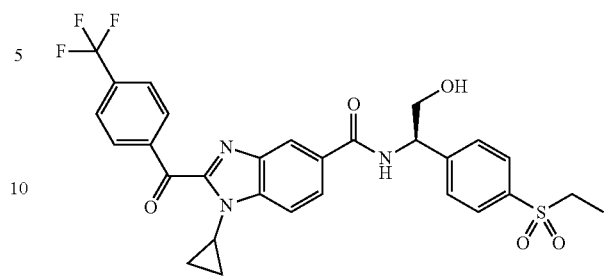
Compound BE-62
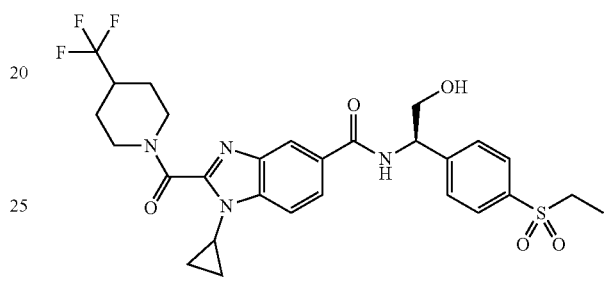
Compounds BE-63.1 and -63.2
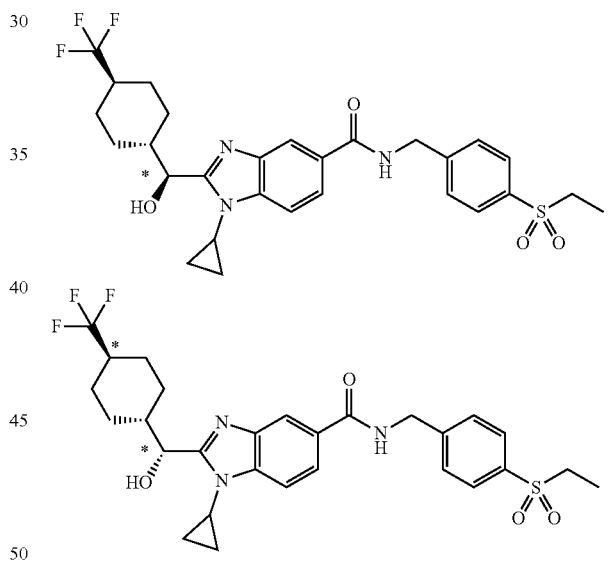
* isomers were separated by chromatography, absolute configuration unknown
The following compounds are prepared using analogous procedures:
Compound Nos BE-71.1 and -71.2
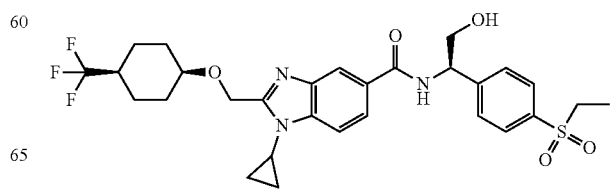

-continued

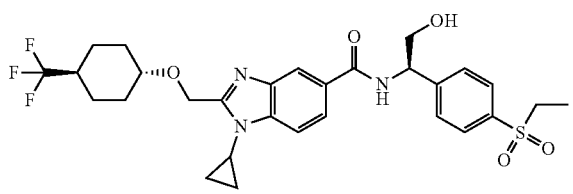

*isomers separated by chromatography, cis/trans configuration not assigned

Example 5

The following compounds were prepared from other compounds of Formula I:

Compound BE-64

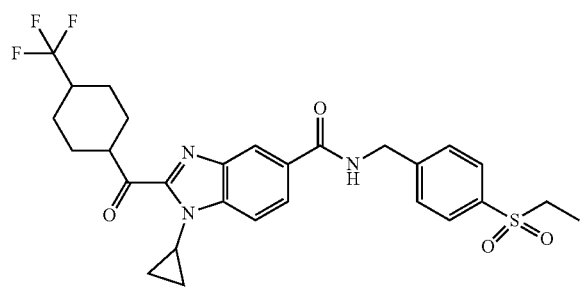

By oxidation of BE63.1 and -63.2 with MnO₂

Compound BE-65

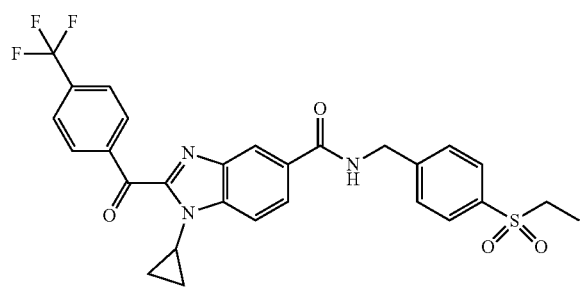

By oxidation of BE-36 with MnO₂

Compound BE-66

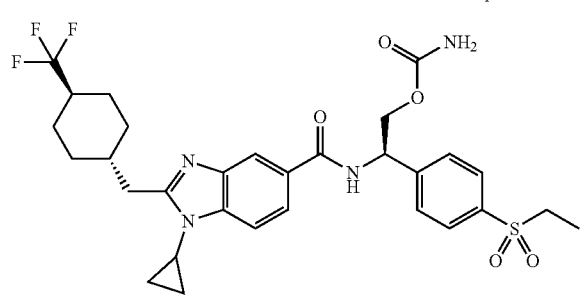

By reaction of BE-21 with Cl₃CC(=O)NCO, followed by treatment with K₂CO₃ in MeOH Compound BE-67

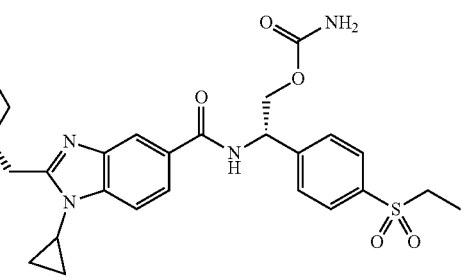

By reaction of BE-21 with Cl₃CC(=O)NCO, followed by treatment with K₂CO₃ in MeOH

Example 6

2-(4-(ethylsulfonyl)phenyl)-N-(1-iso butyl-2-(4-(trifluoromethyl)benzyl)-1H-benzo[d]imidazol-5-yl) acetamide (Compound BE-68)

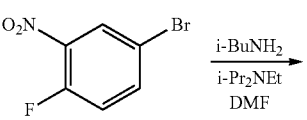

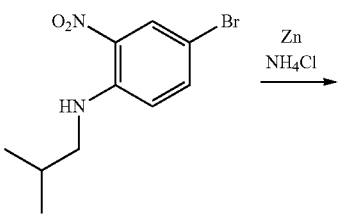

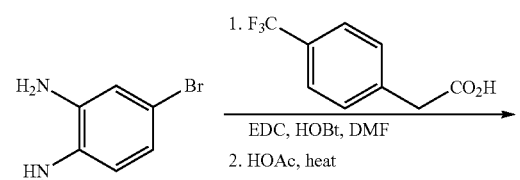

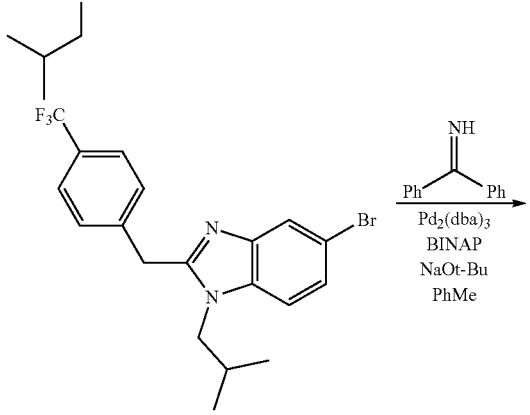

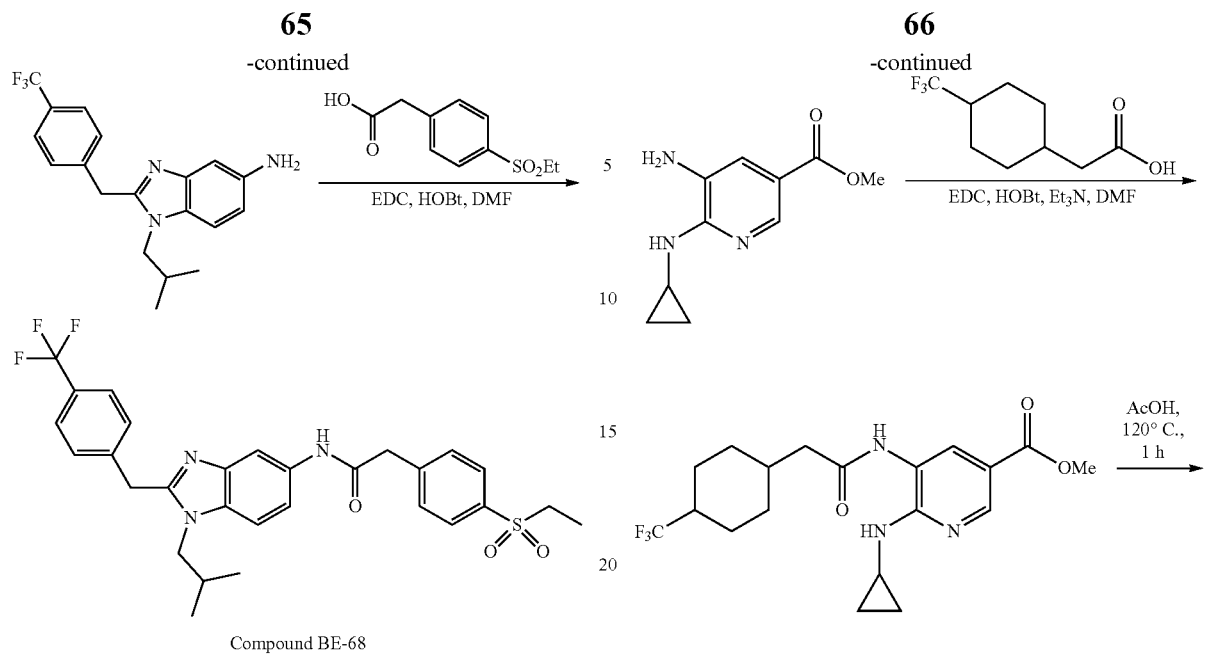
Compound BE-68
The following compounds is prepared using analogous procedures:
Compound BE-69
Example 7
3-cyclopropyl-N-(4-(ethylsulfonyl)benzyl)-2-((cis-4-(trifluoromethyl)cyclohexyl)methyl)-3H-imidazo[4,5-b]pyridine-6-carboxamide (Compound AB-1.2)
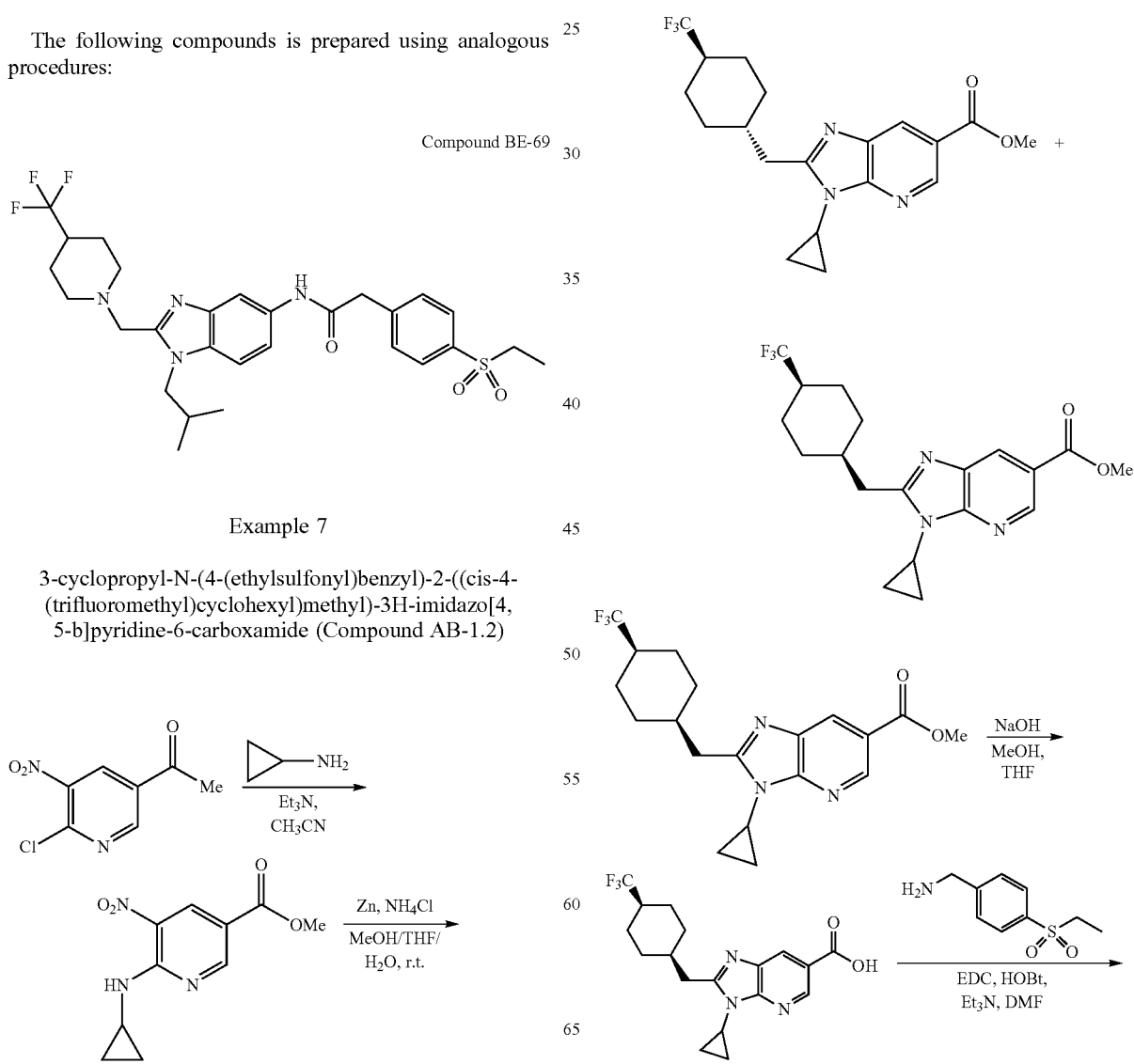

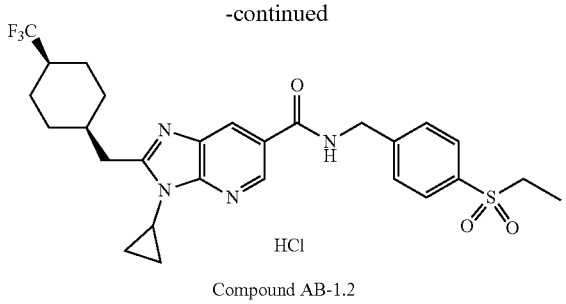

Compound AB-1.2

Step 1

To a solution of methyl 6-chloro-5-nitronicotinate (500 mg, 2.32 mmol) in CH$_3$CN (15 mL) was added cyclopropanamine (265 mg, 4.63 mmol) and Et$_3$N (585 mg, 5.78 mmol). The mixture was stirred at room temperature for 16 h. After concentrated under reduced pressure and added with water (5 mL), the mixture was extracted with ethyl acetate (3×5 mL). The combined organic layers were washed with brine (10 mL), dried over anhydrous Na$_2$SO$_4$, filtered, concentrated under reduced pressure to afford methyl 6-(cyclopropylamino)-5-nitronicotinate (550 mg, 100%) as a yellow solid.

Step 2

To a solution of methyl 6-(cyclopropylamino)-5-nitronicotinate (550 mg, 2.32 mmol) in MeOH/THF/H$_2$O (40 mL, v/v=1/1/1) was added Zn (1.5 g, 23.2 mmol) and NH$_4$Cl (1.25 g, 23.2 mmol). The resulting mixture was stirred at 25° C. for 4 h. The mixture was filtered and the filtrate was concentrated under reduced pressure. After added with water (15 mL), the mixture was extracted with ethyl acetate (3×15 mL). The combined organic layers were washed with brine (30 mL), dried over anhydrous Na$_2$SO$_4$, filtered, concentrated under reduced pressure and purified by chromatography column on silica gel eluting with petroleum ether:ethyl acetate=1:1 to give methyl 5-amino-6-(cyclopropylamino) nicotinate (480 mg, 100%) as a red oil.

Step 3

To a solution of methyl 5-amino-6-(cyclopropylamino) nicotinate (207 mg, 1.0 mmol) and 2-(4-(trifluoromethyl) cyclohexyl)acetic acid (210 mg, 1.0 mmol) in anhydrous DMF (8 mL) was added EDCI (287 mg, 1.5 mmol), HOBt (203 mg, 1.5 mmol) and Et$_3$N (303 mg, 3.0 mmol). The resulting mixture was stirred at room temperature for 16 h. After added with water (10 mL), the mixture was extracted with ethyl acetate (3×10 mL). The combined organic layers were washed with brine (20 mL), dried over anhydrous Na$_2$SO$_4$, filtered, concentrated under reduced pressure and purified by chromatography column on silica gel eluting with petroleum ether:ethyl acetate=1:1 to give methyl 6-(cyclopropylamino)-5-(2-(4-(trifluoromethyl)cyclohexyl)acetamido)nicotinate (260 mg, 65%) as a red oil. LC-MS t$_R$=0.795 min in 5-95 AB_1.5 min chromatography (Welch Xtimate MK RP-18e 25-2 mm), MS (ESI) m/z 400.0 [M+H]$^+$.

Step 4

Methyl 6-(cyclopropylamino)-5-(2-(4-(trifluoromethyl) cyclohexyl)acetamido)nicotinate (150 mg, 0.38 mmol) was dissolved in AcOH (10 mL). The resulting mixture was stirred at 120° C. for 1 h. The mixture was concentrated under reduced pressure. After added with water (10 mL) and adjusted to pH=7 by saturated NaHCO$_3$ solution (5 mL), the mixture was extracted with ethyl acetate (3×10 mL). The combined organic layers were washed with brine (20 mL), dried over anhydrous Na$_2$SO$_4$, filtered, concentrated under reduced pressure and purified by preparative TLC with petroleum ether:ethyl acetate=1:2 to give the low polarity spot methyl 3-cyclopropyl-2-((trans-4-(trifluoromethyl)cyclohexyl)methyl)-3H-imidazo[4,5-b]pyridine-6-carboxylate (50 mg, 35%) and the high polarity spot methyl 3-cyclopropyl-2-((cis-4-(trifluoromethyl)cyclohexyl)methyl)-3H-imidazo[4,5-b]pyridine-6-carboxylate (16 mg, 11%) as colorless oil. LC-MS t$_R$=0.897 min in 5-95 AB_1.5 min chromatography (Welch Xtimate MK RP-18e 25-2 mm), MS (ESI) m/z 382.1 [M+H]$^+$.

Step 5

To a solution of methyl 3-cyclopropyl-2-((cis-4-(trifluoromethyl)cyclohexyl)methyl)-3H-imidazo[4,5-b]pyridine-6-carboxylate (16 mg, 0.042 mmol) in anhydrous THF/MeOH (2 mL, v/v=1/1) was added NaOH (0.7 mL, 1N in H$_2$O). The resulting mixture was stirred at room temperature for 2 h. The mixture was concentrated under reduced pressure. After adjusted to pH=4 with 4N HCl solution, the mixture was extracted with ethyl acetate (3×2 mL). The combined organic layers were washed with brine (5 mL), dried over anhydrous Na$_2$SO$_4$, filtered, concentrated under reduced pressure to give 3-cyclopropyl-2-((cis-4-(trifluoromethyl)cyclohexyl)methyl)-3H-imidazo[4,5-b]pyridine-6-carboxylic acid (15 mg, 100%) as a white solid. LC-MS t$_R$=0.712 min in 5-95 AB_1.5 min chromatography (Welch Xtimate MK RP-18e 25-2 mm), MS (ESI) m/z 367.9 [M+H]$^+$.

Step 6

To a solution of 3-cyclopropyl-2-((cis-4-(trifluoromethyl) cyclohexyl)methyl)-3H-imidazo[4,5-b]pyridine-6-carboxylic acid (15 mg, 0.042 mmol) and (4-(ethylsulfonyl)phenyl) methanamine (25 mg, 0.126 mmol) in anhydrous DMF (2 mL) was added EDCI (40 mg, 0.21 mmol), HOBt (29 mg, 0.21 mmol) and Et$_3$N (42 mg, 0.42 mmol). The resulting mixture was stirred at room temperature for 16 h. After added with water (3 mL), the mixture was extracted with CH$_2$Cl$_2$ (3×5 mL). The combined organic layers were washed with brine (3×10 mL), dried over anhydrous Na$_2$SO$_4$, filtered, concentrated under reduced pressure and purified by preparative TLC with ethyl acetate, then HCl preparative HPLC separation to give 3-cyclopropyl-N-(4-(ethylsulfonyl)benzyl)-2-((cis-4-(trifluoromethyl)cyclohexyl)methyl)-3H-imidazo[4,5-b]pyridine-6-carboxamide (AB-1.2, HCl salt, 9.3 mg, 38%) as a pale yellow solid. AB-1.2 (HCl salt) LC-MS t$_R$=0.852 min in 5-95 AB_1.5 min chromatography (Welch Xtimate MK RP-18e 25-2 mm), MS (ESI) m/z 549.1 [M+H]$^+$. $^1$H NMR (CD$_3$OD 400 MHz): δ 9.13 (d, J=2.0 Hz, 1H), 8.60 (d, J=2.0 Hz, 1H), 7.89 (d, J=8.4 Hz, 2H), 7.67 (d, J=8.4 Hz, 2H), 4.75 (s, 2H), 3.63-3.55 (m, 1H), 3.28 (d, J=7.2 Hz, 2H), 3.20 (q, J=7.2 Hz, 2H), 2.24-2.06 (m, 2H), 2.05-1.93 (m, 4H), 1.50-1.25 (m, 9H), 1.21 (t, J=7.6 Hz, 3H). Isomer SFC t$_R$=4.82 min in 16 min chromatography (Column: AD-H; Method Name: AD-H_3UM_4_40_2.5ML.met, ee=96.27%).

HCl Preparative HPLC Method:
Mobile phase A: water with 0.1% HCl solution
Mobile phase B: CH$_3$CN
Flow rate: 25 mL/min.
Detection: UV 220 nm/254 nm
Column: Gemini 150*25 mm*5 um
Column temperature: 30° C.

| Time in min | % A | % B |
| --- | --- | --- |
| 0.00 | 40 | 60 |
| 10.00 | 96 | 4 |
| 10.20 | 0 | 100 |
| 12.00 | 0 | 100 |

The following compounds are prepared using analogous procedures:

Compound AB-2

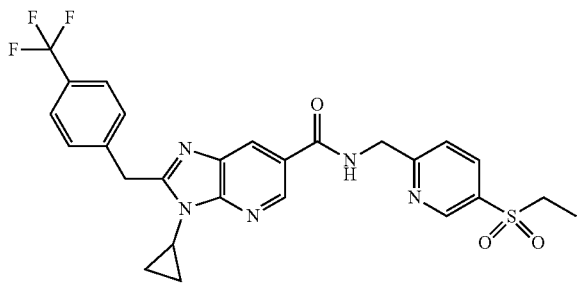

CompoundAB-3

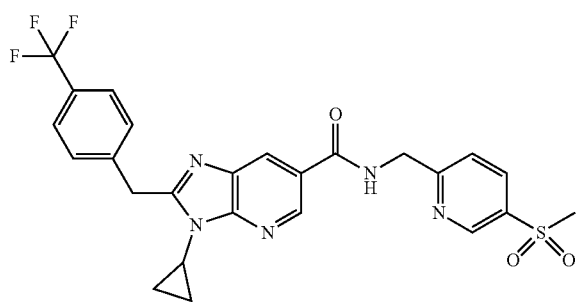

Example 8

(R)-1-ethyl-N-(1-(4-(ethylsulfonyl)phenyl)-2-hydroxyethyl)-2-((4-(trifluoromethyl)piperidin-1-yl)methyl)-1H-indole-5-carboxamide (Compound IN-10)

Step 1. 5-bromo-1-ethyl-1H-indole-2-carbaldehyde

A mixture of 5-bromo-1H-indole-2-carbaldehyde (0.6420 g, 2.86 mmol), $Cs_2CO_3$ (4.060 g, 12.5 mmol), and EtI (1.0 mL, 12.5 mmol) in DMF (10 mL) was stirred at room temperature for 2 d. The reaction mixture was then quenched with saturated $NH_4Cl$ and extracted twice with ethyl acetate. The combined organic layers were dried over $Na_2SO_4$ and evaporated. The residue was purified by flash chromatography on silica gel eluted with 0-40% ethyl acetate/hexanes to give 0.6775 g (94%) of 5-bromo-1-ethyl-1H-indole-2-carbaldehyde. LC-MS Method 1 $t_R$=1.71 min, m/z 252, 254 (MH$^+$); $^1$H NMR (CD$_3$OD, 400 MHz) δ 9.86 (s, 1H), 7.89 (s, 1H), 7.48 (m, 2H), 7.33 (s, 1H), 4.60 (q, J=7.16 Hz, 2H), 1.33 (t, J=7.22 Hz, 3H).

Step 2. 5-bromo-1-ethyl-2-((4-(trifluoromethyl)piperidin-1-yl)methyl)-1H-indole

A mixture of 5-bromo-1-ethyl-1H-indole-2-carbaldehyde (0.4022 g, 1.60 mmol), 4-(trifluoromethyl)piperidine (0.5120, 3.34 mmol), and NaBH(OAc)$_3$ (0.7330 g, 3.46 mmol) in 1,2-dichloroethane (15 mL) was stirred at room temperature for 23 h. The reaction mixture was then quenched with saturated NaHCO$_3$ and extracted three times with dichloromethane. The combined organic layers were dried over Na$_2$SO$_4$ and evaporated. The residue was purified by flash chromatography on silica gel eluted with 0→4% MeOH/DCM to afford 0.5769 g (93%) of 5-bromo-1-ethyl-2-((4-(trifluoromethyl)piperidin-1-yl)methyl)-1H-indole. LC-MS Method 1 $t_R$=1.12 min, m/z 389, 391 (MH$^+$), 236, 238 (M$^+$−152); $^1$H NMR (CD$_3$OD, 400 MHz) δ 7.76 (s, 1H), 7.44 (d, J=8.78 Hz, 1H), 7.35 (d, J=8.78 Hz, 1H), 6.77 (s, 1H), 4.61 (s, 2H), 4.36 (q, J=7.13 Hz, 2H), 3.71-3.68 (m, 2H), 3.20-3.14 (m, 2H), 2.63-2.59 (m, 1H), 2.19-2.15 (m, 2H), 1.94-1.77 (m, 2H), 1.31 (t, J=7.18 Hz, 3H); $^{19}$F NMR (CD$_3$OD, 376 MHz) δ −75.56.

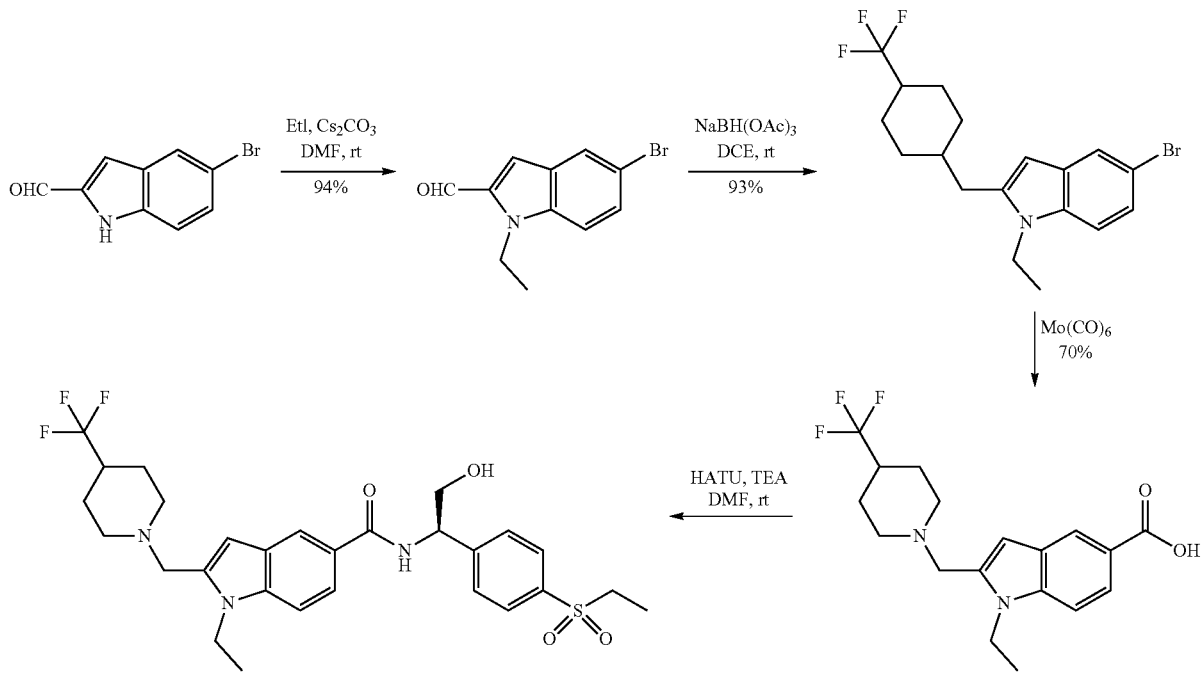

Step 3. 1-ethyl-2-((4-(trifluoromethyl)piperidin-1-yl)methyl)-1H-indole-5-carboxylic acid A mixture of 5-bromo-1-ethyl-2-((4-(trifluoromethyl)piperidin-1-yl)methyl)-1H-indole (0.3196 g, 0.821 mmol), Molybdenumhexacarbonyl (0.3835 g, 1.45 mmol), Herrmann's palladacycle (0.1550 g, 0.165 mmol), Tri-tert-butylphosphonium tetrafluoroborate (0.1595 g, 0.550 mmol), water (0.4 mL), and DBU (0.4 mL) in dioxane (4 mL) was heated in microwave at 150° C. for 20 min. The reaction mixture was purified by reverse-phase HPLC (Phenomenex® Luna 5μ $C_{18}$ (2) 250×21.20 mm column, 10% $CH_3CN/H_2O$, 0.1% $CF_3COOH$ over 1.5 min, 10%→90% $CH_3CN/H_2O$, 0.1% $CF_3COOH$ over 8 min, and then 90% $CH_3CN/H_2O$, 0.1% $CF_3COOH$ over 4 min, flow rate 25 mL/min) to yield 0.2676 g (70%) of 1-ethyl-2-((4-(trifluoromethyl)piperidin-1-yl)methyl)-1H-indole-5-carboxylic acid as a TFA salt. LC-MS Method 1 $t_R$=0.78 min, m/z 355 (MH$^+$), 202 (M$^+$−152); $^1$H NMR (CD$_3$OD, 400 MHz) δ 8.38-8.37 (m, 1H), 7.96 (dd, J=8.79, 0.88 Hz, 1H), 7.57 (d, J=8.79 Hz, 1H), 6.93 (s, 1H), 4.63 (s, 2H), 4.41 (q, J=7.13 Hz, 2H), 3.73-3.70 (m, 2H), 3.20-3.13 (m, 2H), 2.66-2.58 (m, 1H), 2.21-2.18 (m, 2H), 1.85-1.80 (m, 2H), 1.35 (t, J=7.18 Hz, 3H); $^{19}$F NMR (CD$_3$OD, 376 MHz) δ −75.58.

Step 4. (R)-1-ethyl-N-(1-(4-(ethylsulfonyl)phenyl)-2-hydroxyethyl)-2-((4-(trifluoromethyl)piperidin-1-yl)methyl)-1H-indole-5-carboxamide A mixture of 1-ethyl-2-((4-(trifluoromethyl)piperidin-1-yl)methyl)-1H-indole-5-carboxylic acid (0.0495 g, 0.106 mmol), (R)-2-amino-2-(4-(ethylsulfonyl)phenyl)ethan-1-ol (0.0516 g, 0.194 mmol), HATU (0.2154 g, 0.566 mmol), and Et$_3$N (0.3 mL) in DMF (1.5 mL) was stirred at room temperature for 2 h. The reaction mixture was purified by reverse-phase HPLC (Phenomenex® Luna 5μ $C_{18}$ (2) 250×21.20 mm column, 10% $CH_3CN/H_2O$, 0.1% $CF_3COOH$ over 1.5 min, 10%→90% $CH_3CN/H_2O$, 0.1% $CF_3COOH$ over 8 min, and then 90% $CH_3CN/H_2O$, 0.1% $CF_3COOH$ over 4 min, flow rate 25 mL/min) and the fractions were then lyophilized to afford (R)-1-ethyl-N-(1-(4-(ethylsulfonyl)phenyl)-2-hydroxyethyl)-2-((4-(trifluoromethyl)piperidin-1-yl)methyl)-1H-indole-5-carboxamide TFA salt as a white fluffy solid. LC-MS Method 1 $t_R$=0.82 min, m/z 566 (MH$^+$); $^1$H NMR (CD$_3$OD, 400 MHz) δ 8.72 (d, J=7.03 Hz, 1H), 8.25 (m, 1H), 7.89 (d, J=8.20 Hz, 2H), 7.85 (dd, J=8.79, 0.87 Hz, 1H), 7.70 (d, J=8.20 Hz, 2H), 7.60 (d, J=8.79 Hz, 1H), 6.94 (s, 1H), 5.33-5.28 (m, 1H), 4.64 (s, 2H), 4.42 (q, J=7.13 Hz, 2H), 3.93 (d, J=6.15 Hz, 2H), 3.74-3.71 (m, 2H), 3.22-3.16 (m, 4H), 2.64-2.59 (m, 1H), 2.22-1.19 (m, 2H), 1.83-1.79 (m, 2H), 1.35 (t, J=7.18 Hz, 3H), 1.21 (t, J=7.46 Hz, 3H); $^{19}$F NMR (CD$_3$OD, 376 MHz) δ −75.58.

The following compound is prepared by a similar procedure using (R)-2-amino-2-(5-(ethylsulfonyl)pyridin-2-yl)ethan-1-ol in Step 4.

Compound IN-11

The following compounds are prepared from 5-bromo-1-cyclopropyl-1H-indole-2-carbaldehyde using procedures similar to those in Steps 2-4.

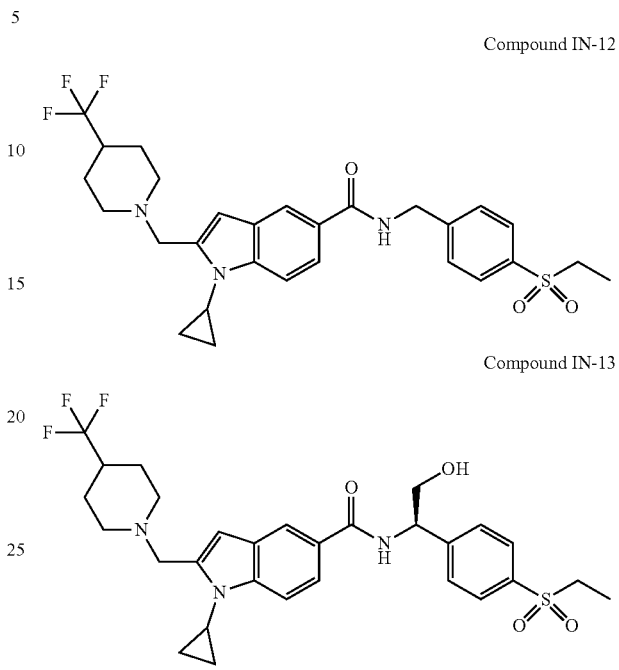

Compound IN-12

Compound IN-13

The starting material for Step 2 for the preparation of these compounds was prepared as shown in below in Alternate Step 1.

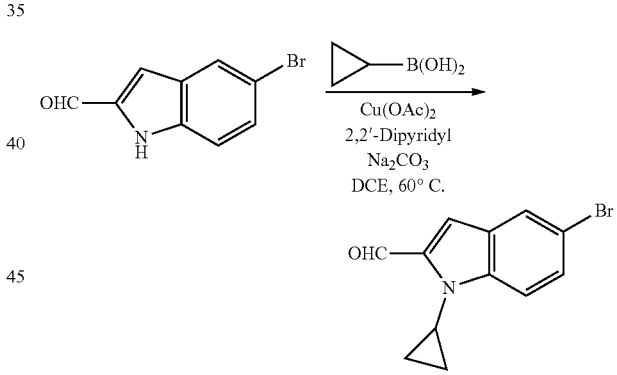

Alternate Step 1:
5-Bromo-1-cyclopropyl-1H-indole-2-carbaldehyde

A mixture of 5-bromo-1H-indole-2-carbaldehyde (0.3482 g, 1.55 mmol), cyclopropylboronic acid (0.2948 g, 3.43 mmol), Cu(OAc)$_2$ (0.2930 g, 1.61 mmol), 2,2'-dipyridyl (0.2490 g, 1.59 mmol), and Na$_2$CO$_3$ (0.5135 g, 4.84 mmol) in dichloroethane (15 mL) was vigorously stirred at 60° C. for 3 h under air. The reaction mixture was cooled to room temperature, and then quenched with saturated NH$_4$Cl and extracted twice with dichloromethane. The combined organic layers were dried over Na$_2$SO$_4$ and evaporated. The residue was purified by flash chromatography on silica gel eluted with 0-80% ethyl acetate/hexanes to afford 0.3690 g (90%) of 5-bromo-1-cyclopropyl-1H-indole-2-carbaldehyde. LC-MS Method 1 $t_R$=1.70 min, m/z 264, 266 (MH$^+$).

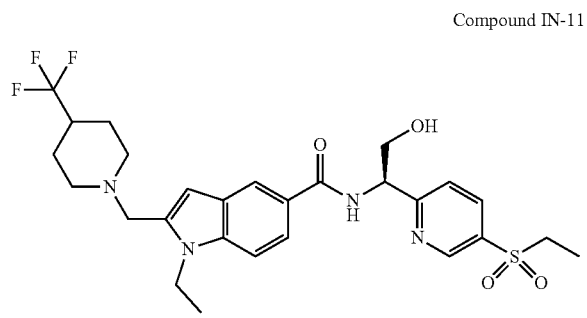 [SMILES: CCn1c(CN2CCC(C(F)(F)F)CC2)cc2cc(C(=O)N[C@@H](CO)c3ccc(S(=O)(=O)CC)cn3)ccc21]

Example 9

1-ethyl-N—((R)-1-(5-(ethylsulfonyl)pyridin-2-yl)-2-hydroxyethyl)-2-(((trans)-4-(trifluoromethyl)cyclohexyl)methyl)-1H-indole-5-carboxamide and 1-ethyl-N—((R)-1-(5-(ethylsulfonyl)pyridin-2-yl)-2-hydroxyethyl)-2-(((cis)-4-(trifluoromethyl)cyclohexyl)methyl)-1H-indole-5-carboxamide (Compounds IN-14.1and -14.2))

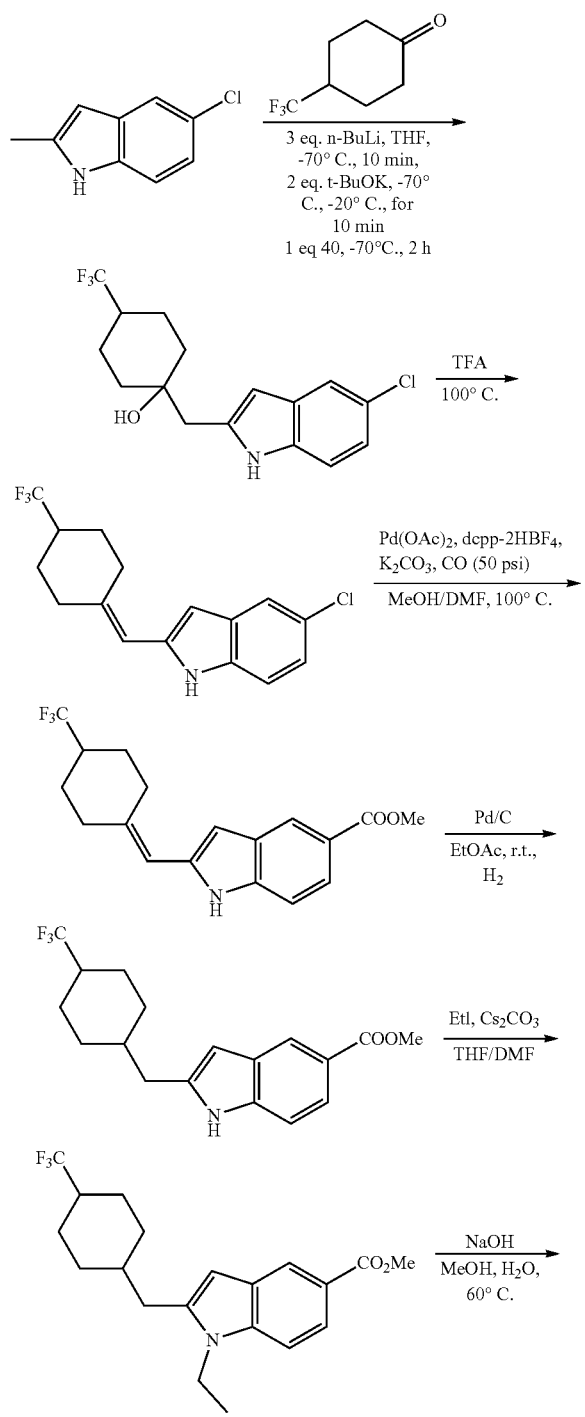

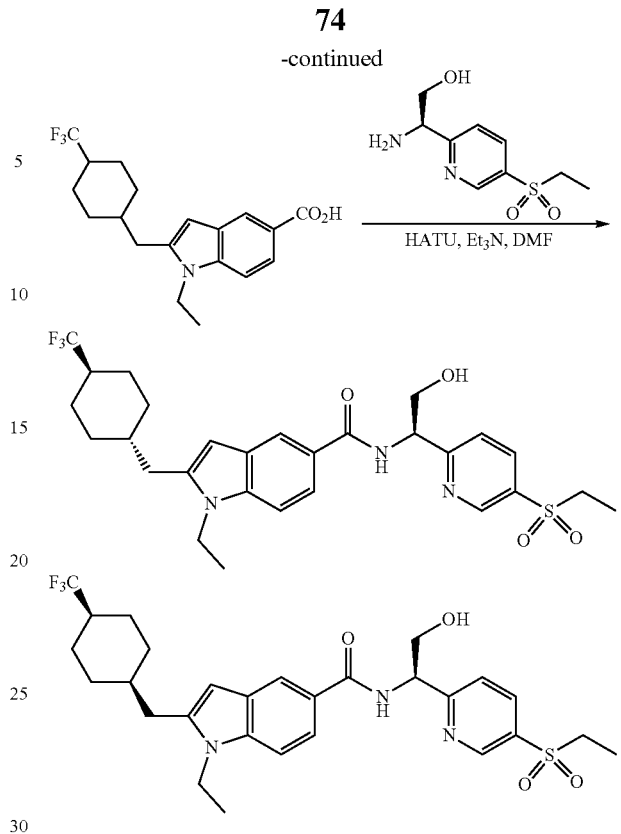

Step 1

To a solution of 5-chloro-2-methyl-1H-indole (1.5 g, 9.1 mmol) in anhydrous THF (20 mL) was added n-BuLi (11 mL, 27.5 mmol, 2.5 M in hexane) dropwise at −70° C. under $N_2$. The mixture was stirred at −70° C. under $N_2$ for 10 min, followed by adding t-BuOK (18 mL, 18 mmol, 1 M in THF) dropwise. The mixture was allowed to warm to −30° C. and stirred for 10 min, then cooled to −70° C. A solution of 4-(trifluoromethyl)cyclohexanone (1.7 g, 10.2 mmol) in anhydrous THF (10 mL) was added dropwise. The mixture was stirred at −70° C. under $N_2$ for 2 h. TLC (petroleum ether:ethyl acetate=5:1) showed 5-chloro-2-methyl-1H-indole was still remained and two new spot was found. The mixture was quenched with sat. $NH_4Cl$ solution (10 mL), added $H_2O$ (20 mL) and extracted with ethyl acetate (3×30 mL). The combined organic layers were dried over anhydrous $Na_2SO_4$, filtered and concentrated under reduced pressure. The residue was purified by column chromatography on silica gel eluting with petroleum ether:ethyl acetate=10:1-5:1 to afford 1-((5-chloro-1H-indol-2-yl)methyl)-4-(trifluoromethyl)cyclohexanol (1.2 g, 39%) as a pale yellow solid.

Step 2

The solution of 1-((5-chloro-1H-indol-2-yl)methyl)-4-(trifluoromethyl)cyclohexanol (1.2 g, 3.6 mmol) in TFA (3 mL) was heated to 100° C. and stirred for 2 h. TLC (petroleum ether:ethyl acetate=5:1) showed the reaction was completed. The mixture was adjusted to pH=7-8 by sat. $NaHCO_3$ solution and extracted with ethyl acetate (3×30 mL). The combined organic layers were dried over anhydrous $Na_2SO_4$, filtered and concentrated under reduced pressure. The residue was purified by column chromatography on silica gel eluting with petroleum ether:ethyl acetate=20:1 to afford 5-chloro-2-((4-(trifluoromethyl)cyclohexylidene)methyl)-1H-indole (600 mg, 55%) as a yellow solid.

LC-MS $t_R$=5.010 min in 10-80AB_7.0 min chromatography (Welch Xtimate 3 um, C18, 2.1*30 mm), MS (ESI) m/z 313.9 [M+H]$^+$.

Step 3

To a solution of 5-chloro-2-((4-(trifluoromethyl)cyclohexylidene)methyl)-1H-indole (1 g, 3.2 mmol) in anhydrous DMF (15 mL) and anhydrous MeOH (20 mL) was added Pd(OAc)$_2$ (150 mg, 0.64 mmol), dcpp-2BF$_4$ (390 mg, 0.64 mmol) and K$_2$CO$_3$ (1.3 g, 9.4 mmol) under N$_2$, followed bubbled with CO (15 psi) for 10 min and stirred at 100° C. for 16 h under CO (50 psi). LCMS showed the desired product was found. The mixture was filtered, added H$_2$O (30 mL) and extracted with EtOAc (3×30 mL). The combined organic layers were washed with H$_2$O (3×50 mL). The organic layer was dried over anhydrous Na$_2$SO$_4$, filtered and concentrated under reduced pressure. The residue was purified by column chromatography on silica gel eluting with petroleum ether:ethyl acetate=10:1 to afford methyl 2-((4-(trifluoromethyl) cyclohexylidene)methyl)-1H-indole-5-carboxylate (300 mg, 28%) as a yellow solid. LC-MS $t_R$=4.475 min in 10-80 AB_7.0 min chromatography (Welch Xtimate 3 um, C18, 2.1*30 mm), MS (ESI) m/z 337.9 [M+H]$^+$.

Step 4

To a solution of methyl 2-((4-(trifluoromethyl)cyclohexylidene)methyl)-1H-indole-5-carboxylate (300 mg, 0.89 mmol) in ethyl acetate (5 mL) was added Pd/C (50 mg, 10% wt) under H$_2$. The mixture was stirred at room temperature for 2 h under H$_2$ (15 psi). LCMS showed the reaction was completed. The mixture was filtered and concentrated under reduced pressure to afford crude methyl 2-((4-(trifluoromethyl)cyclohexyl)methyl)-1H-indole-5-carboxylate (280 mg, 93%) as a yellow solid, which was used for next step without further purification. LC-MS Method 2 $t_R$=0.885 min in 5-95 AB_1.5 min chromatography (Welch RP-18e, 25-2 mm), MS (ESI) m/z 339.9 [M+H]$^+$.

Step 5

To a solution of methyl 2-((4-(trifluoromethyl)cyclohexyl)methyl)-1H-indole-5-carboxylate (280 mg, 0.83 mmol) in anhydrous THF (5 mL) and DMF (5 mL) was added Cs$_2$CO$_3$ (850 mg, 2.61 mmol) and EtI (480 mg, 2.61 mmol) under N$_2$. The mixture was stirred at 60° C. for 5 h under N$_2$. TLC (petroleum ether:ethyl acetate=5:1) showed the reaction was completed. The mixture was added with EtOAc (10 mL) and washed with H$_2$O (3×10 mL). The organic layer was dried over anhydrous Na$_2$SO$_4$, filtered and concentrated under reduced pressure, The residue was purified by column chromatography on silica gel eluting with petroleum ether:ethyl acetate=10:1 to afford methyl 1-ethyl-2-((4-(trifluoromethyl)cyclohexyl)methyl)-1H-indole-5-carboxylate (230 mg, 76%) as a yellow oil. LC-MS Method 2 $t_R$=0.912 min in 5-95AB_1.5 min chromatography (Welch RP-18e, 25-21 mm), MS (ESI) m/z 368.0 [M+H]$^+$.

Step 6

To a solution of methyl 1-ethyl-2-((4-(trifluoromethyl) cyclohexyl)methyl)-1H-indole-5-carboxylate (230 mg, 0.63 mmol) in MeOH (5 mL) was added NaOH solution (1.5 mL, 3.0 mmol, 2 M in H$_2$O). The mixture was stirred at 60° C. for 20 h. TLC (petroleum ether:ethyl acetate=5:1) showed the reaction was completed. The mixture was adjusted to pH=5-6 by HCl solution (2 M in H$_2$O) and extracted with EtOAc (3×5 mL). The combined organic layers were dried over anhydrous Na$_2$SO$_4$, filtered and concentrated under reduced pressure to afford crude 1-ethyl-2-((4-(trifluoromethyl)cyclohexyl)methyl)-1H-indole-5-carboxylic acid (200 mg, 90%) as a yellow solid, which was used for next step without further purification.

Step 7

To a solution of 1-ethyl-2-((4-(trifluoromethyl)cyclohexyl)methyl)-1H-indole-5-carboxylic acid (60 mg, 0.17 mmol) and (R)-2-amino-2-(5-(ethylsulfonyl)pyridin-2-yl) ethanol (90 mg, 0.34 mmol) in DMF (3 mL) was added Et$_3$N (52 mg, 0.51 mmol) and HATU (195 mg, 0.51 mmol). The mixture was stirred at 12° C. for 16 h. LCMS showed the reaction was completed. The mixture was added EtOAc (10 mL) and washed with H$_2$O (3×10 mL). The organic layer was dried over anhydrous Na$_2$SO$_4$, filtered and concentrated under reduced pressure. The residue was purified by preparative TLC with ethyl acetate to afford a mixture of -ethyl-N—((R)-1-(5-(ethylsulfonyl)pyridin-2-yl)-2-hydroxyethyl)-2-(((trans)-4-(trifluoromethyl)cyclohexyl) methyl)-1H-indole-5-carboxamide and 1-ethyl-N—((R)-1-(5-(ethylsulfonyl)pyridin-2-yl)-2-hydroxyethyl)-2-(((cis)-4-(trifluoromethyl)cyclohexyl)methyl)-1H-indole-5-carboxamide (100 mg, 104%) as a yellow solid. The mixture was separated by SFC followed by basic preparative HPLC to give Compound IN-14.1 (6.90 m g, 7%, $t_R$=4.276 min) and Compound IN-14.2 (21.40 m g, 21%, $t_R$=3.977 min) as white solids.

Before SFC Separation:
Isomer SFC $t_R$=1.869 and 2.034 min in 3 min chromatography (Column: AD-H; Method Name: AD-H_3UM_4_5_40_4ML_3MIN.M, ee=41.26%).
SFC separation condition:
Instrument: Thar 80
Column: AD (250 mm*30 mm, 10 um)
Mobile phase: A: Supercritical CO$_2$, B: MeOH (0.05% NH$_3$H$_2$O), A:B=45:45 at 80 mL/min
Column Temp: 38° C.
Nozzle Pressure: 100 Bar
Nozzle Temp: 60° C.
Evaporator Temp: 20° C.
Trimmer Temp: 25° C.
Wavelength: 220 nm Compound IN-14.1 (6.90 mg, 7%) as a white solid
LC-MS $t_R$=0.795 min in 5-95 AB_1.5 min chromatography (Welch MK RP-18e 25-2 mm), MS (ESI) m/z 566.1 [M+H]$^+$. $^1$H NMR (CDCl$_3$, 400 MHz): δ 9.06 (s, 1H), 8.20 (d, J=8.4 Hz, 1H), 8.07 (s, 1H), 7.74 (d, J=8.0 Hz, 1H), 7.70 (d, J=7.6 Hz, 2H), 7.32 (d, J=8.8 Hz, 1H), 6.32 (s, 1H), 5.49 (q, J=7.2 Hz, 2H), 4.25 (d, J=7.2 Hz, 1H), 4.16 (q, J=7.6 Hz, 2H), 3.96 (q, J=7.2 Hz, 1H), 3.72 (brs, 1H), 3.17 (q, J=7.6 Hz, 2H), 2.66 (d, J=6.8 Hz, 2H), 2.10-1.95 (m, 4H), 1.68-1.61 (m, 1H), 1.33 (t, J=7.2 Hz, 3H), 1.32-1.29 (m, 3H), 1.29 (t, J=7.2 Hz, 3H), 1.09-0.99 (m, 2H). Isomer SFC $t_R$=4.276 min in 10 min chromatography (Column: AS-H; Method Name: AS-H_S_3_5_40_3ML_8MIN_15CM.M, ee=98.37%).

Basic Preparative HPLC Method
Mobile phase A: water with 0.05% NH$_3$—H$_2$O solution
Mobile phase B: CH$_3$CN
Flow rate: 25 mL/min.
Detection: UV 220 nm/254 nm
Column: Gemini 150*25 5 u
Column temperature: 40° C.

| Time in min | % A | % B |
| --- | --- | --- |
| 0.00 | 50 | 50 |
| 10.00 | 20 | 80 |
| 10.20 | 0 | 100 |
| 14.00 | 0 | 100 |

Compound IN-14.2 (21.40 mg, 21%) as a white solid

LC-MS $t_R$=0.785 min in 5-95 AB_1.5 min chromatography (Welch MK RP-18e 25-2 mm), MS (ESI) m/z 566.0 [M+H]$^+$ $^1$H NMR (CDCl$_3$ 400 MHz): δ 9.06 (s, 1H), 8.19 (d, J=7.2 Hz, 1H), 8.08 (s, 1H), 7.73 (d, J=8.4 Hz, 2H), 7.68 (d, J=7.2 Hz, 1H), 7.32 (d, J=8.4 Hz, 1H), 6.34 (s, 1H), 5.49 (q, J=5.6 Hz, 1H), 4.23 (d, J=7.2 Hz, 1H), 4.16 (q, J=7.6 Hz, 2H), 3.96 (q, J=7.2 Hz, 1H), 3.77 (q, J=7.2 Hz, 1H), 3.17 (q, J=7.6 Hz, 2H), 2.78 (d, J=7.6 Hz, 2H), 2.14-1.95 (m, 2H), 1.74-1.64 (m, 8H), 1.37 (t, J=7.2 Hz, 3H), 1.32 (t, J=7.2 Hz, 3H). Isomer SFC $t_R$=3.977 min in 10 min chromatography (Column: AS-H; Method Name: AS-H_S_3_5_40_3ML_8MIN_15CM.M, ee=100.00%)

Basic Preparative HPLC Method

Mobile phase A: water with 0.05% NH$_3$—H$_2$O solution

Mobile phase B: CH$_3$CN

Flow rate: 25 mL/min.

Detection: UV 220 nm/254 nm

Column: Phenomenex Gemini 150*25 mm*10 um

Column temperature: 40° C.

| Time in min | % A | % B |
|---|---|---|
| 0.00 | 50 | 50 |
| 10.00 | 20 | 80 |
| 10.20 | 0 | 100 |
| 14.00 | 0 | 100 |

The following compounds are prepared by substituting the appropriate amines in Step 7.

Compounds IN-15.1 and IN-15.2

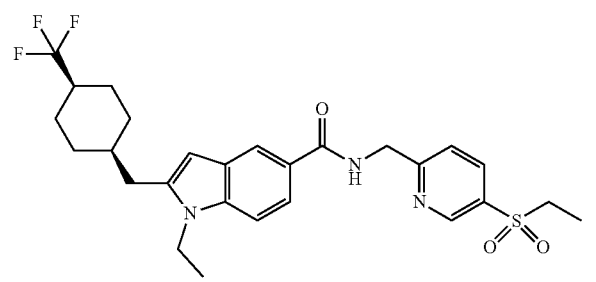

*isomers separated by chromatography, cis/trans configuration not assigned

Compounds IN-16.1 and IN-16.2

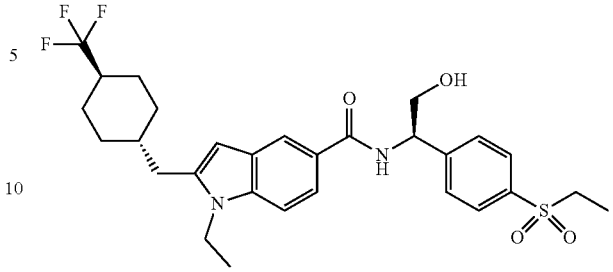

*isomers separated by chromatography, cis/trans configuration not assigned

Compounds IN-17.1 and IN-17.2

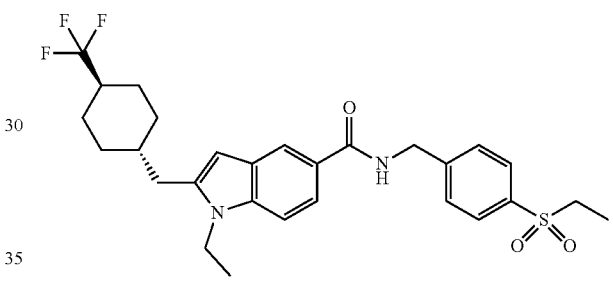

*isomers separated by chromatography, cis/trans configuration not assigned

Example 10

1-cyclopropyl-N-(4-(ethylsulfonyl)benzyl)-2-(4-(trifluoromethyl)benzyl)-1H-indole-5-carboxamide (Compound IN-18)

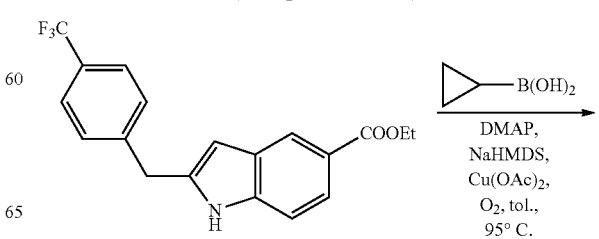

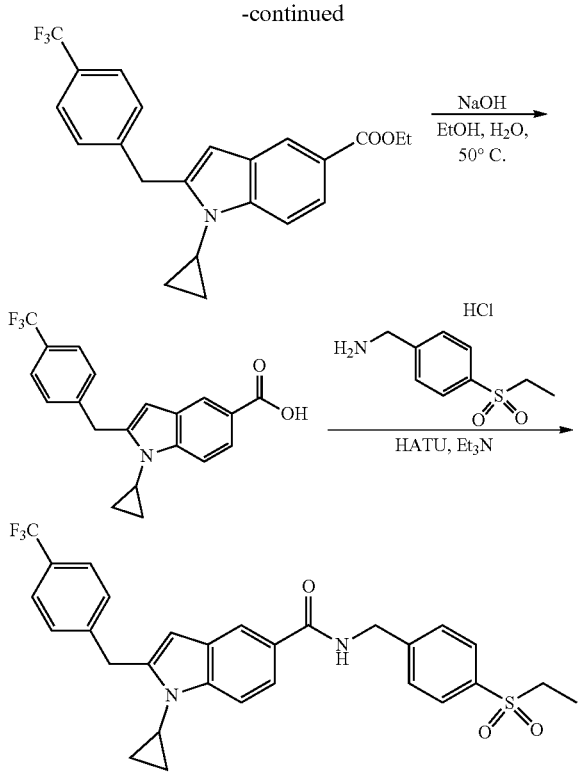

Step 1

To a mixture of ethyl 2-(4-(trifluoromethyl)benzyl)-1H-indole-5-carboxylate from Example 1 Step 6 (50 mg, 0.14 mmol), cyclopropylboronic acid (24 mg, 0.28 mmol), DMAP (50 mg, 0.42 mmol) and Cu(OAc)$_2$ (25 mg, 0.14 mmol) in dry toluene (2 mL) was added NaHMDS (0.42 mL, 0.42 mmol, 1N in THF) under N$_2$. Then the mixture was stirred at 95° C. for 2 h under O$_2$ (15 psi). TLC (petroleum ether/ethyl acetate=5/1) showed the reaction was completed. The mixture was filtered and washed with ethyl acetate (15 mL). The filtrate was concentrated under reduced pressure. The residue was purified by pre-TLC (petroleum ether/ethyl acetate=5/1) to afford ethyl 1-cyclopropyl-2-(4-(trifluoromethyl)benzyl)-1H-indole-5-carboxylate (18 mg, 33%) as a colorless oil. LC-MS Method 2 $t_R$=0.963 min in 5-95AB_1.5 min chromatography (Merck RP-18e 25-2 mm), MS (ESI) m/z 388.0 [M+H]$^+$.

Step 2

To a solution of ethyl 1-cyclopropyl-2-(4-(trifluoromethyl)benzyl)-1H-indole-5-carboxylate (20 mg, 0.05 mmol) in EtOH (3 mL) was added aq. NaOH solution (1 mL, 1.0 mmol, 1N). The reaction mixture was stirred at 26° C. for 20 h. TLC (petroleum ether/ethyl acetate=5/1) showed the reaction was not completed. Then the mixture was stirred at 50° C. for another 20 h. LCMS showed the reaction was completed. The solvent was removed and water (10 mL) was added. The mixture was acidified with 1 N HCl solution to pH=5 and extracted with ethyl acetate (3×10 mL). The combined organic layers were dried over anhydrous Na$_2$SO$_4$, filtered and concentrated to afford crude 1-cyclopropyl-2-(4-(trifluoromethyl)benzyl)-1H-indole-5-carboxylic acid (17 mg, 94%) as a white solid, which was used for the next step without further purification. LC-MS Method 2 $t_R$=0.821 min in 5-95AB_1.5 min chromatography (Merck RP-18e 25-2 mm), MS (ESI) m/z 360.0 [M+H]$^+$.

Step 3

To a mixture of 1-cyclopropyl-2-(4-(trifluoromethyl)benzyl)-1H-indole-5-carboxylic acid (17 mg, 0.047 mmol), (4-(ethylsulfonyl)phenyl)methanamine (17 mg, 0.07 mmol) and HATU (36 mg, 0.094 mmol) in dry CH$_2$Cl$_2$ (2 mL) was added Et$_3$N (14 mg, 0.14 mmol). Then the mixture was stirred at 26° C. for 2 h. LCMS showed the starting material was consumed completely. Water (5 mL) was added. The mixture was extracted with CH$_2$Cl$_2$ (3×10 mL). The combined organic layers were washed with brine, dried over anhydrous sodium sulfate, filtered and concentrated under reduced pressure. The residue was purified by neutral preparative HPLC separation, then basic preparative HPLC separation and then lyophilized directly to afford 1-cyclopropyl-N-(4-(ethylsulfonyl)benzyl)-2-(4-(trifluoromethyl)benzyl)-1H-indole-5-carboxamide (Compound IN-18, 10.5 mg, 42%) as a white solid.

LC-MS Method 2 $t_R$=0.829 min in 5-95AB_1.5 min chromatography (MK RP-18e 25-2 mm), MS (ESI) m/z 541.0 [M+H]$^+$. $^1$H NMR (CDCl$_3$ 400 MHz): δ 8.02 (s, 1H), 7.88 (d, J=8.4 Hz, 2H), 7.67 (d, J=8.4 Hz, 1H), 7.57 (d, J=8.0 Hz, 5H), 7.34 (d, J=8.0 Hz, 2H), 6.61 (t, J=6.4 Hz, 1H), 6.28 (s, 1H), 4.79 (d, J=6.4 Hz, 2H), 4.31 (s, 2H), 3.11 (q, J=7.2 Hz, 2H), 3.00-2.90 (m, 1H), 1.28 (t, J=7.2 Hz, 3H), 1.15-1.12 (m, 2H), 1.07-1.02 (m, 2H).

Neutral Preparative HPLC Method

Mobile phase A: water with 10 mM NH$_4$HCO$_3$

Mobile phase B: CH$_3$CN

Flow rate: 22 mL/min.

Detection: UV 220 nm/254 nm

Column: Phenomenex Synergi C18 150*25*10 um

Column temperature: 30° C.

| Time in min | % A | % B |
|---|---|---|
| 0.00 | 62 | 42 |
| 10.00 | 32 | 72 |
| 10.20 | 0 | 100 |
| 13.00 | 0 | 100 |

Basic Preparative HPLC Method

Mobile phase A: water with 0.05% ammonia hydroxide

Mobile phase B: CH$_3$CN

Flow rate: 25 mL/min.

Detection: UV 220 nm/254 nm

Column: DuraShell 150*25 mm*5 um

Column temperature: 30° C.

| Time in min | % A | % B |
|---|---|---|
| 0.00 | 47 | 53 |
| 10.00 | 17 | 83 |
| 10.20 | 0 | 100 |
| 13.00 | 0 | 100 |

The compound below is prepared by a similar procedure using (R)-2-amino-2-(5-(ethylsulfonyl)pyridin-2-yl)ethan-1-ol in Step 3.

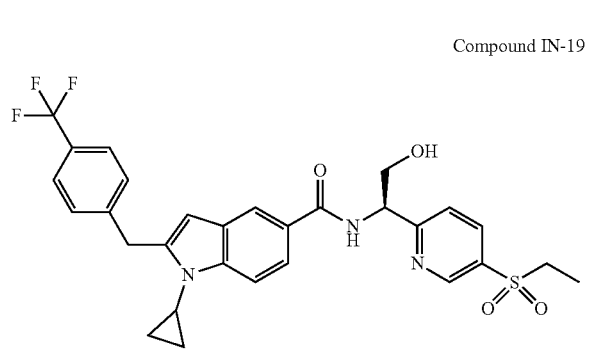 [SMILES: CCS(=O)(=O)c1ccc([C@H](CO)NC(=O)c2ccc3c(c2)cc(Cc2ccc(C(F)(F)F)cc2)n3C2CC2)nc1]

Compound IN-19

Example 11

(R)-2-(4-carbamoylbenzyl)-1-ethyl-N-(1-(5-(ethylsulfonyl)pyridin-2-yl)-2-hydroxyethyl)-1H-indole-5-carboxamide (Compound IN-20))

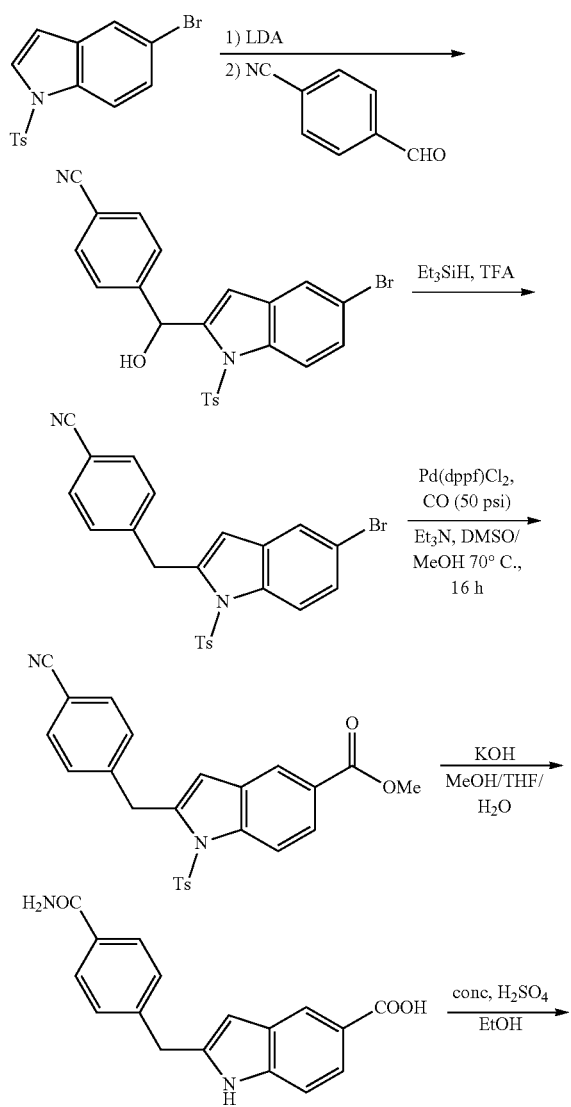

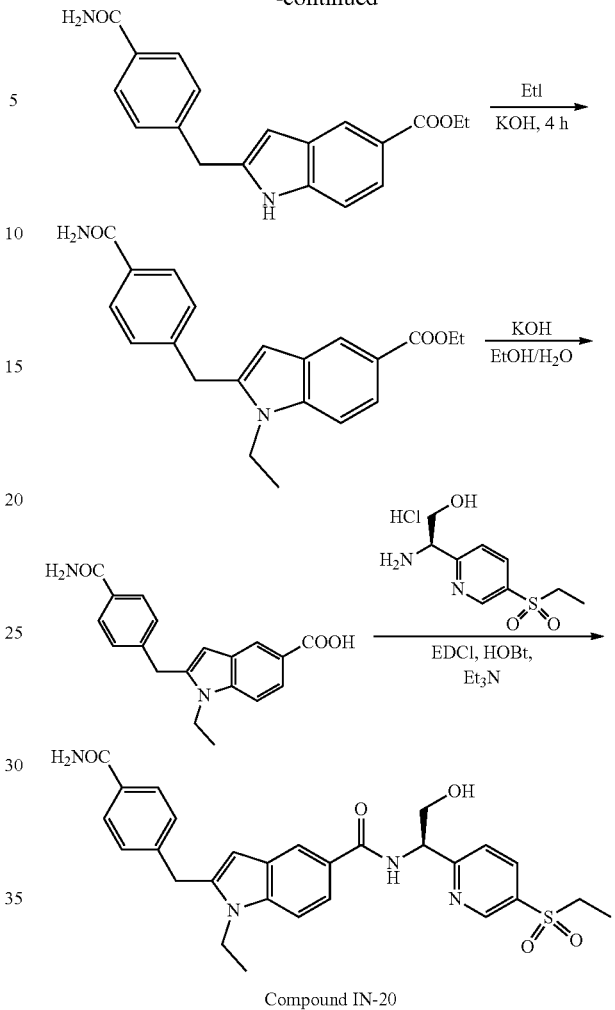

Compound IN-20

Step 1

To a solution of 5-bromo-1-tosyl-1H-indole (1 g, 2.866 mmol) in anhydrous toluene (10 mL) was added dropwise LDA (1.92 mL, 3.84 mmol, 2 M in THF/heptane/ethylbenzene) at −78° C. under $N_2$. The mixture was stirred at −78° C. for 30 min. A solution of 4-formylbenzonitrile (1.126 g, 8.598 mmol) in anhydrous THF (5 mL) was added dropwise to the mixture at −78° C. under $N_2$. The reaction mixture was stirred at −78° C.-15° C. for 16 h under $N_2$. TLC (petroleum ether/ethyl acetate=5/1) showed that most of 5-bromo-1-tosyl-1H-indole was consumed. The mixture was quenched with sat. $NH_4Cl$ solution (50 mL) and extracted with ethyl acetate (3×50 mL). The combined organic layers were dried over anhydrous $Na_2SO_4$, filtered and concentrated under reduced pressure. The residue was purified by re-crystallization from petroleum ether/ethyl acetate (2/1, 50 mL) to afford 4-((5-bromo-1-tosyl-1H-indol-2-yl)(hydroxy)methyl)benzonitrile (1.20 g, 87%) as a white solid. LC-MS Method 2 $t_R$=0.873 min in 5-95AB 1.5 min chromatography (Welch Merck RP-18e 25-2 mm), MS (ESI) m/z 462.9 [M-$NH_3$+H]$^+$.

Step 2

To a solution of 4-((5-bromo-1-tosyl-1H-indol-2-yl)(hydroxy)methyl)benzonitrile (1.2 g, 2.5 mmol) in $CH_2Cl_2$ (50 mL) was added $Et_3SiH$ (6 mL) and TFA (6 mL). The mixture was stirred at room temperature for 4 h. LCMS showed that the reaction was completed. The mixture was quenched with water (80 mL) and extracted with $CH_2Cl_2$ (3×80 mL). The combined organic layers were dried over anhydrous $Na_2SO_4$, filtered and concentrated under reduced pressure. The residue was purified by column chromatography on silica gel eluting with petroleum ether/ethyl acetate=1/0-4/1 to afford 4-((5-bromo-1-tosyl-1H-indol-2-yl)methyl)benzonitrile (1.06 g, 91%) as a white solid. LC-MS Method 2 $t_R$=0.945 min in 5-95AB_1.5 min chromatography (Welch Merck RP-18e 25-2 mm), MS (ESI) m/z 464.9 $[M+H]^+$.

Step 3

To a solution of 4-((5-bromo-1-tosyl-1H-indol-2-yl)methyl)benzonitrile (1.4 g, 3 mmol) in MeOH (50 mL) and DMSO (10 mL) was added $Pd(dppf)Cl_2$ (661 mg, 0.905 mmol) and $Et_3N$ (606 mg, 6 mmol). The mixture was stirred at 70° C. for 16 h under CO (50 psi). TLC (petroleum ether/ethyl acetate=2/1) showed that most of 4-((5-bromo-1-tosyl-1H-indol-2-yl)methyl)benzonitrile was consumed. The mixture was concentrated under reduced pressure. The residue was diluted with ethyl acetate (200 mL) and filtered. The filtrate was washed with brine (3×200 mL), dried over anhydrous $Na_2SO_4$, filtered and concentrated under reduced pressure. The residue was purified by column chromatography on silica gel eluting with petroleum ether/ethyl acetate=I/O-2/1 to afford methyl 2-(4-cyanobenzyl)-1-tosyl-1H-indole-5-carboxylate (1.03 g, 77%) as a yellow solid. LC-MS Method 2 $t_R$=0.889 min in 5-95AB_1.5 min chromatography (Welch Merck RP-18e 25-2 mm), MS (ESI) m/z 444.9 $[M+H]^+$.

Step 4

To a solution of methyl 2-(4-cyanobenzyl)-1-tosyl-1H-indole-5-carboxylate (1.03 g, 2.32 mmol) in MeOH (50 mL) and THF (10 mL) was added KOH (2.6 g, 4.64 mmol) and water (10 mL). The reaction mixture was stirred at 70° C. for 48 h under $N_2$. LCMS showed the reaction was completed. The mixture was concentrated under reduced pressure The residue was adjusted to pH=5-6 with 1 N HCl solution. A lot of solids was precipitate out and filtered. The filter cake was washed with petroleum ether/ethyl acetate (3/1, 30 mL) and dried under reduced pressure to afford crude 2-(4-carbamoylbenzyl)-1H-indole-5-carboxylic acid (0.8 g, >100%, contained some salt) as a yellow solid, which was used for the next step directly without further purification. LC-MS Method 2 $t_R$=0.595 min in 5-95AB_1.5 min chromatography (Welch Merck RP-18e 25-2 mm), MS (ESI) m/z 294.9 $[M+H]^+$.

Step 5

To a solution of 2-(4-carbamoylbenzyl)-1H-indole-5-carboxylic acid (400 mg, 1.36 mmol) in EtOH (10 mL) was added conc. $H_2SO_4$ (1.5 mL). Then the mixture was stirred at 80° C. for 3 h. LCMS showed that the starting material was consumed completely. The mixture was basified with aq. $NaHCO_3$ solution to pH=8. The aqueous layer was extracted with ethyl acetate (3×20 mL). The combined organic layers were dried over anhydrous $Na_2SO_4$, filtered and concentrated under reduced pressure. The residue was purified by column chromatography on silica gel eluting with petroleum ether/ethyl acetate=5/1-0/1 to afford ethyl 2-(4-carbamoylbenzyl)-1H-indole-5-carboxylate (110 mg, 25%) as a yellow solid. LC-MS Method 2 $t_R$=0.724 min in 5-95AB_1.5 min chromatography (Welch Merck RP-18e 25-2 mm), MS (ESI) m/z 323.1 $[M+H]^+$.

Step 6

To a solution of ethyl 2-(4-carbamoylbenzyl)-1H-indole-5-carboxylate (110 mg, 0.342 mmol) in anhydrous THF (5 mL) was added KOH (58 mg, 1.026 mmol) and EtI (107 mg, 0.684 mmol). Then the mixture was stirred at 40° C. for 4 h. LCMS showed the reaction was completed. The mixture was adjusted to pH=5-6 with 1 N HCl solution and diluted with water (10 mL). The aqueous layer was extracted with ethyl acetate (3×15 mL). The combined organic layers were dried over anhydrous $Na_2SO_4$, filtered and concentrated under reduced pressure. The residue was purified by column chromatography on silica gel eluting with petroleum ether/ethyl acetate=5/1-0/1 to afford ethyl 2-(4-carbamoylbenzyl)-1-ethyl-1H-indole-5-carboxylate (95 mg, 79%) as a yellow solid. LC-MS Method 2 $t_R$=0.783 min in 5-95AB_1.5 min chromatography (Welch Merck RP-18e 25-2 mm), MS (ESI) m/z 350.9 $[M+H]^+$.

Step 7

To a solution of ethyl 2-(4-carbamoylbenzyl)-1-ethyl-1H-indole-5-carboxylate (95 mg, 0.271 mmol) in EtOH (5 mL) and $H_2O$ (1 mL) was added KOH (304 mrg, 5.43 mmol). The mixture was stirred at 40° C. for 6 h under $N_2$. LCMS showed that the reaction was completed. The mixture was concentrated under reduced pressure. The residue was diluted with water (10 mL) and adjusted to pH=5-6 with 1 N HCl solution. The aqueous layer was extracted with ethyl acetate (3×20 mL). The combined organic layers were dried over anhydrous $Na_2SO_4$, filtered and concentrated to afford crude 2-(4-carbamoylbenzyl)-1-ethyl-1H-indole-5-carboxylic acid (240 mg, >100%, contained some salt) as a yellow solid, which was used for next step directly without further purification. LC-MS Method 2 $t_R$=0.674 min in 5-95AB_1.5 min chromatography (Welch Merck RP-18e 25-2 mm), MS (ESI) m/z 322.9 $[M+H]^+$.

Step 8

To a solution of crude 2-(4-carbamoylbenzyl)-1-ethyl-1H-indole-5-carboxylic acid (87 mg, 0.271 mmol) in $CH_2Cl_2$(5 mL) was added (R)-2-amino-2-(5-(ethylsulfonyl)pyridin-2-yl)ethanol HCl salt (108 mg, 0.4065 mmol), EDCI (104 mg, 0.542 mmol), HOBt (73 mg, 0.542 mmol) and $Et_3N$ (55 mg, 0.542 mmol). The mixture was stirred at room temperature for 16 h under $N_2$. LCMS showed that the reaction was completed. The mixture was quenched with water (15 mL) and extracted with $CH_2Cl_2$ (3×15 mL). The combined organic layers were dried over anhydrous sodium sulfate, filtered and concentrated under reduced pressure. The residue was purified by preparative TLC with $CH_2Cl_2$/MeOH=10/1 to afford crude (R)-2-(4-carbamoylbenzyl)-1-ethyl-N-(1-(5-(ethylsulfonyl)pyridin-2-yl)-2-hydroxyethyl)-1H-indole-5-carboxamide (40 mg, 27%) as a yellow solid. The crude product (14 mg, 0.026 mmol) was purified by basic preparative HPLC separation and dry-freezing directly to give (R)-2-(4-carbamoylbenzyl)-1-ethyl-N-(1-(5-(ethylsulfonyl)pyridin-2-yl)-2-hydroxyethyl)-1H-indole-5-carboxamide (Compound IN-20, 4.0 mg, 29%) as a white solid. LC-MS Method 2 $t_R$=0.675 min in 5-95AB_1.5 min chromatography (Welch Merck RP-18e 25-2 mm), MS (ESI) m/z 535.1 $[M+H]^+$. $^1$H NMR ($CDCl_3$ 400 MHz): δ 9.05 (d, J=2.4 Hz, 1H), 8.20 (dd, J=8.4 Hz, 2.0 Hz, 1H), 8.10 (s, 1H), 7.80-7.67 (m, 5H), 7.35-7.28 (m, 3H), 6.35 (s, 1H), 6.15-5.95 (brs, 1H), 5.65-5.53 (brs, 1H), 5.49 (q, J=4.0 Hz, 1H), 4.24 (dd, J=4.0, 11.2 Hz, 1H), 4.20 (s, 2H), 4.11-4.00 (m, 3H), 3.17 (q, J=7.2 Hz, 2H), 1.34 (t, J=7.2 Hz, 3H), 1.19 (t, J=7.2 Hz, 3H). Isomer SFC $t_R$=2.504 min in 5 min chromatography (Column: AD-H; Method Name: AD-H_3UM_4_40_4ML_5MIN, ee=99%).

Basic Preparative HPLC Method

Mobile phase A: water with 0.05% $NH_4OH$
Mobile phase B: $CH_3CN$
Flow rate: 25 mL/min.
Detection: UV 220 nm/254 nm
Column: Phenomenex Gemini 150*25 mm*10 um Column temperature: 30° C.

| Time in min | % A | % B |
|---|---|---|
| 0.00 | 80 | 20 |
| 10.00 | 50 | 50 |
| 10.20 | 0 | 100 |
| 13.00 | 0 | 100 |

Example 12

(R)-2-(4-cyano benzyl)-1-ethyl-N-(1-(5-(ethylsulfonyl)pyridin-2-yl)-2-hydroxyethyl)-1H-indole-5-carboxamide (Compound IN-21)

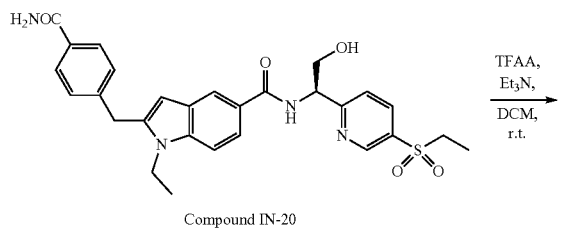

Compound IN-20

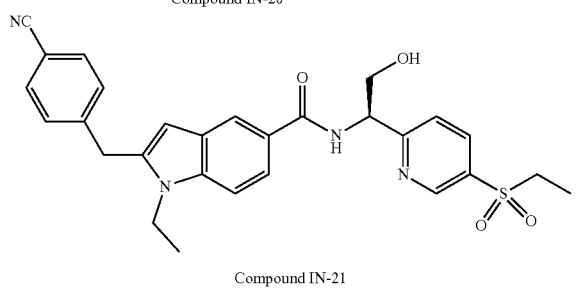

Compound IN-21

To a solution of (R)-2-(4-carbamoylbenzyl)-1-ethyl-N-(1-(5-(ethylsulfonyl)pyridin-2-yl)-2-hydroxyethyl)-1H-indole-5-carboxamide (40 mg, 0.0748 mmol) in CH$_2$Cl$_2$ (5 mL) was added TFAA (31 mg, 0.1495 mmol) and Et$_3$N (23 mg, 0.2244 mmol). The mixture was stirred at room temperature for 1.5 h. LCMS showed that the desired MS was observed. The mixture was quenched with water (10 mL) and extracted with CH$_2$Cl$_2$ (3×10 mL). The combined organic layers were dried over anhydrous sodium sulfate, filtered and concentrated under reduced pressure. The residue was purified by preparative TLC with CH$_2$Cl$_2$/acetone=2/1 to give crude product (15 mg, 39%) as a pale yellow solid. The crude product (10 mg) was further purified by basic preparative HPLC separation and dry-freezing directly to afford (R)-2-(4-cyanobenzyl)-1-ethyl-N-(1-(5-(ethylsulfonyl)pyridin-2-yl)-2-hydroxyethyl)-1H-indole-5-carboxamide (Compound IN-21, 2.00 mg) as a white solid. LC-MS Method 2 t$_R$=0.743 min in 5-95AB_1.5 min chromatography (Welch Merck RP-18e 25-2 mm), MS (ESI) m/z 517.0 [M+H]$^+$. $^1$H NMR (CDCl$_3$ 400 MHz): δ 8.98 (s, 1H), 8.13 (d, J=8.4 Hz, 1H), 8.03 (s, 1H), 7.71-7.60 (m, 3H), 7.55 (d, J=8.0 Hz, 2H), 7.30-7.18 (m, 3H), 6.27 (s, 1H), 5.46-5.39 (m, 1H), 4.24-4.15 (m, 1H), 4.13 (s, 2H), 4.05-3.93 (m, 3H), 3.63-3.53 (m, 1H), 3.09 (q, J=7.6 Hz, 2H), 1.27 (t, J=7.2 Hz, 3H), 1.12 (t, J=7.2 Hz, 3H). Isomer SFC t$_R$=1.063 min in 5 min chromatography (Column: AD-H; Method Name: AD-H_3UM_4_40_4ML_5MIN.M, ee=98%).

Basic Preparative HPLC Method

Mobile phase A: water with 0.05% NH$_4$OH
Mobile phase B: CH$_3$CN
Flow rate: 25 mL/min.
Detection: UV 220 nm/254 nm
Column: Phenomenex Gemini 150*25 mm*10 um
Column temperature: 30° C.

| Time in min | % A | % B |
|---|---|---|
| 0.00 | 65 | 35 |
| 10.00 | 35 | 65 |
| 10.20 | 0 | 100 |
| 13.00 | 0 | 100 |

Example 13

(R)-1-ethyl-N-(1-(4-(ethylsulfonyl)phenyl)-2-hydroxyethyl)-2-(5-(trifluoromethyl)picolinoyl)-1H-indole-5-carboxamide (Compound IN-22)

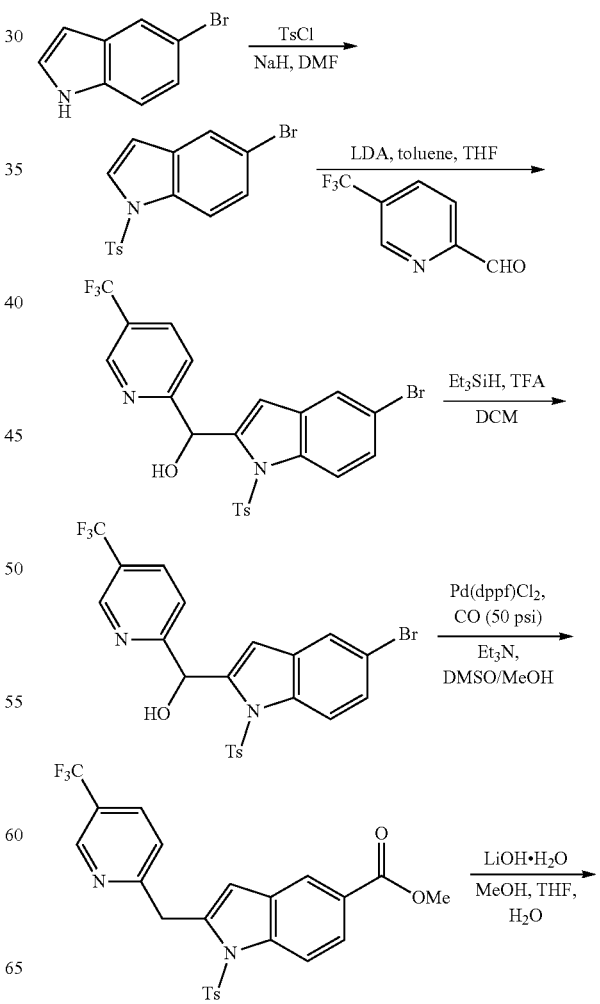

-continued

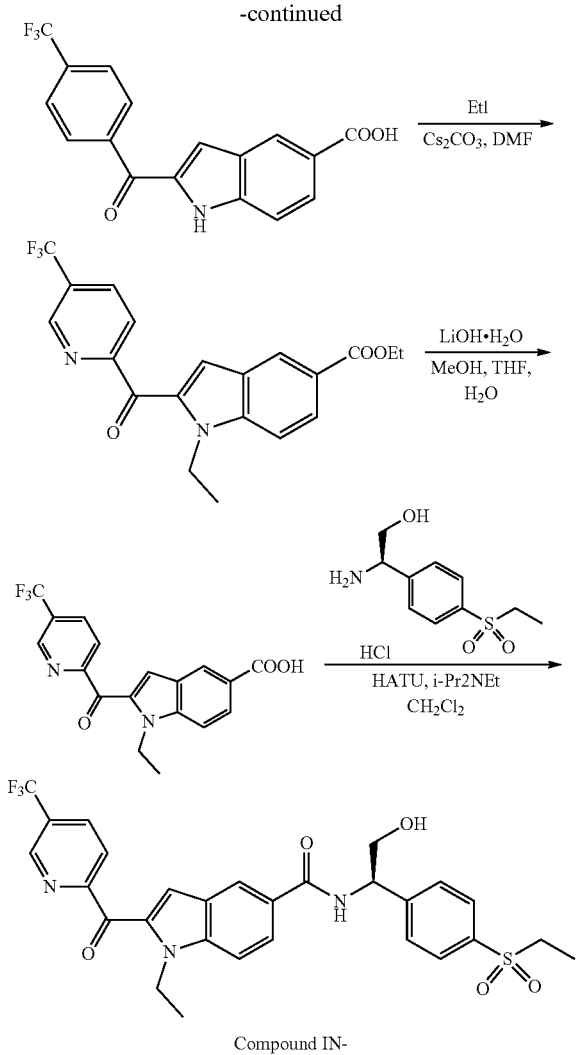

Compound IN-

Steps 1-4 are carried using procedures analogous to those in Example Steps 1-4.

Step 5

A stirred mixture of methyl 1-tosyl-2-((5-(trifluoromethyl)pyridin-2-yl)methyl)-1H-indole-5-carboxylate (135 mg, 0.28 mmol), LiOH·H₂O (116 mg, 2.8 mmol) and 2:1:1 MeOH/THF/H₂O (4 mL) was heated at 35° C. for 5 d open to the atmosphere. The mixture was diluted with EtOAc (90 mL), washed with 2.5% aq HCl (10 mL) and brine (10 mL), and dried over Na2SO₄. Removal of the solvent left 2-(4-(trifluoromethyl)benzoyl)-1H-indole-5-carboxylic acid (91 mg, 99%). LC-MS Method 1 $t_R$=1.43 min, m/z=335.

Step 6

To a stirred mixture of 2-(4-(trifluoromethyl)benzoyl)-1H-indole-5-carboxylic acid (91 mg, 0.27 mmol), Cs₂CO₃ (178 mg, 0.54 mmol) and dry DMF (1.5 mL) was added iodoethane (44 µL, 0.54 mmol). The mixture was stirred at rt for 4 h, diluted with EtOAc (90 mL), washed with 2.5% aq HCl (10 mL) and brine (10 mL), and dried over Na₂SO₄. Removal of the solvent left a yellow solid (117 mg). Chromatography on a 12 g silica cartridge, eluted with a 0-60% EtOAc in hexanes gradient, afforded ethyl 1-ethyl-2-(5-(trifluoromethyl)picolinoyl)-1H-indole-5-carboxylate (29 mg, 27%) as an oil which was used directly. LC-MS Method 1 $t_R$=1.94 min, m/z=391.

Step 7

Ethyl 1-ethyl-2-(5-(trifluoromethyl)picolinoyl)-1H-indole-5-carboxylate (29 mg, 74 µmol) is treated under conditions analogous to those in Step 5 to provide 1-ethyl-2-(5-(trifluoromethyl)picolinoyl)-1H-indole-5-carboxylic acid (20 mg, 74%) which was used directly in the next step. LC-MS Method 1 $t_R$=1.61 min, m/z=363.

Step 8

To a stirred solution of 1-ethyl-2-(5-(trifluoromethyl)picolinoyl)-1H-indole-5-carboxylic acid (20 mg, 55 µmol), (R)-2-amino-2-(4-(ethylsulfonyl)phenyl)ethan-1-ol hydrochloride (22 mg, 83 µmol), i-Pr₂NEt (52 µL, 0.29 mmol) and CH₂Cl₂ (1 mL) was added solid HATU (42 mg, 0.11 mmol). The mixture was stirred for 2 h and concentrated. The residue was purified by prep HPLC to afford (R)-1-ethyl-N-(1-(4-(ethylsulfonyl)phenyl)-2-hydroxyethyl)-2-(5-(trifluoromethyl)picolinoyl)-1H-indole-5-carboxamide (Compound IN-22, 23 mg, 72%) as a yellow solid. LC-MS Method 1 $t_R$=1.46 min, m/z=574. ¹H NMR (CD₃OD, 400 MHz) δ 1.20 (t, 3H), 1.43 (t, 3H), 3.18 (q, 2H), 3.92 (d, 2H), 4.73 (q, 2H), 5.31 (t, 1H), 7.63 (d, 1H), 7.66-7.74 (m, 3H), 7.87 (d, 2H), 7.93 (d, 1H), 8.31-8.39 (m, 2H), 9.04 (s, 1H).

Example 14

1-ethyl-N—((R)-1-(4-(ethylsulfonyl)phenyl)-2-hydroxyethyl)-2-(hydroxy(5-(trifluoromethyl)pyridin-2-yl)methyl)-1H-indole-5-carboxamide (Compound IN-23)

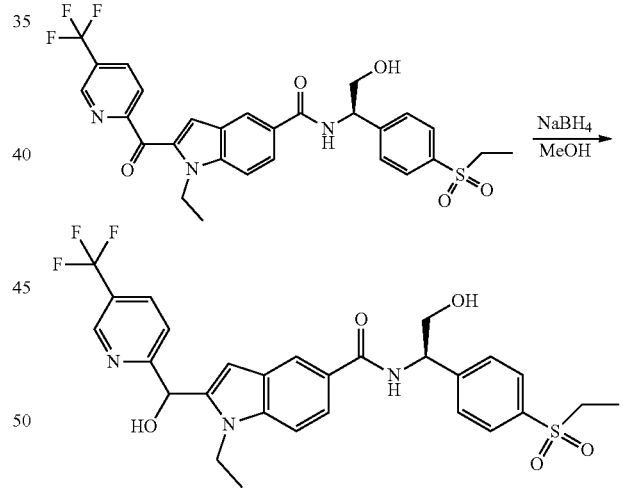

To a stirred solution of (R)-1-ethyl-N-(1-(4-(ethylsulfonyl)phenyl)-2-hydroxyethyl)-2-(5-(trifluoromethyl)picolinoyl)-1H-indole-5-carboxamide (19 mg, 33 µmol) in MeOH (1 mL) was added powdered NaBH4 (~5 mg). The mixture was stirred for 1 h, and diluted with water (0.5 mL) and 5% aq HCl (0.5 mL). The solution was stirred for 15 min and purified directly by prep HPLC to afford the title compound (12 mg, 63%) as a solid. LC-MS Method 1 $t_R$=1.26 min, m/z=576. ¹H NMR (CD₃OD, 400 MHz) δ 1.20 (t, 3H), 1.28 (t, 3H), 2.17 (q, 2H), 3.91 (d, 2H), 4.38 (m, 2H), 5.17 (t, 1H), 6.16 (s, 1H), 6.19 (s, 1H), 7.45 (s, 2H), 7.65-7.78 (m, 3H), 7.89 (d, 2H), 7.97 (d, 1H), 8.09 (s, 1H), 8.13 (d, 1H), 8.84 (s, 1H).

LC-MS Data

| Cpd No | Cpd Name | LC-MS Method | $t_R$ (min) | Mass observed |
|---|---|---|---|---|
| IN-1 | 1-ethyl-N-(4-(ethylsulfonyl)benzyl)-2-(4-(trifluoromethyl)benzyl)-1H-indole-5-carboxamide | 2 | 0.82 | 529 |
| IN-2 | 1-ethyl-N-((5-(ethylsulfonyl)pyridin-2-yl)methyl)-2-(4-(trifluoromethyl)benzyl-1H-indole-5-carboxamide | 2 | 0.788 | 530.1 |
| IN-3 | (R)-1-ethyl-N-(1-(4-(ethylsulfonyl)phenyl)-2-hydroxyethyl)-2-(4-(trifluoromethyl)benzyl)-1H-indole-5-carboxamide | 2 | 0.787 | 559.0 |
| IN-4.1 and IN-4.2 | (R)-1-ethyl-N-(1-(5-(ethylsulfonyl)pyridin-2-yl)-2-hydroxyethyl)-2-(4-(trifluoromethyl)benzyl)-1H-indole-5-carboxamide | 2 | 0.926 | 560.1 |
| | (S)-1-ethyl-N-(1-(5-(ethylsulfonyl)pyridin-2-yl)-2-hydroxyethyl)-2-(4-(trifluoromethyl)benzyl)-1H-indole-5-carboxamide | 2 | 0.774 | 560.1 |
| IN-5 | (R)-2-((2,2-difluorobenzo[d][1,3]dioxol-5-yl)methyl)-1-ethyl-N-(1-(5-(ethylsulfonyl)pyridin-2-yl)-2-hydroxyethyl)-1H-indole-5-carboxamide | 2 | 0.891 | 572.1 |
| IN-6 | (R)-2-(4-(difluoromethoxy)benzyl)-1-ethyl-N-(1-(5-(ethylsulfonyl)pyridin-2-yl)-2-hydroxyethyl)-1H-indole-5-carboxamide | 2 | 0.746 | 558.1 |
| IN-7 | (R)-2-(3-(difluoromethoxy)benzyl)-1-ethyl-N-(1-(5-(ethylsulfonyl)pyridin-2-yl)-2-hydroxyethyl)-1H-indole-5-carboxamide | 4 | 1.130 | 558.0 |
| IN-8 | (R)-2-(4-chlorobenzyl)-1-ethyl-N-(1-(5-(ethylsulfonyl)pyridin-2-yl)-2-hydroxyethyl)-1H-indole-5-carboxamide | 2 | 0.851 | 526.1 |
| IN-9 | (R)-1-ethyl-N-(1-(4-(ethylsulfonyl)phenyl)-2-hydroxyethyl)-2-((5-(trifluoromethyl)pyridin-2-yl)methyl)-1H-indole-5-carboxamide | 1 | 1.42 | 560 |
| IN-10 | (R)-1-ethyl-N-(1-(4-(ethylsulfonyl)phenyl)-2-hydroxyethyl)-2-((4-(trifluoromethyl)piperidin-1-yl)methyl)-1H-indole-5-carboxamide | 1 | 0.82 | 566 |
| IN-11 | (R)-1-ethyl-N-(1-(5-(ethylsulfonyl)pyridin-2-yl)-2-hydroxyethyl)-2-((4-(trifluoromethyl)piperidin-1-yl)methyl)-1H-indole-5-carboxamide | 1 | 0.79 | 567 |
| IN-12 | 1-cyclopropyl-N-(4-(ethylsulfonyl)benzyl)-2-((4-(trifluoromethyl)piperidin-1-yl)methyl)-1H-indole-5-carboxamide | 1 | 0.91 | 548 |
| IN-13 | (R)-1-cyclopropyl-N-(1-(4-(ethylsulfonyl)phenyl)-2-hydroxyethyl)-2-((4-(trifluoromethyl)piperidin-1-yl)methyl)-1H-indole-5-carboxamide | 1 | 0.84 | 578 |
| IN-14.1 and IN-14.2 | 1-ethyl-N-((R)-1-(5-(ethylsulfonyl)pyridin-2-yl)-2-hydroxyethyl)-2-(((1r,4R)-4-(trifluoromethyl)cyclohexyl)methyl)-1H-indole-5-carboxamide | 2 | 0.785 | 566.0 |
| | 1-ethyl-N-((R)-1-(5-(ethylsulfonyl)pyridin-2-yl)-2-hydroxyethyl)-2-(((1s,4S)-4-(trifluoromethyl)cyclohexyl)methyl)-1H-indole-5-carboxamide | 2 | 0.795 | 566.1 |
| IN-15.1 and IN-15.2 | 1-ethyl-N-((5-(ethylsulfonyl)pyridin-2-yl)methyl)-2-(((1r,4r)-4-(trifluoromethyl)cyclohexyl)methyl)-1H-indole-5-carboxamide | 2 | 0.808 | 536.1 |
| | 1-ethyl-N-((5-(ethylsulfonyl)pyridin-2-yl)methyl)-2-(((1s,4s)-4-(trifluoromethyl)cyclohexyl)methyl)-1H-indole-5-carboxamide | 2 | 0.800 | 536.1 |
| IN-16.1 and IN-16.2 | 1-ethyl-N-((R)-1-(4-(ethylsulfonyl)phenyl)-2-hydroxyethyl)-2-(((1r,4R)-4-(trifluoromethyl)cyclohexyl)methyl)-1H-indole-5-carboxamide | 2 | 0.801 | 565.0 |
| | 1-ethyl-N-((R)-1-(4-(ethylsulfonyl)phenyl)-2-hydroxyethyl)-2-(((1s,4S)-4-(trifluoromethyl)cyclohexyl)methyl)-1H-indole-5-carboxamide | 2 | 0.798 | 565.1 |
| IN-17.1 and IN-17.2 | 1-ethyl-N-(4-(ethylsulfonyl)benzyl)-2-(((1r,4r)-4-(trifluoromethyl)cyclohexyl)methyl)-1H-indole-5-carboxamide | 2 | 0.838 | 535.0 |

| Cpd No | Cpd Name | LC-MS Method | $t_R$ (min) | Mass observed |
|---|---|---|---|---|
|  | 1-ethyl-N-(4-(ethylsulfonyl)benzyl)-2-(((1s,4s)-4-(trifluoromethyl)cyclohexyl)methyl)-1H-indole-5-carboxamide | 2 | 0.837 | 535.1 |
| IN-19 | (R)-1-cyclopropyl-N-(1-(5-(ethylsulfonyl)pyridin-2-yl)-2-hydroxyethyl)-2-(4-(trifluoromethyl)benzyl)-1H-indole-5-carboxamide | 2 | 0.783 | 572.2 |
| IN-20 | (R)-2-(4-carbamoylbenzyl)-1-ethyl-N-(1-(5-(ethylsulfonyl)pyridin-2-yl)-2-hydroxyethyl)-1H-indole-5-carboxamide | 2 | 0.675 | 535.1 |
| IN-21 | (R)-2-(4-cyanobenzyl)-1-ethyl-N-(1-(5-(ethylsulfonyl)pyridin-2-yl)-2-hydroxyethyl)-1H-indole-5-carboxamide | 2 | 0.743 | 517.0 |
| IN-22 | (R)-1-ethyl-N-(1-(4-(ethylsulfonyl)phenyl)-2-hydroxyethyl)-2-(5-(trifluoromethyl)picolinoyl)-1H-indole-5-carboxamide | 1 | 1.46 | 574 |
| IN-23 | 1-ethyl-N-((R)-1-(4-(ethylsulfonyl)phenyl)-2-hydroxyethyl)-2-(hydroxy(5-(trifluoromethyl)pyridin-2-yl)methyl)-1H-indole-5-carboxamide | 1 | 1.27 | 576 |
| AI-1 | 1-cyclopropyl-N-(4-(ethylsulfonyl)benzyl)-2-(((1r,4r)-4-(trifluoromethyl)cyclohexyl)methyl)-1H-pyrrolo[2,3-b]pyridine-5-carboxamide | 1 | 1.65 | 548 |
| AI-2 | 1-cyclopropyl-N-((R)-1-(4-(ethylsulfonyl)phenyl)-2-hydroxyethyl)-2-(((1r,4R)-4-(trifluoromethyl)cyclohexyl)methyl)-1H-pyrrolo[2,3-b]pyridine-5-carboxamide | 1 | 1.54 | 578 |
| AI-3 | N-(4-(ethylsulfonyl)benzyl)-1-(2-methylallyl)-2-(4-(trifluoromethyl)benzyl)-1H-pyrrolo[2,3-b]pyridine-5-carboxamide | 1 | 1.70 | 556 |
| BE-1 | 1-cyclopropyl-N-((R)-1-(4-(ethylsulfonyl)phenyl)-2-hydroxyethyl)-2-(((1r,4R)-4-(trifluoromethyl)cyclohexyl)oxy)-1H-benzo[d]imidazole-5-carboxamide | 1 | 1.46 | 580.51 (M + 1) |
| BE-2 | 1-ethyl-N-(4-(ethylsulfonyl)benzyl)-2-(((1r,4r)-4-(trifluoromethyl)cyclohexyl)oxy)-1H-benzo[d]imidazole-5-carboxamide | 1 | 1.51 | 538.47 (M + 1) |
| BE-3 | 1-cyclopropyl-N-(4-(ethylsulfonyl)benzyl)-2-(((1r,4r)-4-(trifluoromethyl)cyclohexyl)oxy)-1H-benzo[d]imidazole-5-carboxamide | 1 | 1.54 | 550.40 (M + 1) |
| BE-4.1 and BE-4.2 | N-(4-(ethylsulfonyl)benzyl)-1-isobutyl-2-(((1r,4r)-4-(trifluoromethyl)cyclohexyl)oxy)-1H-benzo[d]imidazole-5-carboxamide | 1 | 1.68 | 566.38 (M + 1) |
|  | N-(4-(ethylsulfonyl)benzyl)-1-isobutyl-2-(((1s,4s)-4-(trifluoromethyl)cyclohexyl)oxy)-1H-benzo[d]imidazole-5-carboxamide | 1 | 1.64 | 566.34 (M + 1) |
| BE-5 | 1-ethyl-N-(4-(ethylsulfonyl)benzyl)-2-(4-(trifluoromethyl)phenoxy)-1H-benzo[d]imidazole-5-carboxamide | 1 | 1.54 | 532.40 (M + 1) |
| BE-6 | 1-cyclopropyl-N-(4-(ethylsulfonyl)benzyl)-2-(4-(trifluoromethyl)phenoxy)-1H-benzo[d]imidazole-5-carboxamide | 1 | 1.57 | 544.46 (M + 1) |
| BE-7 | (R)-1-cyclopropyl-N-(1-(4-(ethylsulfonyl)phenyl)-2-hydroxyethyl)-2-(4-(trifluoromethyl)phenoxy)-1H-benzo[d]imidazole-5-carboxamide | 1 | 1.47 | 574.45 (M + 1) |
| BE-8 | (R)-1-ethyl-N-(1-(4-(ethylsulfonyl)phenyl)-2-hydroxyethyl)-2-(4-(trifluoromethyl)phenoxy)-1H-benzo[d]imidazole-5-carboxamide | 1 | 1.44 | 562.53 (M + 1) |
| BE-9 | (R)-1-ethyl-N-(1-(4-(ethylsulfonyl)phenyl)-2-hydroxyethyl)-2-(4-(trifluoromethoxy)phenoxy)-1H-benzo[d]imidazole-5-carboxamide | 1 | 1.49 | 578.47 (M + 1) |
| BE-10 | (R)—N-(2-(dimethylamino)-1-(4-(ethylsulfonyl)phenyl)ethyl)-1-ethyl-2-(4-(trifluoromethyl)phenoxy)-1H-benzo[d]imidazole-5-carboxamide | 2 | 0.82 | 589 |
| BE-11 | (R)—N-(2-amino-1-(4-(ethylsulfonyl)phenyl)ethyl)-1-ethyl-2-(4-(trifluoromethyl)phenoxy)-1H-benzo[d]imidazole-5-carboxamide | 2 | 0.80 | 561 |

-continued

| Cpd No | Cpd Name | LC-MS Method | $t_R$ (min) | Mass observed |
|---|---|---|---|---|
| BE-12 | (R)-2-((4,4-difluorocyclohexyl)methoxy)-1-ethyl-N-(1-(4-(ethylsulfonyl)phenyl)-2-hydroxyethyl)-1H-benzo[d]imidazole-5-carboxamide | 2 | 0.83 | 550 |
| BE-13 | (R)-2-((3,3-difluorocyclobutyl)methoxy)-1-ethyl-N-(1-(4-(ethylsulfonyl)phenyl)-2-hydroxyethyl)-1H-benzo[d]imidazole-5-carboxamide | 2 | 0.68 | 522, 544 |
| BE-14 | (R)-1-ethyl-N-(1-(4-(ethylsulfonyl)phenyl)-2-hydroxyethyl)-2-((4-(trifluoromethyl)benzyl)oxy)-1H-benzo[d]imidazole-5-carboxamide | 2 | 0.88 | 576 |
| BE-15 | (R)-1-cyclopropyl-N-(1-(4-(ethylsulfonyl)phenyl)-2-hydroxyethyl)-2-((4-(trifluoromethyl)benzyl)oxy)-1H-benzo[d]imidazole-5-carboxamide | 2 | 0.76 | 588 |
| BE-16 | (R)-1-cyclopropyl-2-((4,4-difluorocyclohexyl)methoxy)-N-(1-(4-(ethylsulfonyl)phenyl)-2-hydroxyethyl)-1H-benzo[d]imidazole-5-carboxamide | 2 | 0.71 | 562 |
| BE-17 | (R)-2-(cyclopropylmethoxy)-1-ethyl-N-(1-(4-(ethylsulfonyl)phenyl)-2-hydroxyethyl)-1H-benzo[d]imidazole-5-carboxamide | 3 | 1.70 | 472 |
| BE-18.1 and BE-18.2 | 1-cyclopropyl-N-(4-(ethylsulfonyl)benzyl)-2-(((1r,4r)-4-(trifluoromethyl)cyclohexyl)methyl)-1H-benzo[d]imidazole-5-carboxamide | 2 | 0.81 | 548 |
|  | 1-cyclopropyl-N-(4-(ethylsulfonyl)benzyl)-2-(((1s,4s)-4-(trifluoromethyl)cyclohexyl)methyl)-1H-benzo[d]imidazole-5-carboxamide | 2 | 0.80 | 548 |
| BE-19.1 and BE-19.2 | N-(4-(ethylsulfonyl)benzyl)-1-isobutyl-2-(((1r,4r)-4-(trifluoromethyl)cyclohexyl)methyl)-1H-benzo[d]imidazole-5-carboxamide | 2 | 0.72 | 564 |
|  | N-(4-(ethylsulfonyl)benzyl)-1-isobutyl-2-(((1s,4s)-4-(trifluoromethyl)cyclohexyl)methyl)-1H-benzo[d]imidazole-5-carboxamide | 2 | 0.72 | 564 |
| BE-20 | 1-ethyl-N-(4-(ethylsulfonyl)benzyl)-2-(((1r,4r)-4-(trifluoromethyl)cyclohexyl)methyl)-1H-benzo[d]imidazole-5-carboxamide | 2 | 0.79 | 536 |
| BE-21 | 1-cyclopropyl-N-((R)-1-(4-(ethylsulfonyl)phenyl)-2-hydroxyethyl)-2-(((1r,4R)-4-(trifluoromethyl)cyclohexyl)methyl)-1H-benzo[d]imidazole-5-carboxamide | 2 | 0.68 | 578 |
| BE-22 | 1-cyclopropyl-N-((S)-1-(4-(ethylsulfonyl)phenyl)-2-hydroxyethyl)-2-(((1r,4S)-4-(trifluoromethyl)cyclohexyl)methyl)-1H-benzo[d]imidazole-5-carboxamide | 2 | 0.67 | 578 |
| BE-23 | 1-ethyl-N-((R)-1-(4-(ethylsulfonyl)phenyl)-2-hydroxyethyl)-2-(((1r,4R)-4-(trifluoromethyl)cyclohexyl)methyl)-1H-benzo[d]imidazole-5-carboxamide | 2 | 0.66 | 566, 588 |
| BE-24 | 1-ethyl-N-((S)-1-(4-(ethylsulfonyl)phenyl)-2-hydroxyethyl)-2-(((1r,4S)-4-(trifluoromethyl)cyclohexyl)methyl)-1H-benzo[d]imidazole-5-carboxamide | 2 | 0.65 | 566, 588 |
| BE-25 | 1-cyclopropyl-N-((S)-1-(4-(ethylsulfonyl)phenyl)-3-hydroxypropyl)-2-(((1r,4S)-4-(trifluoromethyl)cyclohexyl)methyl)-1H-benzo[d]imidazole-5-carboxamide | 4 | 0.94 | 592 |
| BE-26.1 and BE-26.2 | N-((5-(ethylsulfonyl)pyridin-2-yl)methyl)-1-isobutyl-2-(((1r,4r)-4-(trifluoromethyl)cyclohexyl)methyl)-1H-benzo[d]imidazole-5-carboxamide | 2 | 0.69 | 565 |
|  | N-((5-(ethylsulfonyl)pyridin-2-yl)methyl)-1-isobutyl-2-(((1s,4s)-4-(trifluoromethyl)cyclohexyl)methyl)-1H-benzo[d]imidazole-5-carboxamide | 2 | 0.69 | 565 |
| BE-27.1 and | 1-cyclopropyl-N-((5-(ethylsulfonyl)pyridin-2-yl)methyl)-2-(((1r,4r)-4- | 2 | 0.65 | 549 |

| Cpd No | Cpd Name | LC-MS Method | $t_R$ (min) | Mass observed |
|---|---|---|---|---|
| BE-27.2 | (trifluoromethyl)cyclohexyl)methyl)-1H-benzo[d]imidazole-5-carboxamide 1-cyclopropyl-N-((5-(ethylsulfonyl)pyridin-2-yl)methyl)-2-(((1s,4s)-4-(trifluoromethyl)cyclohexyl)methyl)-1H-benzo[d]imidazole-5-carboxamide | 2 | 0.65 | 549 |
| BE-28 | 1-cyclopropyl-N-((R)-1-(5-(ethylsulfonyl)pyridin-2-yl)-2-hydroxyethyl)-2-(((1r,4R)-4-(trifluoromethyl)cyclohexyl)methyl)-1H-benzo[d]imidazole-5-carboxamide | 2 | 0.65 | 579 |
| BE-29 | 1-cyclopropyl-N-((S)-1-(5-(ethylsulfonyl)pyridin-2-yl)-2-hydroxyethyl)-2-(((1r,4S)-4-(trifluoromethyl)cyclohexyl)methyl)-1H-benzo[d]imidazole-5-carboxamide | 2 | 0.65 | 579 |
| BE-30 | 1-cyclopropyl-N-(4-(methylsulfonyl)benzyl)-2-(((1r,4r)-4-(trifluoromethyl)cyclohexyl)methyl)-1H-benzo[d]imidazole-5-carboxamide | 2 | 0.65 | 534 |
| BE-31 | 1-cyclopropyl-N-((5-(N-methylsulfamoyl)pyridin-2-yl)methyl)-2-(((1r,4r)-4-(trifluoromethyl)cyclohexyl)methyl)-1H-benzo[d]imidazole-5-carboxamide | 4 | 0.92 | 550 |
| BE-32 | 1-cyclopropyl-N-((R)-2-hydroxy-1-(4-(methylsulfonyl)phenyl)ethyl)-2-(((1r,4R)-4-(trifluoromethyl)cyclohexyl)methyl)-1H-benzo[d]imidazole-5-carboxamide | 2 | 0.66 | 564 |
| BE-33 | 1-cyclopropyl-N-(4-(N-methylsulfamoyl)benzyl)-2-(((1r,4r)-4-(trifluoromethyl)cyclohexyl)methyl)-1H-benzo[d]imidazole-5-carboxamide | 2 | 0.69 | 549 |
| BE-34 | N-(4-(ethylsulfonyl)benzyl)-1-methyl-2-(4-(trifluoromethyl)benzyl)-1H-benzo[d]imidazole-5-carboxamide | 2 | 0.67 | 516 |
| BE-35 | 1-ethyl-N-(4-(ethylsulfonyl)benzyl)-2-(4-(trifluoromethyl)benzyl)-1H-benzo[d]imidazole-5-carboxamide | 2 | 0.70 | 530 |
| BE-36 | 1-cyclopropyl-N-(4-(ethylsulfonyl)benzyl)-2-(4-(trifluoromethyl)benzyl)-1H-benzo[d]imidazole-5-carboxamide | 2 | 0.69 | 542 |
| BE-37 | N-(4-(ethylsulfonyl)benzyl)-1-(2,2,2-trifluoroethyl)-2-(4-(trifluoromethyl)benzyl)-1H-benzo[d]imidazole-5-carboxamide | 2 | 0.79 | 584 |
| BE-38 | 1-cyclobutyl-N-(4-(ethylsulfonyl)benzyl)-2-(4-(trifluoromethyl)benzyl)-1H-benzo[d]imidazole-5-carboxamide | 2 | 0.70 | 556 |
| BE-39 | N-(4-(ethylsulfonyl)benzyl)-1-neopentyl-2-(4-(trifluoromethyl)benzyl)-1H-benzo[d]imidazole-5-carboxamide | 2 | 0.75 | 572 |
| BE-40 | N-((5-(ethylsulfonyl)pyridin-2-yl)methyl)-1-isopropyl-2-(4-(trifluoromethyl)benzyl)-1H-benzo[d]imidazole-5-carboxamide | 2 | 0.76 | 545 |
| BE-41 | N-(4-(ethylsulfonyl)benzyl)-1-isobutyl-2-(4-(trifluoromethyl)benzyl)-1H-benzo[d]imidazole-5-carboxamide | 2 | 0.70 | 558 |
| BE-42 | 1-(tert-butyl)-N-((5-(ethylsulfonyl)pyridin-2-yl)methyl)-2-(4-(trifluoromethyl)benzyl)-1H-benzo[d]imidazole-5-carboxamide | 2 | 0.78 | 559 |
| BE-43 | N-((5-(ethylsulfonyl)pyridin-2-yl)methyl)-1-isobutyl-2-(4-(trifluoromethyl)benzyl)-1H-benzo[d]imidazole-5-carboxamide | 2 | 0.82 | 559 |
| BE-44 | rel-(R)—N-(1-(4-(ethylsulfonyl)phenyl)ethyl)-1-isobutyl-2-(4-(trifluoromethyl)benzyl)-1H-benzo[d]imidazole-5-carboxamide | 2 | 0.73 | 572 |
| BE-45 | rel-(R)—N-(1-(4-(ethylsulfonyl)phenyl)ethyl)-1-isobutyl-2-(4-(trifluoromethyl)benzyl)-1H-benzo[d]imidazole-5-carboxamide | 2 | 0.74 | 572 |
| BE-46.1 and BE-46.2 | 1-cyclopropyl-N-(4-(ethylsulfonyl)benzyl)-2-(((1r,4r)-4-methoxycyclohexyl)methyl)-1H-benzo[d]imidazole-5-carboxamide | 3 | 1.72 | 510 |
| | 1-cyclopropyl-N-(4-(ethylsulfonyl)benzyl)-2-(((1s,4s)-4-methoxycyclohexyl)methyl)-1H-benzo[d]imidazole-5-carboxamide | 2 | 0.60 | 510 |

-continued

| Cpd No | Cpd Name | LC-MS Method | $t_R$ (min) | Mass observed |
|---|---|---|---|---|
| BE-47 | (R)-1-cyclopropyl-N-(1-(4-(ethylsulfonyl)phenyl)-2-hydroxyethyl)-2-(4-(trifluoromethoxy)benzyl)-1H-benzo[d]imidazole-5-carboxamide | 1 | 1.24 | 588.49 (M + 1) |
| BE-48 | 1-cyclopropyl-2-(4-(difluoromethoxy)benzyl)-N-(4-(ethylsulfonyl)benzyl)-1H-benzo[d]imidazole-5-carboxamide | 2 | 0.70 | 540, 562 |
| BE-49 | tert-butyl 4-((1-cyclopropyl-5-((4-(ethylsulfonyl)benzyl)carbamoyl)-1H-benzo[d]imidazol-2-yl)methyl)piperidine-1-carboxylate | 1 | 1.09 | 581.59 (M + 1) |
| BE-50 | 1-cyclopropyl-N-(4-(ethylsulfonyl)benzyl)-2-((1-(2,2,2-trifluoroethyl)piperidin-4-yl)methyl)-1H-benzo[d]imidazole-5-carboxamide | 1 | 0.87 | 563.53 (M + 1) |
| BE-51 | 1-cyclopropyl-N-(4-(ethylsulfonyl)benzyl)-2-((6-(trifluoromethyl)pyridin-3-yl)methyl)-1H-benzo[d]imidazole-5-carboxamide | 1 | 1.18 | 543.47 (M + 1) |
| BE-52 | 2-((5-chloropyridin-2-yl)methyl)-1-cyclopropyl-N-(4-(ethylsulfonyl)benzyl)-1H-benzo[d]imidazole-5-carboxamide | 2 | 0.66 | 509, 511 |
| BE-53 | N-(4-(ethylsulfonyl)benzyl)-1-isobutyl-2-((4-(trifluoromethyl)piperidin-1-yl)methyl)-1H-benzo[d]imidazole-5-carboxamide | 1 | 1.04 | 565.38 (M + 1) |
| BE-54 | (R)-1-cyclopropyl-N-(1-(4-(ethylsulfonyl)phenyl)-2-hydroxyethyl)-2-((4-(trifluoromethyl)piperidin-1-yl)methyl)-1H-benzo[d]imidazole-5-carboxamide | 1 | 0.82 | 579.54 (M + 1) |
| BE-55.1 and BE-55.2 | 1-cyclopropyl-N-(4-(ethylsulfonyl)benzyl)-2-(1-(4-(trifluoromethyl)phenyl)ethyl)-1H-benzo[d]imidazole-5-carboxamide isomer 1 | 2 | 0.73 | 556 |
| | 1-cyclopropyl-N-(4-(ethylsulfonyl)benzyl)-2-(1-(4-(trifluoromethyl)phenyl)ethyl)-1H-benzo[d]imidazole-5-carboxamide isomer 2 | 2 | 0.73 | 556 |
| BE-56.1, BE-56.2, BE-56.3 and BE-56.4 | 1-ethyl-N-(4-(ethylsulfonyl)benzyl)-2-((6-(trifluoromethyl)tetrahydro-2H-pyran-3-yl)methyl)-1H-benzo[d]imidazole-5-carboxamide isomer 1 | 2 | 0.64 | 538, 560 |
| | 1-ethyl-N-(4-(ethylsulfonyl)benzyl)-2-((6-(trifluoromethyl)tetrahydro-2H-pyran-3-yl)methyl)-1H-benzo[d]imidazole-5-carboxamide isomer 2 | 2 | 0.64 | 538, 560 |
| | 1-ethyl-N-(4-(ethylsulfonyl)benzyl)-2-((6-(trifluoromethyl)tetrahydro-2H-pyran-3-yl)methyl)-1H-benzo[d]imidazole-5-carboxamide isomer 3 | 2 | 0.64 | 538, 560 |
| | 1-ethyl-N-(4-(ethylsulfonyl)benzyl)-2-((6-(trifluoromethyl)tetrahydro-2H-pyran-3-yl)methyl)-1H-benzo[d]imidazole-5-carboxamide isomer 4 | 2 | 0.75 | 538, 560 |
| BE-57.1, BE-57.2, BE-57.3 and BE-57.4 | 1-ethyl-N-((R)-1-(4-(ethylsulfonyl)phenyl)-2-hydroxyethyl)-2-((6-(trifluoromethyl)tetrahydro-2H-pyran-3-yl)methyl)-1H-benzo[d]imidazole-5-carboxamide isomer 1 | 2 | 0.73 | 568 |
| | 1-ethyl-N-((R)-1-(4-(ethylsulfonyl)phenyl)-2-hydroxyethyl)-2-((6-(trifluoromethyl)tetrahydro-2H-pyran-3-yl)methyl)-1H-benzo[d]imidazole-5-carboxamide isomer 2 | 2 | 0.73 | 568 |
| | 1-ethyl-N-((R)-1-(4-(ethylsulfonyl)phenyl)-2-hydroxyethyl)-2-((6-(trifluoromethyl)tetrahydro-2H-pyran-3-yl)methyl)-1H-benzo[d]imidazole-5-carboxamide isomer 3 | 2 | 0.64 | 568, 590 |
| | 1-ethyl-N-((R)-1-(4-(ethylsulfonyl)phenyl)-2-hydroxyethyl)-2-((6-(trifluoromethyl)tetrahydro-2H-pyran-3-yl)methyl)-1H-benzo[d]imidazole-5-carboxamide isomer 4 | 2 | 0.63 | 568, 590 |
| BE-58 | 7-bromo-N-(4-(ethylsulfonyl)benzyl)-1-methyl-2-(((1r,4r)-4-(trifluoromethyl)cyclohexyl)methyl)-1H-benzo[d]imidazole-5-carboxamide | 1 | 1.57 | 600, 602 |

-continued

| Cpd No | Cpd Name | LC-MS Method | $t_R$ (min) | Mass observed |
|---|---|---|---|---|
| BE-59 | 7-bromo-N-(4-(ethylsulfonyl)benzyl)-1-methyl-2-(4-(trifluoromethyl)benzyl)-1H-benzo[d]imidazole-5-carboxamide | 1 | 1.65 | 594, 596 |
| BE-60 | N-(4-(ethylsulfonyl)benzyl)-7-methoxy-1-methyl-2-(4-(trifluoromethyl)benzyl)-1H-benzo[d]imidazole-5-carboxamide | 1 | 1.47 | 546 |
| BE-61 | (R)-1-cyclopropyl-N-(1-(4-(ethylsulfonyl)phenyl)-2-hydroxyethyl)-2-(4-(trifluoromethyl)benzoyl)-1H-benzo[d]imidazole-5-carboxamide | 1 | 1.50 | 586.54 (M + 1) |
| BE-62 | (R)-1-cyclopropyl-N-(1-(4-(ethylsulfonyl)phenyl)-2-hydroxyethyl)-2-(4-(trifluoromethyl)piperidine-1-carbonyl)-1H-benzo[d]imidazole-5-carboxamide | 2 | 0.66 | 593 |
| BE-63.1 and BE-63.2 | 1-cyclopropyl-N-(4-(ethylsulfonyl)benzyl)-2-(hydroxy(trans-4-(trifluoromethyl)cyclohexyl)methyl)-1H-benzo[d]imidazole-5-carboxamide isomer 1 | 2 | 0.67 | 564, 586 |
|  | 1-cyclopropyl-N-(4-(ethylsulfonyl)benzyl)-2-(hydroxy(trans-4-(trifluoromethyl)cyclohexyl)methyl)-1H-benzo[d]imidazole-5-carboxamide isomer 2 | 2 | 0.67 | 564, 586 |
| BE-64 | 1-cyclopropyl-N-(4-(ethylsulfonyl)benzyl)-2-(4-(trifluoromethyl)cyclohexane-1-carbonyl)-1H-benzo[d]imidazole-5-carboxamide | 2 | 0.80 | 562, 584 |
| BE-65 | 1-cyclopropyl-N-(4-(ethylsulfonyl)benzyl)-2-(4-(trifluoromethyl)benzoyl)-1H-benzo[d]imidazole-5-carboxamide | 1 | 1.59 | 556.50 (M + 1) |
| BE-66 | (R)-2-(1-cyclopropyl-2-(((1r,4R)-4-(trifluoromethyl)cyclohexyl)methyl)-1H-benzo[d]imidazole-5-carboxamido)-2-(4-(ethylsulfonyl)phenyl)ethyl carbamate | 2 | 0.66 | 621 |
| BE-67 | (S)-2-(1-cyclopropyl-2-(((1r,4S)-4-(trifluoromethyl)cyclohexyl)methyl)-1H-benzo[d]imidazole-5-carboxamido)-2-(4-(ethylsulfonyl)phenyl)ethyl carbamate | 2 | 0.66 | 621 |
| BE-68 | 2-(4-(ethylsulfonyl)phenyl)-N-(1-isobutyl-2-(4-(trifluoromethyl)benzyl)-1H-benzo[d]imidazol-5-yl)acetamide | 1 | 1.22 | 558.30 (M + 1) |
| BE-69 | 2-(4-(ethylsulfonyl)phenyl)-N-(1-isobutyl-2-((4-(trifluoromethyl)piperidin-1-yl)methyl)-1H-benzo[d]imidazol-5-yl)acetamide | 1 | 1.11 | 565.36 (M + 1) |
| BE-70 | (R)-1-cyclopropyl-N-(1-(5-(ethylsulfonyl)pyridin-2-yl)-2-hydroxyethyl)-2-(4-(trifluoromethyl)phenoxy)-1H-benzo[d]imidazole-5-carboxamide | 2 | 0.75 | 575 |
| BE-71.1 and BE-71.2 | 1-cyclopropyl-N-((R)-1-(4-(ethylsulfonyl)phenyl)-2-hydroxyethyl)-2-(((((1s,4S)-4-(trifluoromethyl)cyclohexyl)oxy)methyl)-1H-benzo[d]imidazole-5-carboxamide | 2 | 0.81 | 594 |
|  | 1-cyclopropyl-N-((R)-1-(4-(ethylsulfonyl)phenyl)-2-hydroxyethyl)-2-(((((1r,4R)-4-(trifluoromethyl)cyclohexyl)oxy)methyl)-1H-benzo[d]imidazole-5-carboxamide | 2 | 0.8 | 594 |
| AB-1.1 | 3-cyclopropyl-N-(4-(ethylsulfonyl)benzyl)-2-(((1r,4r)-4-(trifluoromethyl)cyclohexyl)methyl)-3H-imidazo[4,5-b]pyridine-6-carboxamide | 2 | 0.85 | 549 |
| AB-1.2 | 3-cyclopropyl-N-(4-(ethylsulfonyl)benzyl)-2-(((1s,4s)-4-(trifluoromethyl)cyclohexyl)methyl)-3H-imidazo[4,5-b]pyridine-6-carboxamide | 2 | 0.85 | 549 |
| AB-2 | 3-cyclopropyl-N-(4-(methylsulfonyl)benzyl)-2-(4-(trifluoromethyl)benzyl)-3H-imidazo[4,5-b]pyridine-6-carboxamide | 1 | 1.35 | 529 |
| AB-3 | 3-cyclopropyl-N-(4-(ethylsulfonyl)benzyl)-2-(4-(trifluoromethyl)benzyl)-3H-imidazo[4,5-b]pyridine-6-carboxamide | 1 | 1.42 | 543 |

Biological Assays

Radio-Ligand RORγ Binding Assay (Assay 1)

Compounds described herein were tested for ability to bind to RORγ in a cell-free competition assay with commercially available radio-ligand (RL), 25-hydroxy [26,27-$^3$H]-cholesterol (PerkinElmer, Cat. # NET674250UC), for a ligand binding site on a recombinant RORγ Ligand Binding Domain (LBD) protein expressed as a 6×His-Glutathione-S-Transferase (GST) fusion. The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM β-octylglucopyranoside and 5 mM DTT. Tested compounds were dissolved in DMSO, and semi-log (3.162×) serial dilutions of the compounds were prepared in the same solvent. Two μL of the DMSO solutions were mixed with 28 μL of 8.6 nM 25-hydroxy [26,27-$^3$H]-cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. # RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. # T2320). The percent inhibition vs. concentration data were fit into a four-parameter model, and IC50 values were calculated from the fit as the concentrations corresponding to the inflection points on the dose-response curves. Inhibitory constants (Ki) were calculated using the following equation, where [RL] is the concentration in the assay and K$_D$ is a dissociation constant of 25-hydroxy [26,27-$^3$H]-cholesterol:

$$K_i = \frac{IC_{50}}{\left(1 + \frac{[RL]}{K_D}\right)}.$$

RORγt 5×RORE Assay in Jurkat Cells (Assay 2)

Compounds described herein were tested for RORγ inverse agonist activity in a cell-based, transcriptional activity assay. Secreted Nanoluc® luciferase was used as a reporter for transcriptional activity of the full-length RORγt in Jurkat cells (ATCC, Cat. # TIB-152). A reporter plasmid was constructed by inserting 5 repeats of the ROR Response Element (RORE) AAAGTAGGTCA (SEQ ID NO: 1) into a commercially available promoterless plasmid pNL1.3[secNluc] (Promega, Cat. # N1021) using KpnI and HindIII restriction sites. The expression plasmid for RORγt was purchased (Geneocopoeia, Cat. # EX-T6988-M02). Jurkat cells (30 million cells) were transfected with 11 μg of EX-T6988-MO2 and 26 μg of the reporter plasmid in OptiMEM® media using Lipofectaminec LTX and Plus™ reagents (Life Technologies, Cat. #15338-100). After 5-6 hrs of incubation at 37° C./5% CO$_2$, the cells were collected, resuspended in phenol-red free RPMT media containing 10% (v/v) delipidated FBS (Hyclone, Cat. # SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% CO$_2$ for 16-18 hrs. Luciferase activity in the conditioned supernatants was determined with NanoGlo® assay reagents (Promega, Cat. # N1130). Percent inhibition values were calculated based on the fully inhibited and non-inhibited (DMSO) controls, and the values were regressed against concentrations of the tested compounds to derive IC50 values using a four-parameter non-linear fitting model.

The results of assays 1 and 2 are shown in Table 1.

TABLE 1

| Cpd No | Ki (nM) (Assay 1) | IC50 (nM) (Assay 2) |
|---|---|---|
| IN-1 | +++ | +++ |
| IN-2 | +++ | +++ |
| IN-3 | +++ | +++ |
| IN-4.1 | +++ | +++ |
| IN-4.2 | +++ | ++ |
| IN-5 | +++ | +++ |
| IN-6 | +++ | ++ |
| IN-7 | +++ | ++ |
| IN-8 | +++ | ++ |
| IN-9 | +++ | +++ |
| IN-10 | +++ | +++ |
| IN-11 | +++ | +++ |
| IN-12 | +++ | +++ |
| IN-13 | +++ | +++ |
| IN-14.1 | +++ | +++ |
| IN-14.2 | +++ | ++ |
| IN-15.1 | +++ | +++ |
| IN-15.2 | +++ | + |
| IN-16.1 | +++ | +++ |
| IN-16.2 | +++ | + |
| IN-17.1 | +++ | +++ |
| IN-17.2 | +++ | + |
| IN-18 | +++ | +++ |
| IN-19 | +++ | +++ |
| IN-20 | ++ | nt |
| IN-21 | +++ | ++ |
| IN-22 | +++ | +++ |
| IN-23 | ++ | nt |
| AI-1 | +++ | +++ |
| AI-2 | +++ | +++ |
| AI-3 | +++ | ++ |
| BE-1 | +++ | +++ |
| BE-2 | +++ | +++ |
| BE-3 | +++ | ++ |
| BE-4.1 | +++ | ++ |
| BE-4.2 | +++ | + |
| BE-5 | +++ | +++ |
| BE-6 | +++ | +++ |
| BE-7 | +++ | +++ |
| BE-8 | +++ | +++ |
| BE-9 | +++ | +++ |
| BE-10 | ++ | nt |
| BE-11 | +++ | +++ |
| BE-12 | +++ | + |
| BE-13 | +++ | + |
| BE-14 | +++ | +++ |
| BE-15 | +++ | +++ |
| BE-16 | +++ | +++ |
| BE-17 | +++ | + |
| BE-18.1 | +++ | +++ |
| BE-18.2 | +++ | + |
| BE-19.1 | +++ | +++ |
| BE-19.2 | +++ | + |
| BE-20 | +++ | +++ |
| BE-21 | +++ | +++ |
| BE-22 | +++ | ++ |
| BE-23 | +++ | +++ |
| BE-24 | ++ | nt |
| BE-25 | +++ | +++ |
| BE-26.1 | +++ | + |
| BE-26.2 | +++ | + |
| BE-27.1 | +++ | +++ |
| BE-27.2 | +++ | + |
| BE-28 | +++ | +++ |
| BE-29 | + | nt |
| BE-30 | +++ | +++ |

TABLE 1-continued

| Cpd No | Ki (nM) (Assay 1) | IC50 (nM) (Assay 2) |
| --- | --- | --- |
| BE-31 | +++ | + |
| BE-32 | +++ | +++ |
| BE-33 | +++ | +++ |
| BE-34 | ++ | ++ |
| BE-35 | +++ | +++ |
| BE-36 | +++ | +++ |
| BE-37 | +++ | +++ |
| BE-38 | +++ | ++ |
| BE-39 | +++ | ++ |
| BE-40 | ++ | nt |
| BE-41 | +++ | ++ |
| BE-42 | ++ | nt |
| BE-43 | +++ | ++ |
| BE-44 | ++ | nt |
| BE-45 | +++ | ++ |
| BE-46.1 | +++ | ++ |
| BE-46.2 | +++ | + |
| BE-47 | +++ | +++ |
| BE-48 | +++ | +++ |
| BE-49 | +++ | ++ |
| BE-50 | ++ | ++ |
| BE-51 | ++ | nt |
| BE-52 | +++ | + |
| BE-53 | +++ | +++ |
| BE-54 | +++ | +++ |
| BE-55.1 | ++ | + |
| BE-55.2 | +++ | +++ |
| BE-56.1 | ++ | nt |
| BE-56.2 | ++ | nt |
| BE-56.3 | ++ | nt |
| BE-56.4 | ++ | nt |
| BE-57.1 | ++ | ++ |
| BE-57.2 | +++ | ++ |
| BE-57.3 | ++ | nt |
| BE-57.4 | ++ | nt |
| BE-58 | ++ | nt |
| BE-59 | ++ | nt |
| BE-60 | ++ | nt |
| BE-61 | +++ | +++ |
| BE-62 | ++ | nt |
| BE-63.1 | + | nt |
| BE-63.2 | ++ | nt |
| BE-64 | +++ | ++ |
| BE-65 | +++ | +++ |
| BE-66 | +++ | +++ |
| BE-67 | +++ | +++ |
| BE-68 | +++ | ++ |
| BE-69 | ++ | ++ |
| BE-70 | +++ | +++ |
| BE-71.1 | +++ | +++ |
| BE-71.2 | +++ | +++ |
| AB-1.1 | +++ | +++ |
| AB-1.2 | +++ | + |
| AB-2 | ++ | nt |
| AB-3 | +++ | +++ | nt = not tested;
+ means >1000 nM;
++ means 100 nM-1000 nM;
+++ means <100 nM.

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of the formula:

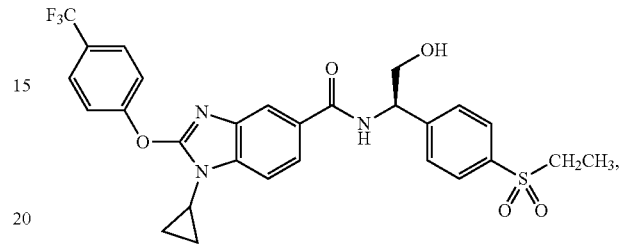

or a pharmaceutically acceptable salt thereof.

2. A compound of the formula:

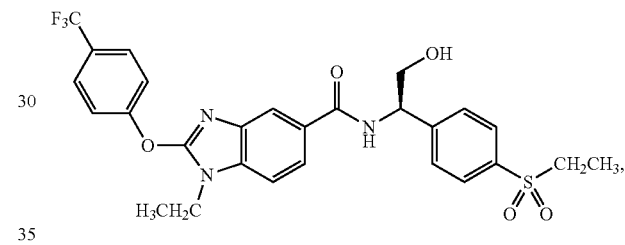

or a pharmaceutically acceptable salt thereof.

3. A compound of the formula:

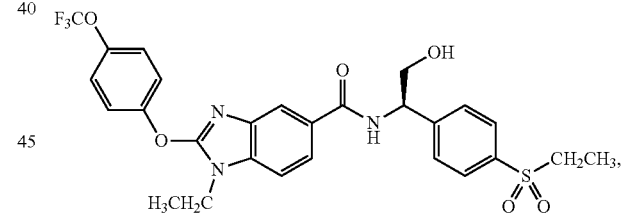

or a pharmaceutically acceptable salt thereof.

4. A pharmaceutical composition comprising a pharmaceutically acceptable carrier and the compound of claim 1, or a pharmaceutically acceptable salt thereof.

5. A pharmaceutical composition comprising a pharmaceutically acceptable carrier and the compound of claim 2, or a pharmaceutically acceptable salt thereof.

6. A pharmaceutical composition comprising a pharmaceutically acceptable carrier and the compound of claim 3, or a pharmaceutically acceptable salt thereof.

* * * * *